United States Patent
Hasegawa et al.

(10) Patent No.: US 12,215,243 B2
(45) Date of Patent: Feb. 4, 2025

(54) PHENOL COMPOUND, CONDUCTIVE PASTE COMPOSITION, METHOD FOR PRODUCING CONDUCTIVE PASTE COMPOSITION, CONDUCTIVE WIRE, AND METHOD FOR PRODUCING CONDUCTIVE WIRE

(71) Applicant: SHIN-ETSU CHEMICAL CO., LTD., Tokyo (JP)

(72) Inventors: Koji Hasegawa, Joetsu (JP); Shiori Nonaka, Joetsu (JP); Osamu Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 18/029,934

(22) PCT Filed: Oct. 14, 2021

(86) PCT No.: PCT/JP2021/038019
§ 371 (c)(1),
(2) Date: Apr. 3, 2023

(87) PCT Pub. No.: WO2022/107511
PCT Pub. Date: May 27, 2022

(65) Prior Publication Data
US 2023/0332008 A1  Oct. 19, 2023

(30) Foreign Application Priority Data
Nov. 20, 2020 (JP) ............................. 2020-193741

(51) Int. Cl.
*C07C 39/16* (2006.01)
*C07C 39/19* (2006.01)
(Continued)

(52) U.S. Cl.
CPC .............. *C09D 11/52* (2013.01); *C07C 39/16* (2013.01); *C07C 39/19* (2013.01); *C07C 43/23* (2013.01); *C07C 69/50* (2013.01); *C07F 7/081* (2013.01); *C07F 7/0838* (2013.01); *C09D 11/037* (2013.01); *C09D 11/102* (2013.01);
(Continued)

(58) Field of Classification Search
CPC ..... C09D 11/52; C09D 11/037; C09D 11/102; C09D 175/06; C07C 39/16; C07C 39/19; C07C 43/23; C07C 69/50; C07C 2601/14; C07C 2603/74; C07C 39/15; C07C 39/367; C07C 49/255; C07C 49/83; C07C 49/84; C07C 69/28; C07C 69/92; C07C 255/13; C07C 255/54; C07C 39/11; C07C 39/12; C07C 39/27; C07C 69/16; C07C 69/712; C07C 39/373; C07C 69/63; C07F 7/081; C07F 7/0838; C07F 7/08; H01B 1/22; H01B 5/14; H01B 13/0016; H01B 1/20; H01B 13/00; H01B 13/0026; H01B 7/06; C08K 2003/0806; C08K 2201/001; C08K 2201/002; C08K 2201/005; C08K 3/01; C08K 5/13; C08G 18/10; C08G 18/227; C08G 18/42; C08G 18/4277; C08G 18/44; C08G 18/755; C08G 18/7621; C08G 18/65; C08L 75/04; C08L 101/12
See application file for complete search history.

(56) References Cited

U.S. PATENT DOCUMENTS 6,402,992 B1 * 6/2002 Kumar .................. H01B 1/128
  252/500
2005/0100772 A1  5/2005 Ono
(Continued)

FOREIGN PATENT DOCUMENTS

CN   105482118 A   4/2016
DE      297155 A5   1/1992
(Continued)

OTHER PUBLICATIONS

Jun. 6, 2023 Decision of Refusal issued in Japanese Patent Application No. 2022-194204.
(Continued)

*Primary Examiner* — Mark Kopec
*Assistant Examiner* — Jaison P Thomas
(74) *Attorney, Agent, or Firm* — Oliff PLC

(57) ABSTRACT

The present invention is a phenol compound represented by the following general formula (1A). This phenol compound makes it possible to provide a phenol compound as an additive for a conductive paste composition having a small decrease in electric conductivity in repetitive elongations and shrinkages and excellent printing processability, a conductive paste composition containing the additive, and a conductive wire made by using the conductive paste composition.

(1A)

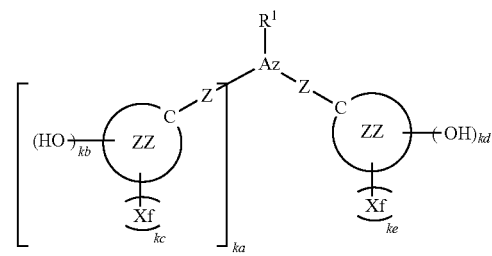

15 Claims, No Drawings

(51) Int. Cl.
| | |
|---|---|
| *C07C 43/23* | (2006.01) |
| *C07C 69/50* | (2006.01) |
| *C07F 7/08* | (2006.01) |
| *C09D 11/037* | (2014.01) |
| *C09D 11/102* | (2014.01) |
| *C09D 11/52* | (2014.01) |
| *H01B 1/22* | (2006.01) |
| *H01B 5/14* | (2006.01) |
| *H01B 13/00* | (2006.01) |

(52) U.S. Cl.
CPC ............... *H01B 1/22* (2013.01); *H01B 5/14* (2013.01); *H01B 13/0016* (2013.01)

(56) References Cited

U.S. PATENT DOCUMENTS

| | | | |
|---|---|---|---|
| 2007/0018315 A1* | 1/2007 | Craig | ............... H01B 1/22 257/734 |
| 2015/0083465 A1 | 3/2015 | Yun et al. | |
| 2016/0130471 A1* | 5/2016 | Burrows | ............... H05K 1/0326 252/514 |
| 2016/0372230 A1 | 12/2016 | Imahashi | |
| 2017/0169914 A1 | 6/2017 | Sekitani et al. | |
| 2017/0200527 A1* | 7/2017 | Pujari | ............... B22F 1/068 |
| 2020/0115482 A1 | 4/2020 | Sakamoto et al. | |

FOREIGN PATENT DOCUMENTS

| | | |
|---|---|---|
| JP | 107-278058 A | 10/1995 |
| JP | H08-073780 A | 3/1996 |
| JP | 2003-026637 A | 1/2003 |
| JP | 2004-143446 A | 5/2004 |
| JP | 2005-259392 A | 9/2005 |
| JP | 2006-104232 A | 4/2006 |
| JP | 2011-153265 A | 8/2011 |
| JP | 2013-112694 A | 6/2013 |
| JP | 2017-062423 A | 3/2017 |
| JP | 2017-103071 A | 6/2017 |
| JP | 6319085 B2 | 5/2018 |
| KR | 101205004 B1 | 11/2012 |
| KR | 101205006 B1 | 11/2012 |
| WO | 2013021895 A1 | 2/2013 |
| WO | 2015119217 A1 | 8/2015 |
| WO | 2018/123622 A1 | 7/2018 |
| WO | 2020/059476 A1 | 3/2020 |

OTHER PUBLICATIONS

Aug. 11, 2023 Office Action issued in Indian Patent Application No. 202347027074.
Aug. 14, 2023 Office Action and Search Report issued in Chinese Patent Application No. 202111402270.1.
Iwanami Dictionary of Science and Chemistry, 5th ed., Apr. 24, 1998, pp. 387 & 1106.
Registry(STN)[online], Sep. 7, 1990, RN129188-99-4, other 13 compounds.
Cigl et al., "Lateral Substituted Phenyl Biphenylcarboxylates-Non-Chiral Analogues of Ferroelectric Liquid Crystals," Liquid Crystals, Oct. 29. 2019 (Online published), vol. 47 No. 5, pp. 768-776, Supplemental information (p. 1-23).
Ohtake et al., "Liquid-Crystalline Complexes of Mesogenic Dimers Containing Oxyethlene Moietis with LiCF3SO3: Self-Organized Ion Conductive Materials," Chemistry of Materials, 2000, vol. 12, No. 3, pp. 782-789.
Dec. 21, 2021 International Search Report issued in International Patent Applicatio No. PCT/JP2021/038019.
May 16, 2023 International Preliminary Report on Patentability issued in International Patent Applciation No. PCT/JP2021/038019.
Feb. 7, 2023 Office Action issued in Japanese Patent Application No. 2022-194204.
Oct. 23, 2024 Extended European Search Report issued in European Patent Application No. 21894385.0.
Zhao et al., "A novel strategy for constructing a highly conductive and swelling-resistant semi-flexible aromatic polymer based anion exchange membranes," International Journal of Hydrogen Energy, vol. 42, No. 15, pp. 10228-10237 (2017).
Khan et al., "Arene ruthenium dichloro complexes containing isonicotinic ester ligands: Synthesis, molecular structure and cytotoxicity," Journal of Organometallic Chemistry, vol. 730, No. 15, pp. 49-56 (2013).
Nov. 25, 2024 Hearing Notice issued in Indian Patent Application No. 202347027074.

* cited by examiner

PHENOL COMPOUND, CONDUCTIVE PASTE COMPOSITION, METHOD FOR PRODUCING CONDUCTIVE PASTE COMPOSITION, CONDUCTIVE WIRE, AND METHOD FOR PRODUCING CONDUCTIVE WIRE

TECHNICAL FIELD

The present invention relates to a conductive paste composition capable of producing a highly conductive and stretchable conductive wire, and to a phenol compound contained in the composition.

BACKGROUND ART

In recent years, in the field of sports or health care, active development and research of wearable devices have been made for the purpose of acquiring vital signs such as a heart rate and a respiratory rate by attaching the devices to a human body. Such wearable devices usually include a bio-electrode for detecting electrical signals from a body, wires for transmitting the electrical signals to a sensor, a semiconductor chip serving as the sensor, and a battery. When a device is made to be attached to a human body, the device desirably has stretching performance in accordance with the maximum stretch at the knee and the elbow of clothes worn by a human in a motion state, which is about 50%. Even if the wire itself does not have stretchability, it is possible to secure electric conductivity when the wire is extended by forming bellows-shaped wiring in which horseshoe-shaped wires are aligned or by forming a wrinkled substrate.

If conductivity at the time of elongation and shrinkage can be ensured even in a straight wire, which is not bellows-shaped, more compact wiring area and a beautiful design can be obtained, and the cost can be reduced. Further, as the conductivity increases, the conduction can be secured even when the wire is made thin to some extent. An extremely thin wire, which is almost invisible, nearly extinguishes the presence of wire, which allows for flexible designs and a cool impression. For this reason, conductive pastes and conductive inks having high conductivity and stretchability have been actively developed.

Examples of stretchable conductive paste include an conductive paste obtained by incorporating metal powder in an elastomer binder containing a sulfur atom or a nitrile group to thereby impart flexibility and stretchability to a conductor (Patent Document 1).

Further, Patent Document 2 proposes a stretchable conductor in which the incorporation amounts of conductive particles, fluororubber, and fluorinated surfactant aqueous solution are optimized so as to ensure an electric conductivity more than 100 S/cm at the time of elongation and shrinkage of about 200%.

CITATION LIST

Patent Literature

Patent Document 1: JP6319085B
Patent Document 2: WO2015/119217A1

SUMMARY OF INVENTION

Technical Problem

However, even the conductor made of a stretchable conductive composition, such as the one described above, may experience a rapid decrease in electric conductivity as the elongation and shrinkage are repeated, or, in some cases, the conductor may even break. Therefore, a conductive paste composition for producing a conductor having excellent stability of electric conductivity even when the elongation and shrinkage are repeated has been demanded.

The present invention has been made in view of the above-described circumstances, and an object of the present invention is to provide a phenol compound as an additive for a conductive paste composition having a small decrease in electric conductivity in repetitive elongations and shrinkages and excellent printing processability, a conductive paste composition containing the additive, and a conductive wire made by using the conductive paste composition.

Solution to Problem

In order to achieve the above object, the present invention provides a phenol compound represented by the following general formula (1A).

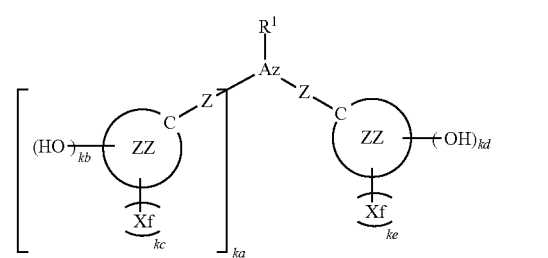

(1A)

wherein $R^1$ represents a hydrogen atom, a halogen atom, a cyano group, or a hydroxyl group, Az represents a linear, branched, or cyclic (ka+2)-valent hydrocarbon group or fluorinated hydrocarbon group having 1 to 20 carbon atoms, and —$CH_2$— constituting the (ka+2)-valent hydrocarbon group is optionally substituted with —O—, —C(=O)— or —Si($R^2R^3$)—, each of $R^2$ and $R^3$ is a linear, branched, or cyclic alkyl group having 1 to 6 carbon atoms, or a phenyl group, each Xf independently represents a hydrogen atom, a halogen atom, a linear, branched, or cyclic monovalent hydrocarbon group having 1 to 10 carbon atoms optionally substituted with a fluorine atom, an alkoxy group having 1 to 10 carbon atoms optionally substituted with a fluorine atom, or an electron-withdrawing group, Z represents a single bond or an oxygen atom; Each of a ring ZZ independently represents an aromatic monocyclic or polycyclic ring having 5 to 20 carbon atoms, each carbon atom of the ring ZZ is optionally substituted with a nitrogen atom, an oxygen atom, or a sulfur atom; "ka" represents an integer of 0 to 2; "kb" and "kd" each represent 1 or 2; "kc" and "ke" each represent an integer of 0 to 2.

Such a phenol compound may be used as an additive for a conductive paste composition having a small decrease in electric conductivity in repetitive elongations and shrinkages and excellent printing processability.

Further, in the present invention, a phenol compound represented by the following general formula (1B) is preferable.

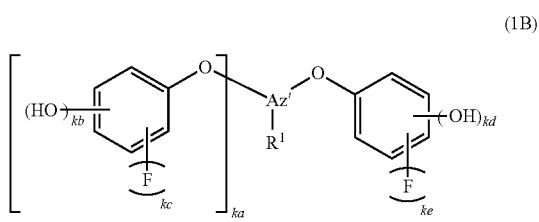

(1B)

Az' represents a linear, branched, or cyclic (ka+2)-valent hydrocarbon group or fluorinated hydrocarbon group having 1 to 19 carbon atoms, and —$CH_2$— constituting the (ka+2)-valent hydrocarbon group is optionally substituted with —O—, —C(=O)— or —Si($R^2R^3$)—; "ka" represents 0 or 1, "kb", "kc", "kd", and "ke" each represent 1 or 2, $R^1$, $R^2$ and $R^3$ are as defined above.

Such a phenol compound may be used as more suitable additive for a conductive paste composition having a small decrease in electric conductivity in repetitive elongations and shrinkages and excellent printing processability.

The present invention also provides a conductive paste composition containing (A) a conductive filler, (B) a phenol compound, (C) an elastomer resin, and (D) a solvent, in which the phenol compound as the component (B) is a phenol compound described below.

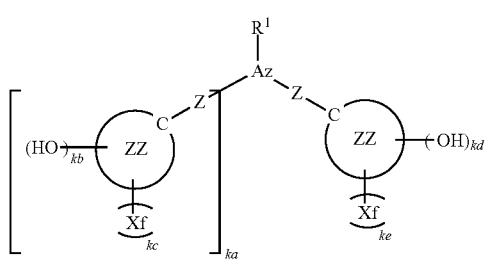

(1A)

wherein $R^1$ represents a hydrogen atom, a halogen atom, a cyano group, or a hydroxyl group, Az represents a linear, branched, or cyclic (ka+2)-valent hydrocarbon group or fluorinated hydrocarbon group having 1 to 20 carbon atoms, and —$CH_2$— constituting the (ka+2)-valent hydrocarbon group is optionally substituted with —O—, —C(=O)— or —Si($R^2R^3$)—, each of $R^2$ and $R^3$ is a linear, branched, or cyclic alkyl group having 1 to 6 carbon atoms, or a phenyl group, each Xf independently represents a hydrogen atom, a halogen atom, a linear, branched, or cyclic monovalent hydrocarbon group having 1 to 10 carbon atoms optionally substituted with a fluorine atom, an alkoxy group having 1 to 10 carbon atoms optionally substituted with a fluorine atom, or an electron-withdrawing group, Z represents a single bond or an oxygen atom; each ring ZZ independently represents an aromatic monocyclic or polycyclic ring having 5 to 20 carbon atoms, each carbon atom of the ring ZZ is optionally substituted with a nitrogen atom, an oxygen atom, or a sulfur atom; "ka" represents an integer of 0 to 2; "kb" and "kd" each represent 1 or 2; "kc" and "ke" each represent an integer of 0 to 2.

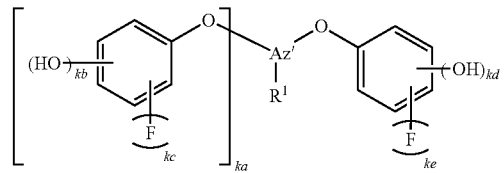

(1B)

Az' represents a linear, branched, or cyclic (ka+2)-valent hydrocarbon group or fluorinated hydrocarbon group having 1 to 19 carbon atoms, and —$CH_2$— constituting the (ka+2)-valent hydrocarbon group is optionally substituted with —O—, —C(=O)— or —Si($R^2R^3$)—; "ka" represents 0 or 1, "kb", "kc", "kd", and "ke" each represent 1 or 2, $R^1$, $R^2$ and $R^3$ are as defined above.

Such a conductive paste composition has a small decrease in electric conductivity in repetitive elongations and shrinkages and excellent printing processability.

In this case, a conductive paste composition in which the elastomer resin as the component (C) is polyurethane is preferable.

Such a conductive paste composition has a small decrease in electric conductivity in repetitive elongations and shrinkages and superior printing processability.

Further, in the present invention, a conductive paste composition in which the elastomer resin as the component (C) is polyurethane having the structures represented by the following general formulae (1a) to (1c) is preferable.

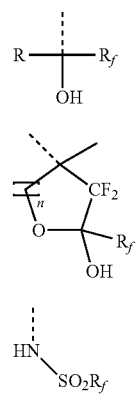

(1a)

(1b)

(1c)

wherein R represents a hydrogen atom, a fluorine atom, or a linear, branched, or cyclic hydrocarbon group having 1 to 10 carbon atoms optionally substituted with a fluorine atom; $R_f$ represents a fluorine atom, or a linear, branched, or cyclic fluorinated hydrocarbon group having 1 to 10 carbon atoms; "n" is an integer of 1 or 2; and the dashed line represents a bonding arm.

Such a conductive paste composition has a small decrease in electric conductivity in repetitive elongations and shrinkages and superior printing processability.

Further, a conductive paste composition in which the elastomer resin as the component (C) is polyurethane having the structures represented by the following general formulae (2a) to (2c) is preferable.

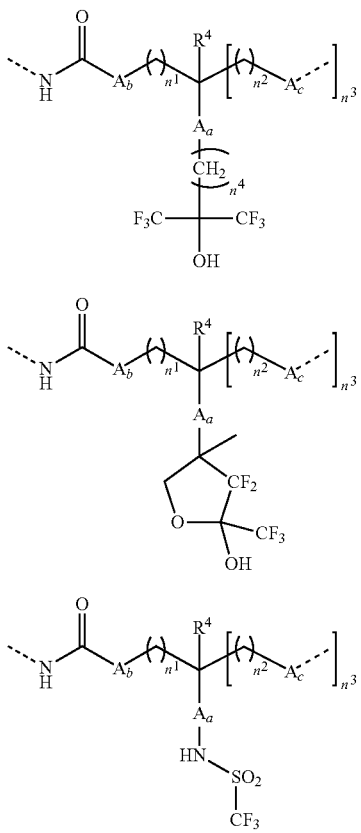

(2a)

(2b)

(2c)

wherein $R^4$ is a hydrogen atom or a monovalent hydrocarbon group having 1 to 3 carbon atoms; $A_a$ represents a single bond, or a linear, branched, or cyclic divalent hydrocarbon group having 1 to 20 carbon atoms; and —$CH_2$— constituting $A_a$ is optionally substituted with —O—, —C(=O)—, —C(=O)O— or —$C_6H_4$—, or —$NR^8$—C(=O)—; $R^8$ is a hydrogen atom, or a linear or branched alkyl group having 1 to 4 carbon atoms, $A_b$ represents —O—, —$NR^8$—, or —C(=O)O—; $A_c$ represents —O—, —$NR^8$—, —C(=O)O—, or —$NR^8$—C(=O)—; each of $n^1$, $n^2$, and $n^4$ is an integer of 0 to 10; $n^3$ is an integer of 0 or 1; and a dashed line represents a bonding arm.

Such a conductive paste composition becomes further preferable as a conductive paste composition having small decrease in electric conductivity in repetitive elongations and shrinkages and excellent printing processability.

Further, in the present invention, the conductive filler as the component (A) is preferably contained in a proportion exceeding 70 parts by mass relative to 100 parts by mass of a total of the components (A) and (C).

Such a conductive paste composition can form a conductive wire whose electric conductivity varies more slightly at the time of elongation and shrinkage.

Further, in the present invention, the conductive filler as the component (A) is preferably a conductive paste composition selected from the group consisting of gold, silver, silver chloride, platinum, copper, tin, iron, titanium, nickel, palladium, aluminum, tungsten, molybdenum, ruthenium, chromium, indium, solder, carbon, and composites thereof.

Such a conductive paste composition enables formation of a conductive wire having higher electrical conductivity.

Further, the conductive paste composition of the present invention is preferably such that a silver powder having an average particle size of 5 nm to 10 μm is used as the conductive filler as the component (A).

Such a conductive filler is suitably incorporated in the conductive paste composition.

The present invention also provides a method for producing a conductive paste composition, wherein the elastomer as the component (C) is a polyurethane having the structure represented by (2a) to (2c) above, and the elastomer resin as the component (C) is produced using an alcohol represented by the following general formulae (3a) to (3c) as a chain extender.

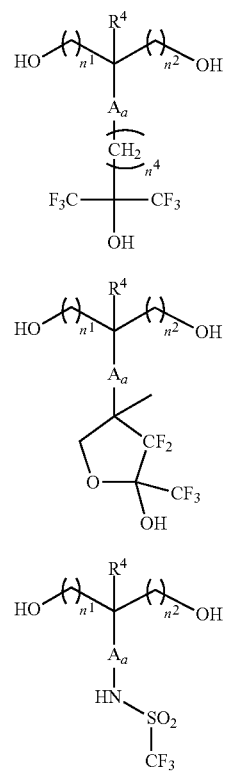

(3a)

(3b)

(3c)

wherein $R^4$, $A_a$, $n^1$, $n^2$ and $n^4$ are as defined above.

According to such a method for producing a polyurethane, the polyurethane can be easily synthesized.

Moreover, the present invention provides a conductive wire, which is made from a baked product of the conductive paste composition, and is formed on a substrate.

The electric conductivity of such a conductive wire varies slightly at the time of elongation and shrinkage.

Further, the conductive wire of the present invention is preferably such that the substrate is stretchable.

Such a substrate is suitable for the conductive wire of the present invention.

Further, the conductive wire of the present invention is preferably such that the substrate is a thermoplastic polyurethane.

Such a substrate is more suitable for the conductive wire of the present invention.

Further, in the present invention, a change in electric resistance of the conductive wire upon 20% elongation is 500% or less.

The electric conductivity of such a conductive wire varies slightly at the time of elongation and shrinkage, and the conductive wire is adaptable to an attachment location on skin.

Further, the conductive wire of the present invention is preferably such that a maximum resistance value of the conductive wire which is elongated and shrunk repeatedly 1000 times with an elongation ratio of 20% is 5000% or less of the resistance value before the elongations and the shrinkages.

Such a conductive wire has suitable conduction stability in repetitive elongations and shrinkages.

In addition, the present invention provides a method for producing a conductive wire by using the conductive paste composition described above to form a conductive wire on a substrate, wherein the conductive wire is formed with a baking temperature of 60° C. to 160° C.

Such a method for producing a conductive wire makes it possible to reliably obtain a conductive wire which varies slightly in electric conductivity at the time of elongation and shrinkage.

Further, the present invention may print the conductive paste composition to form a conductive wire on a substrate.

By thus forming a wire pattern by printing, the productivity can be improved.

Advantageous Effects of Invention

The conductive paste composition of the present invention makes it possible to form a conductive wire which has a slight decrease in electric conductivity at the time of repetitive elongations and shrinkages and is capable of efficiently conducting electric signals to a device (i.e., excellent in electric conductivity), and which is excellent in printing processability, light-weight, and is manufacturable at low cost.

Moreover, because of the excellent conduction stability in repetitive elongations and shrinkages, it is possible to form a conductive wire suitable for wearable devices in which strain is generated by human body movement.

Furthermore, the present invention provides a phenol compound suitable as an additive to be incorporated in the conductive paste composition described above.

DESCRIPTION OF EMBODIMENTS

As described above, developments of a phenol compound as an additive for a conductive paste composition having a small decrease in electric conductivity in repetitive elongations and shrinkages and excellent printing processability, a conductive paste composition containing the additive, and a conductive wire made by using the conductive paste composition have been in demand.

In order to achieve the above object, the present inventors have conducted intensive studies, and consequently found that a phenol compound represented by the following general formula (1A) can be very easily obtained, and that a conductive paste composition obtained by using this phenol compound as an additive can provide a conductive wire having a low resistance, a small decrease in electric conductivity at the time of elongation, and an excellent stable conductivity in repetitive elongations and shrinkages.

Specifically, the present invention is a phenol compound represented by the following general formula (1A).

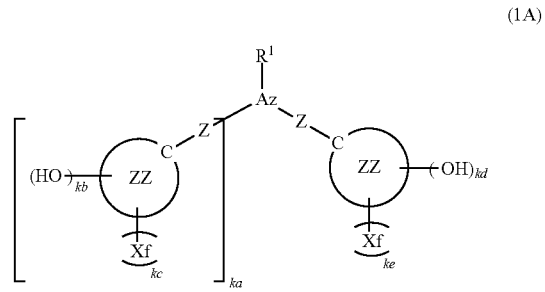

(1A)

wherein $R^1$ represents a hydrogen atom, a halogen atom, a cyano group, or a hydroxyl group, Az represents a linear, branched, or cyclic (ka+2)-valent hydrocarbon group or fluorinated hydrocarbon group having 1 to 20 carbon atoms, and —$CH_2$— constituting the (ka+2)-valent hydrocarbon group is optionally substituted with —O—, —C(=O)— or —Si($R^2R^3$)—, each of $R^2$ and $R^3$ is a linear, branched, or cyclic alkyl group having 1 to 6 carbon atoms, or a phenyl group, each Xf independently represents a hydrogen atom, a halogen atom, a linear, branched, or cyclic monovalent hydrocarbon group having 1 to 10 carbon atoms optionally substituted with a fluorine atom, an alkoxy group having 1 to 10 carbon atoms optionally substituted with a fluorine atom, or an electron-withdrawing group, Z represents a single bond or an oxygen atom; Each of a ring ZZ independently represents an aromatic monocyclic or polycyclic ring having 5 to 20 carbon atoms, each carbon atom of the ring ZZ is optionally substituted with a nitrogen atom, an oxygen atom, or a sulfur atom; "ka" represents an integer of 0 to 2; "kb" and "kd" each represent 1 or 2; "kc" and "ke" each represent an integer of 0 to 2.

The present invention is described below in detail; however, the present invention is not limited to the examples described below. In the following description, an asymmetric carbon is present in some structures represented by chemical formulae. Also, an enantiomer or a diastereomer may be present; in this case, these isomers are represented by one representative formula. These isomers may be used individually or as a mixture.

Phenol Compound

The phenol compound of the present invention is represented by the following general formula (1A), and is incorporated as an additive for a conductive paste composition.

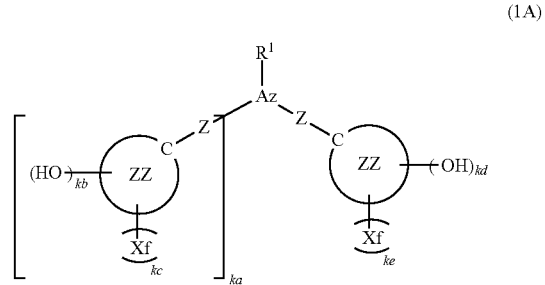

(1A)

wherein $R^1$ represents a hydrogen atom, a halogen atom, a cyano group, or a hydroxyl group, Az represents a linear, branched, or cyclic (ka+2)-valent hydrocarbon group or fluorinated hydrocarbon group having 1 to 20 carbon atoms, and —$CH_2$— constituting the (ka+2)-valent hydrocarbon group is optionally substituted with —O—, —C(=O)— or —Si($R^2R^3$)—, each of $R^2$ and $R^3$ is a linear, branched, or cyclic alkyl group having 1 to 6 carbon atoms, or a phenyl group, each Xf independently represents a hydrogen atom, a halogen atom, a linear, branched, or cyclic monovalent hydrocarbon group having 1 to 10 carbon atoms optionally substituted with a fluorine atom, an alkoxy group having 1 to 10 carbon atoms optionally substituted with a fluorine atom, or an electron-withdrawing group, Z represents a single bond or an oxygen atom; Each of a ring ZZ independently represents an aromatic monocyclic or polycyclic ring having 5 to 20 carbon atoms, each carbon atom of the ring ZZ is optionally substituted with a nitrogen atom, an oxygen atom, or a sulfur atom; "ka" represents an integer of 0 to 2; "kb" and "kd" each represent 1 or 2; "kc" and "ke" each represent an integer of 0 to 2.

Specific examples of the linear, branched, or cyclic (ka+2)-valent hydrocarbon group having 1 to 20 carbon atoms as Az include the following substances.

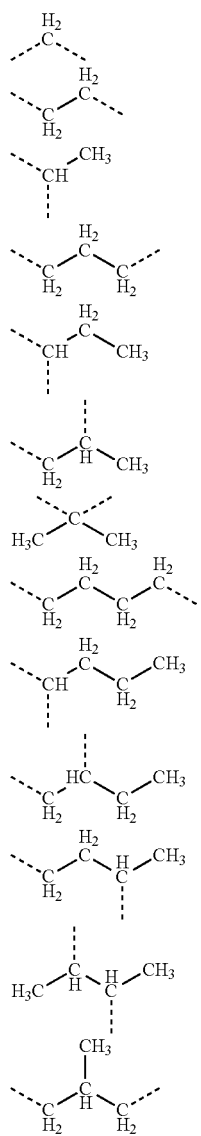

-continued

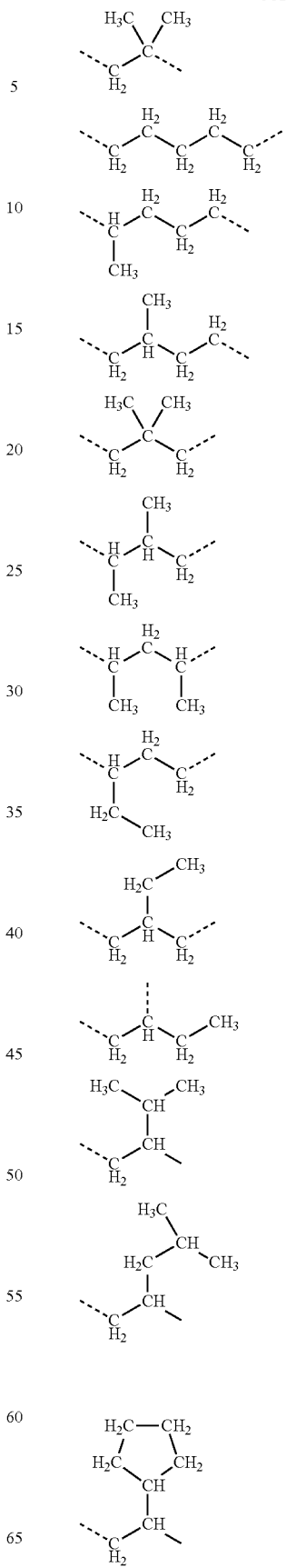

-continued
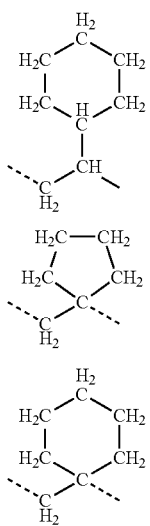
wherein the dashed line represents a bonding arm.
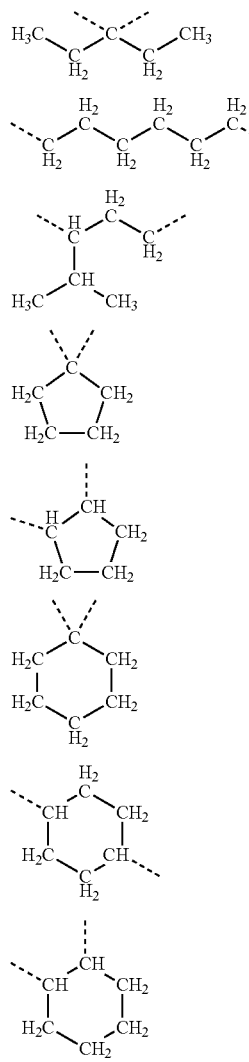
-continued
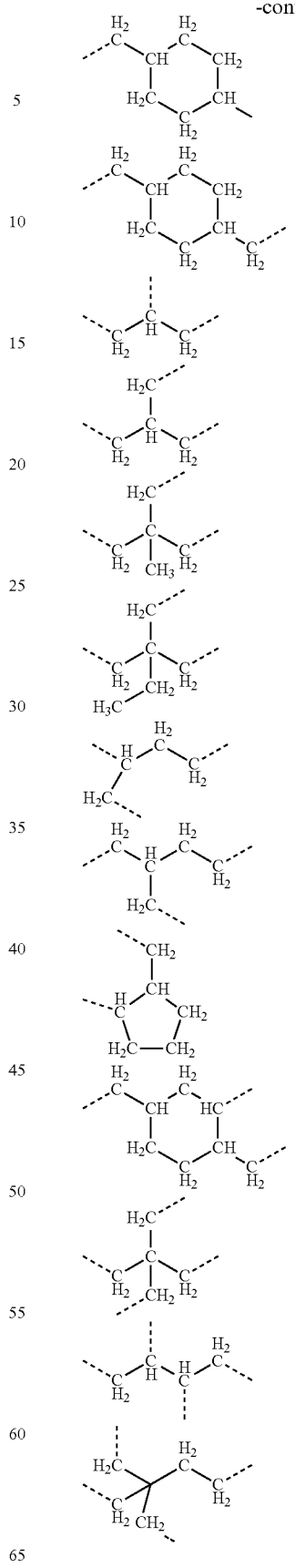
wherein the dashed line represents a bonding arm.

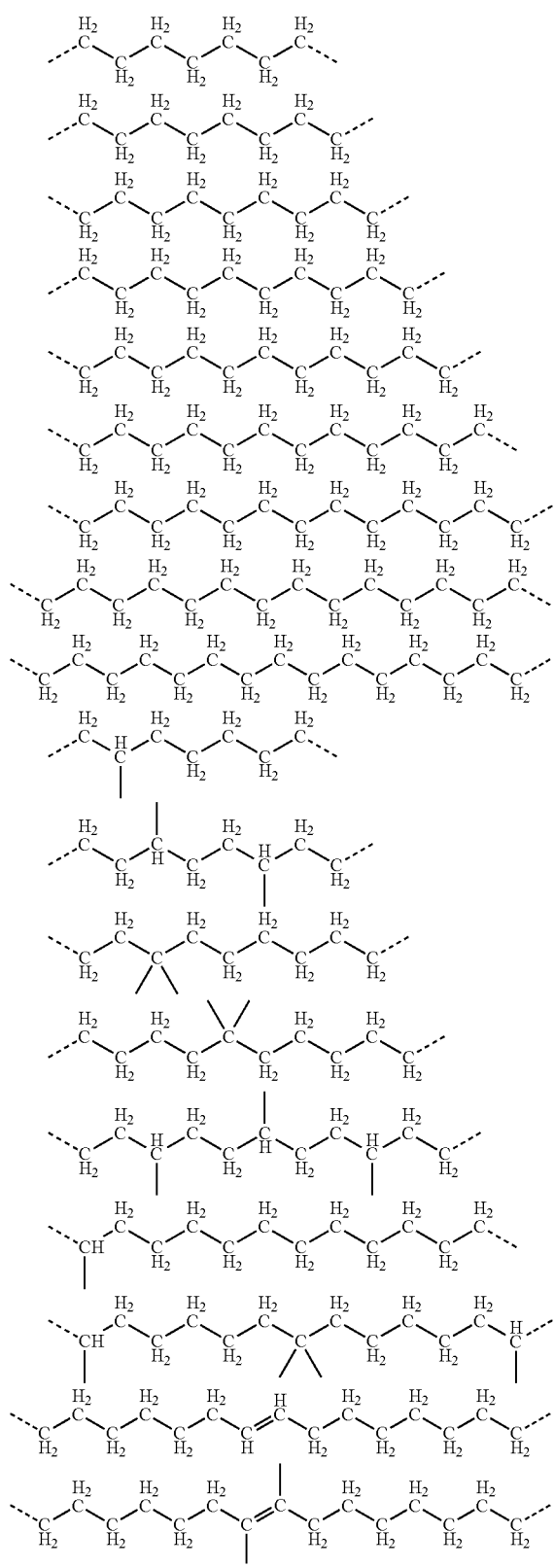

wherein the dashed line represents a bonding arm.

Specific examples of the linear, branched, or cyclic (ka+2)-valent fluorinated hydrocarbon group having 1 to 20 carbon atoms as Az include substances in which a part or all of the hydrogen atoms in the hydrocarbon group described above are substituted with a fluorine atom.

Specific examples of the linear, branched, or cyclic alkyl group having 1 to 6 carbon atoms of $R^2$ and $R^3$ include a methyl group, an ethyl group, a propyl group, an isopropyl group, an n-butyl group, a sec-butyl group, a tert-butyl group, an n-pentyl group, an n-hexyl group, a cyclopropyl group, a cyclobutyl group, a cyclopentyl group, a cyclohexyl group, and the like.

Specific examples of the linear, branched, or cyclic monovalent hydrocarbon group having 1 to 10 carbon atoms optionally substituted with a fluorine atom of Xf include alkyl groups such as a methyl group, an ethyl group, a propyl group, an isopropyl group, an n-butyl group, a sec-butyl group, a tert-butyl group, a cyclopropyl group, or a cyclobutyl group, a trifluoromethyl group, a 2,2,2-trifluoroethyl group, and the like.

Specific examples of the alkoxy group having 1 to 10 carbon atoms optionally substituted with a fluorine atom of Xf include a methoxy group, an ethoxy group, a propoxy group, an isopropoxy group, an n-butoxy group, a sec-butoxy group, a tert-butoxy group, a cyclopropoxy group, a trifluoromethoxy group, a 2,2,2-trifluoroethoxy group, and the like.

Specific examples of the electron-withdrawing group of Xf include a carbonyl group, an alkoxycarbonyl group, a cyano group, a nitro group, a sulfo group, a formyl group, a sulfonic acid ester group, an amide group, —O—C(=O)-G- (G is a sulfur atom or NH), and the like.

Z represents a single bond or an oxygen atom; Specific examples of the aromatic monocyclic or polycyclic ring having 5 to 20 carbon atoms of the ring ZZ include the following substances. As shown below, the ring ZZ may further have a substituent.

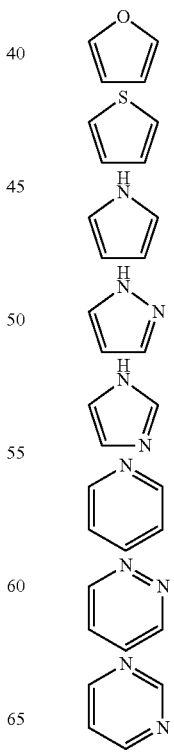

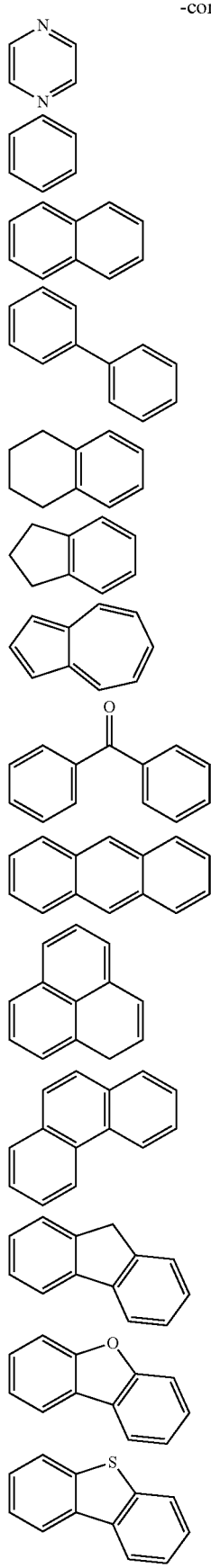
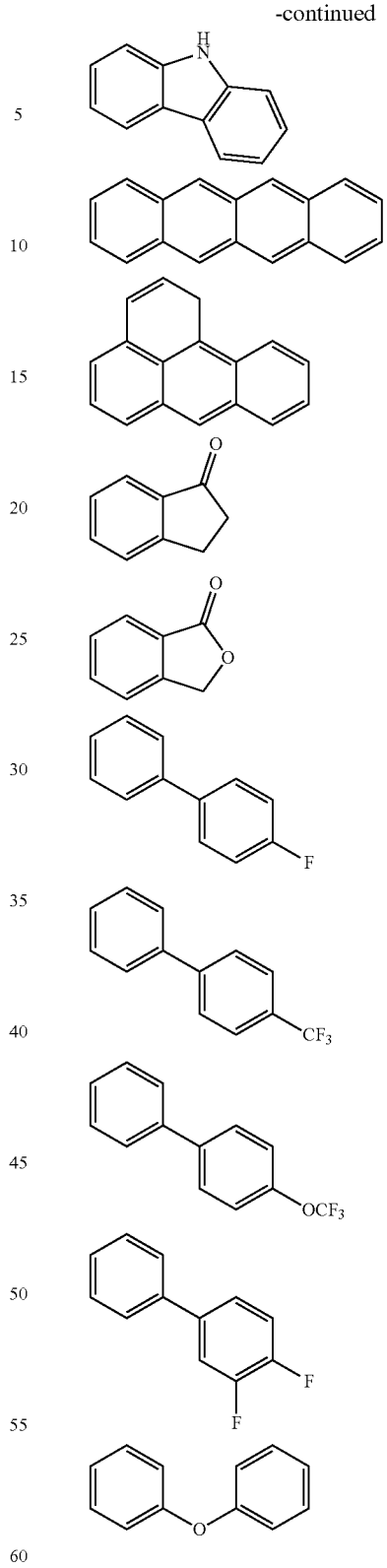
The additive contained in the conductive paste composition of the present invention is a phenol compound represented by the following general formula (1A). The phenol compound represented by the general formula (1A) above is particularly preferably a phenol compound represented by the following general formula (1B).

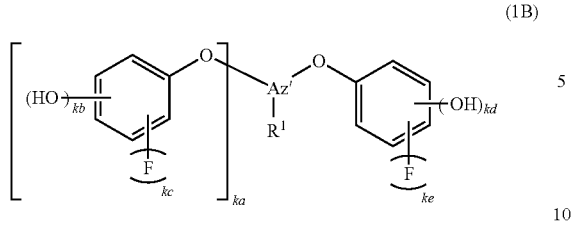
(1B)

Az' represents a linear, branched, or cyclic (ka+2)-valent hydrocarbon group or fluorinated hydrocarbon group having 1 to 19 carbon atoms, and —$CH_2$— constituting the (ka+2)-valent hydrocarbon group is optionally substituted with —O—, —C(=O)— or —Si($R^2R^3$)—; "ka" represents 0 or 1, "kb", "kc", "kd", and "ke" each represent 1 or 2, $R^1$, $R^2$ and $R^3$ are as defined above.

Specific examples of the compounds represented by the general formulae (1A) and (1B) above include the following compounds.

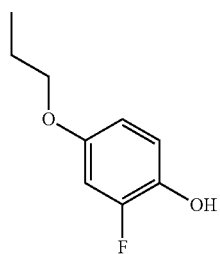

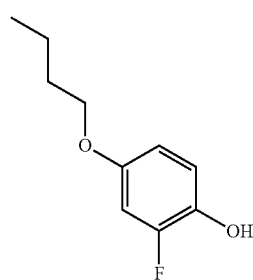

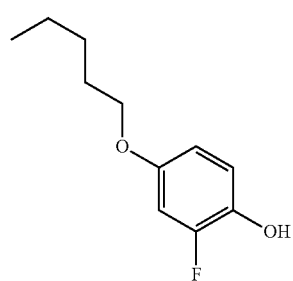

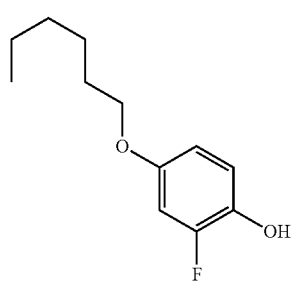

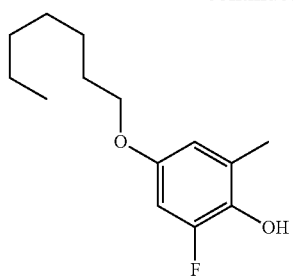

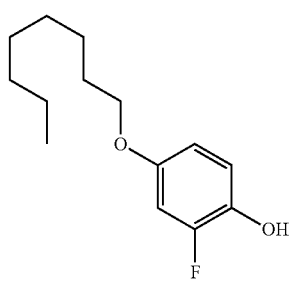

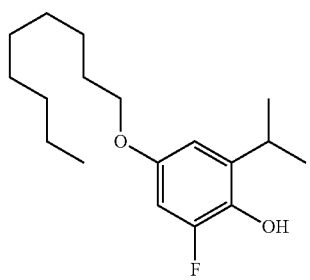

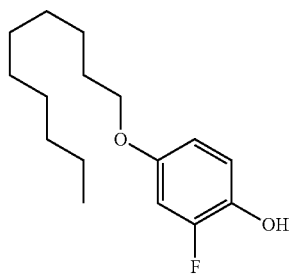

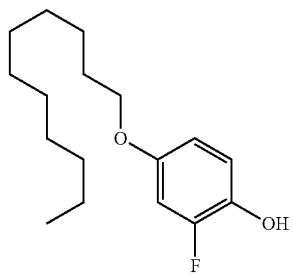

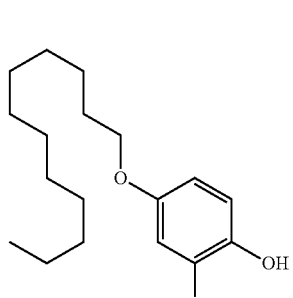

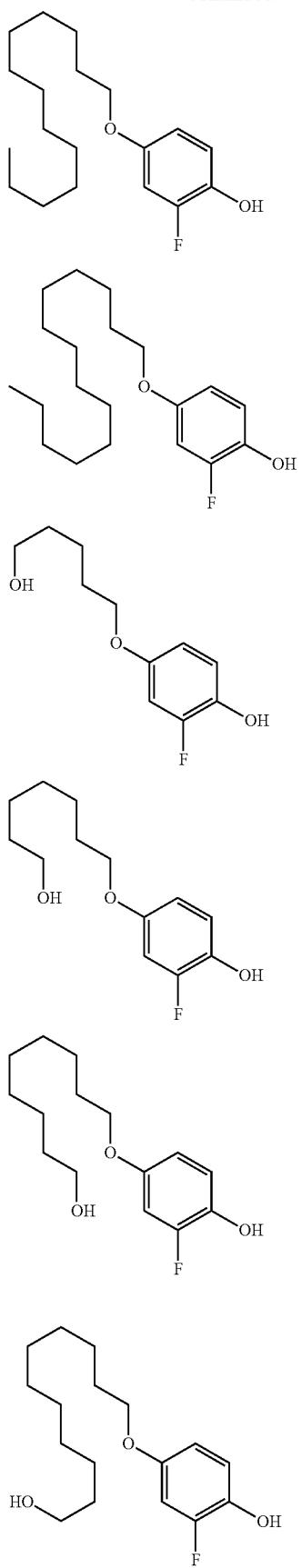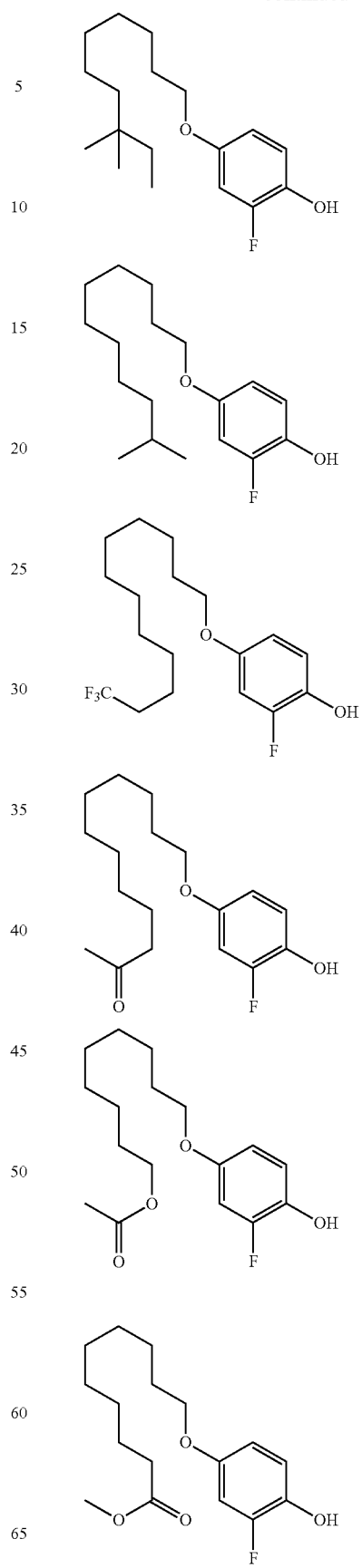

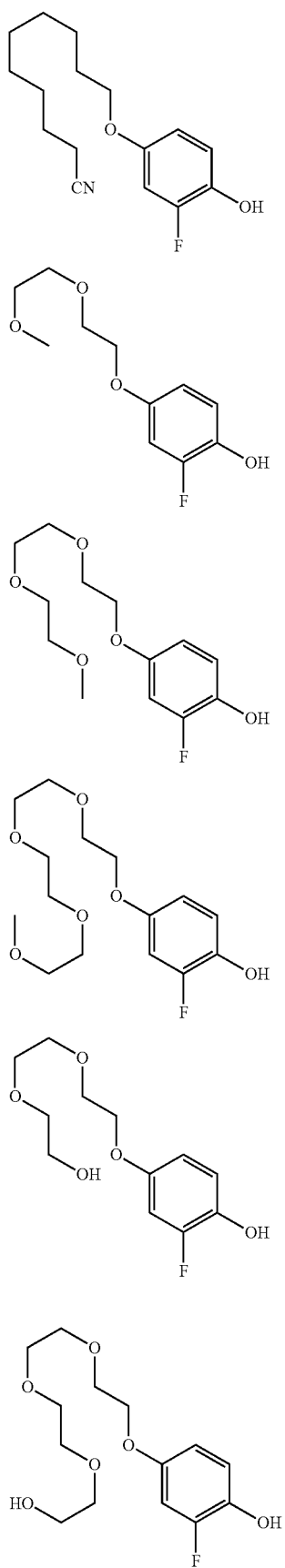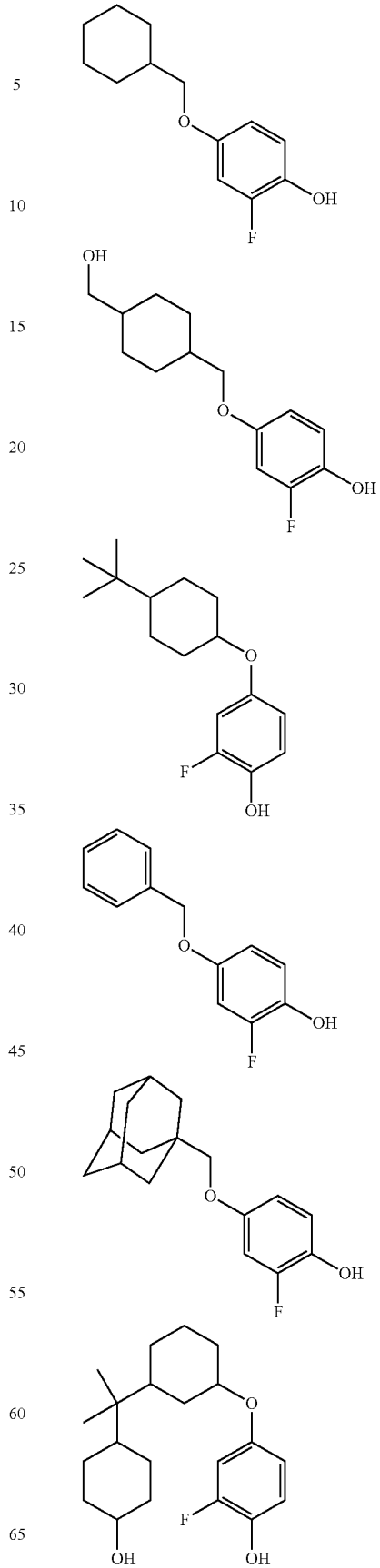

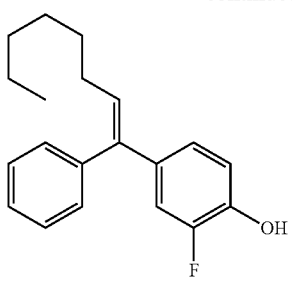
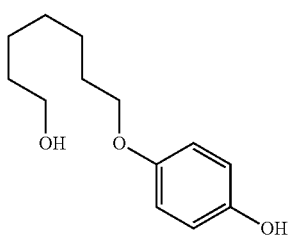
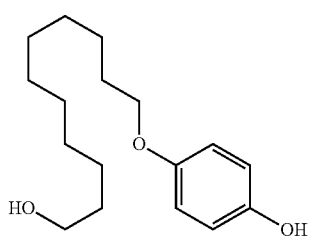
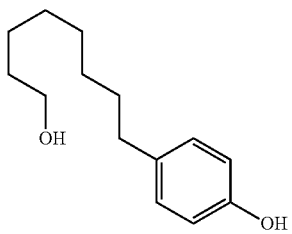
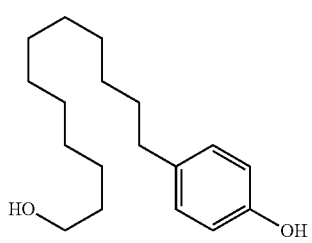
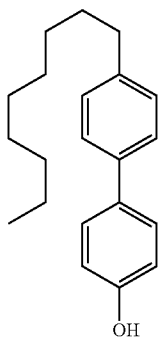
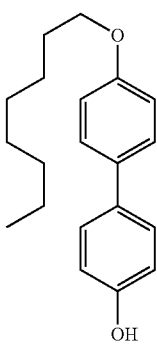
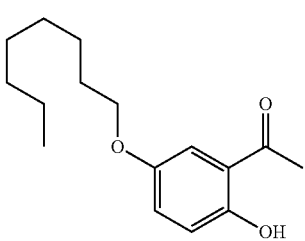
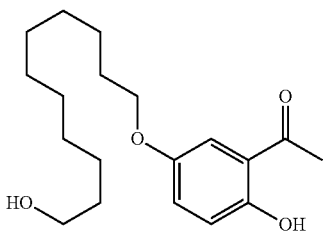
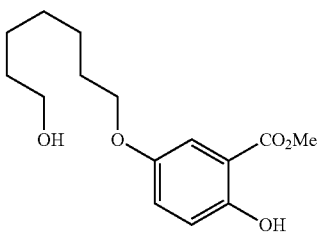
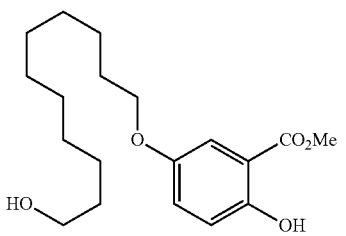
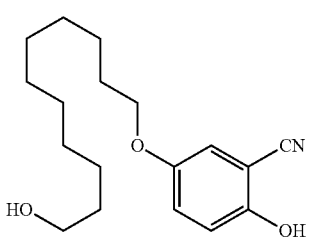

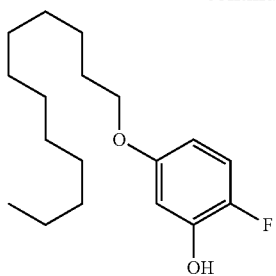
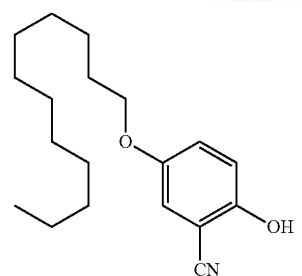
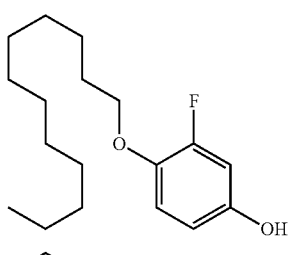
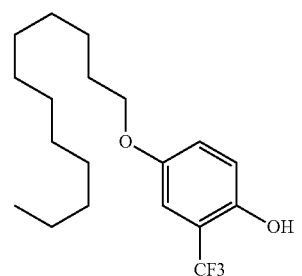
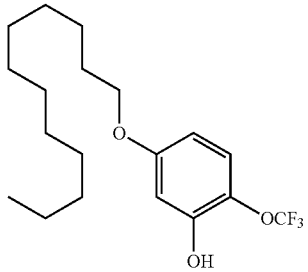
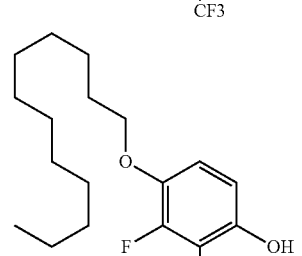
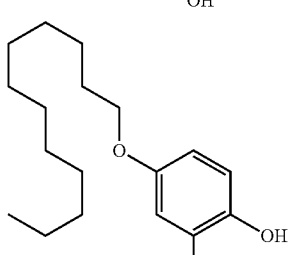
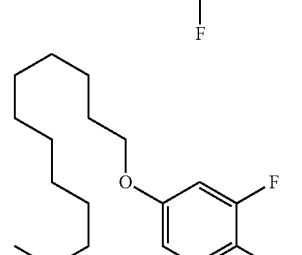
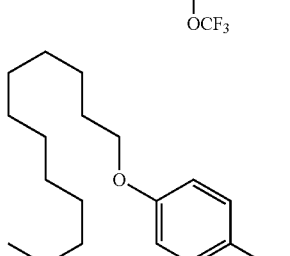
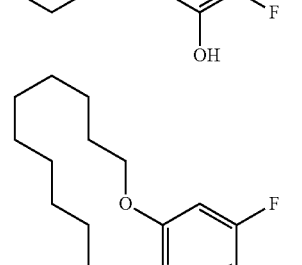
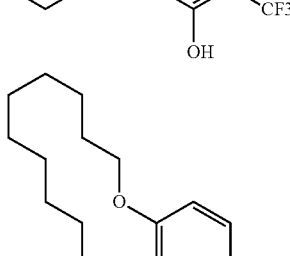
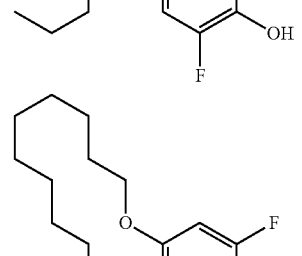
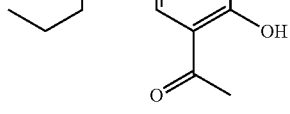
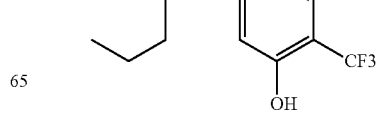

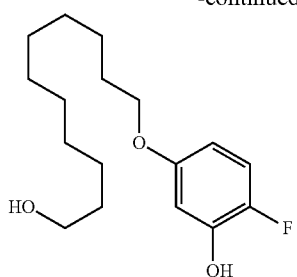
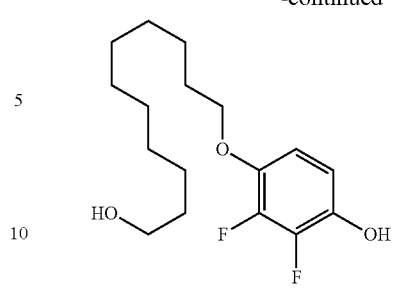
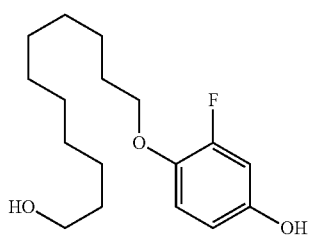
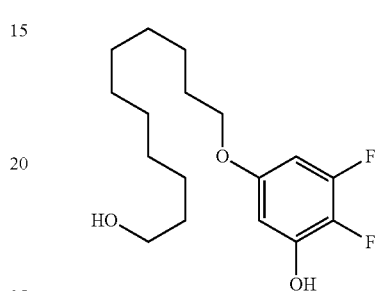
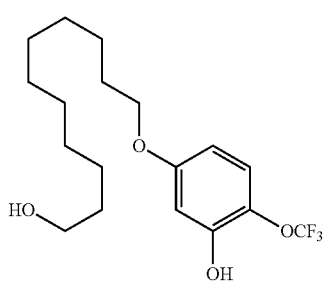
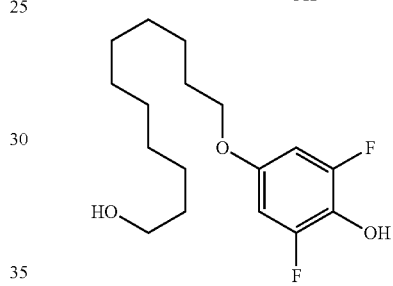
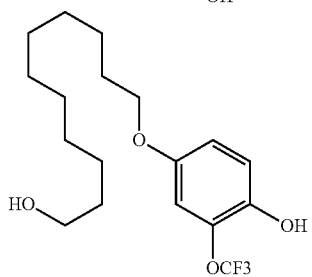
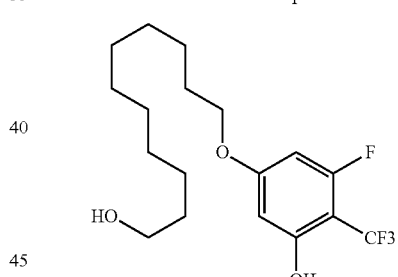
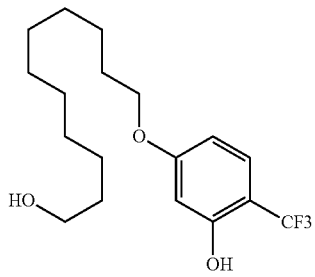
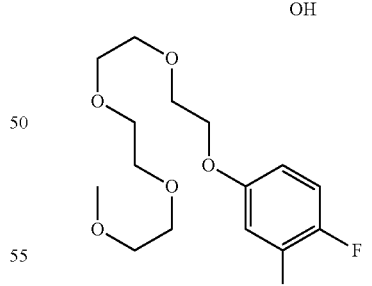
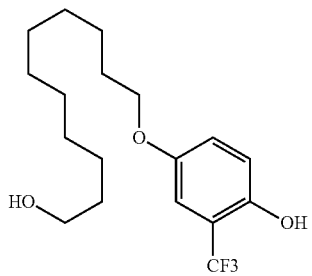
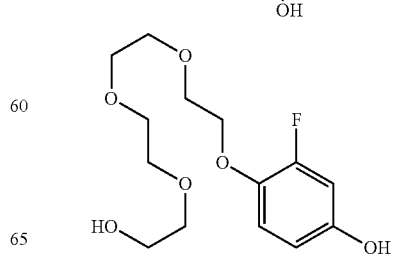

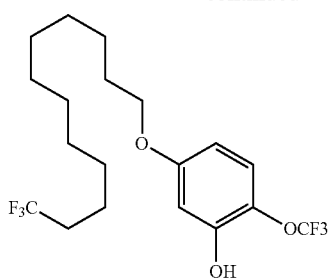
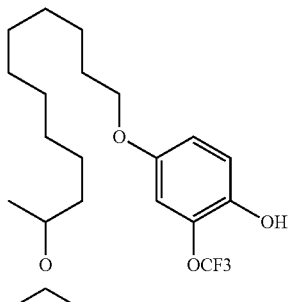
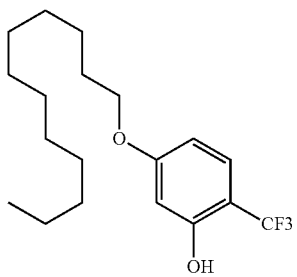
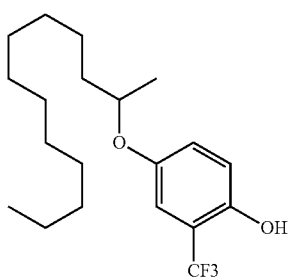
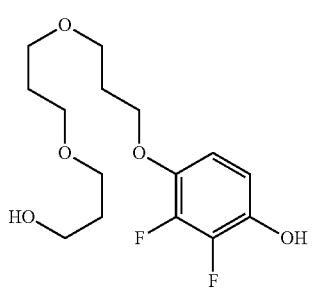
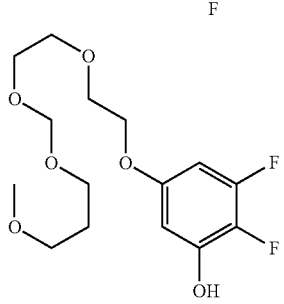
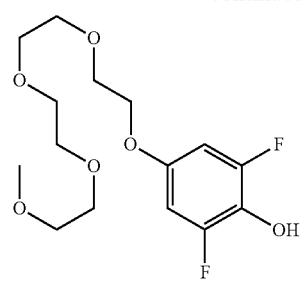
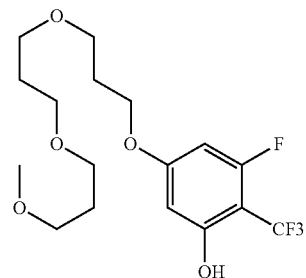
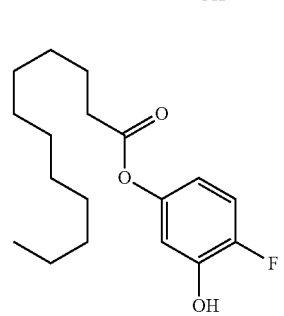
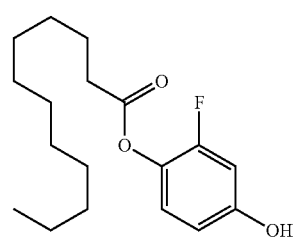
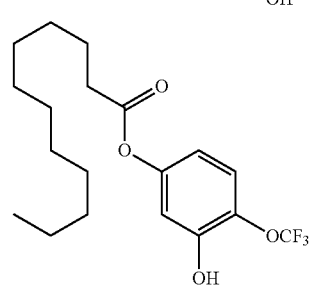
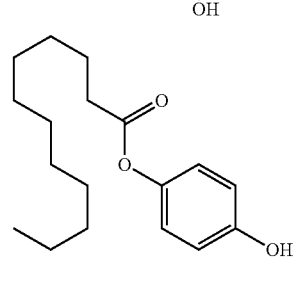

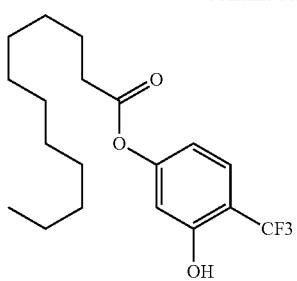
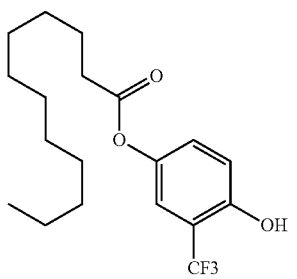
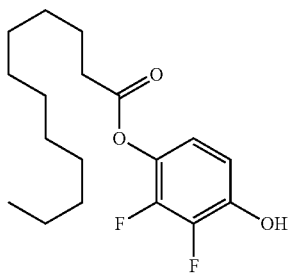
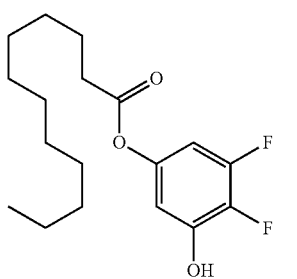
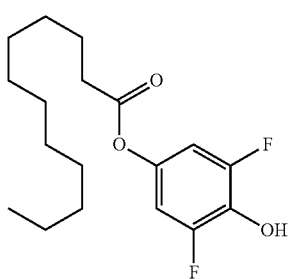
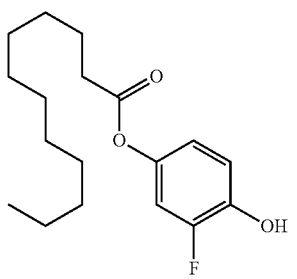
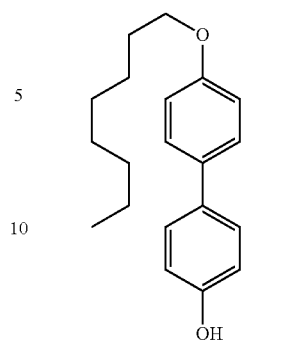
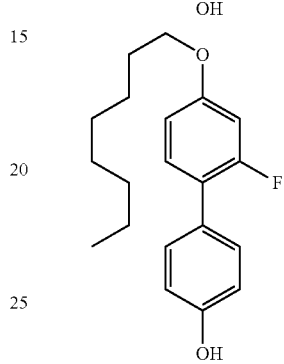
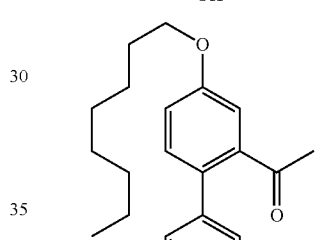
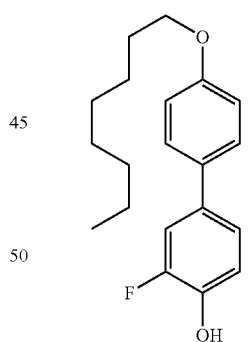
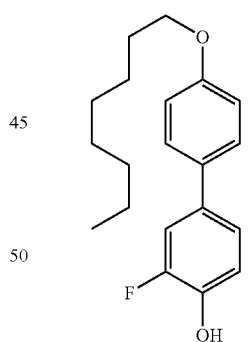

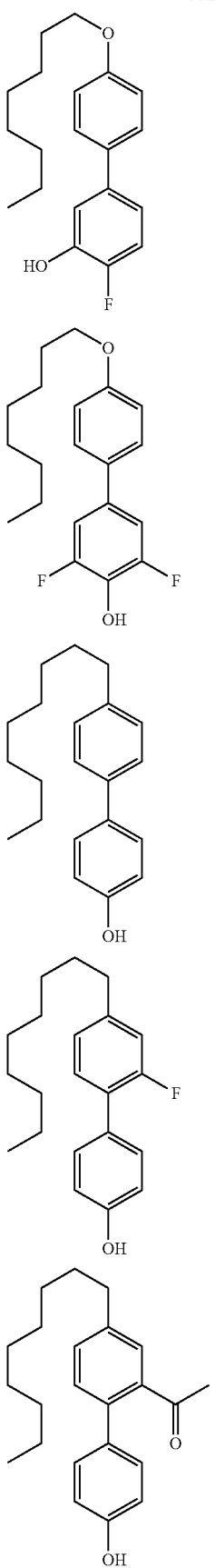
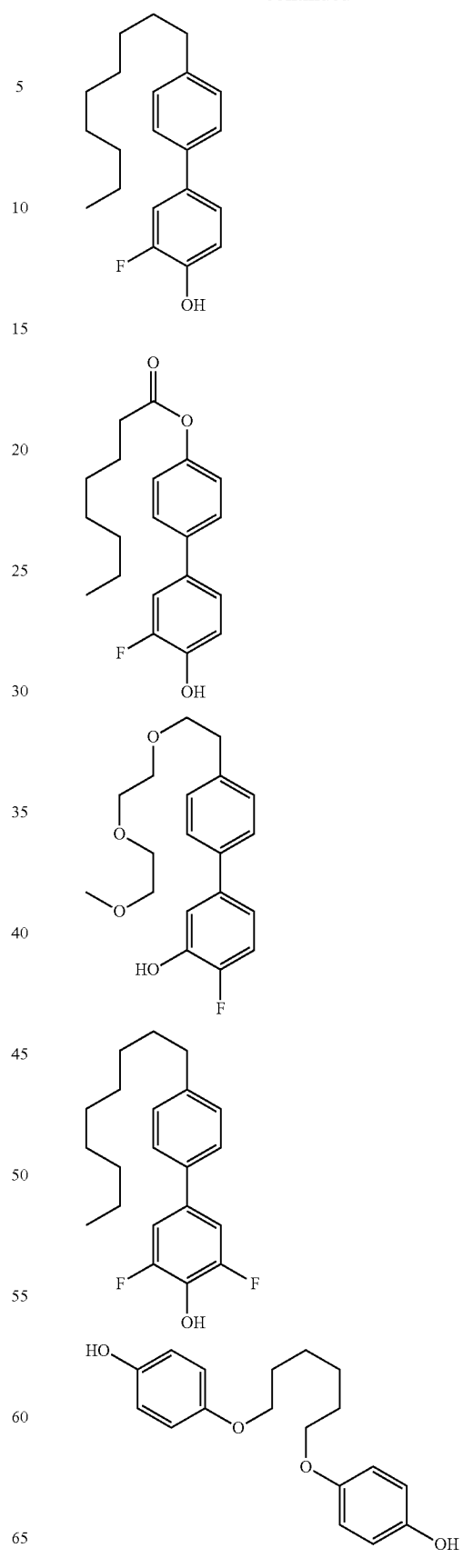

-continued
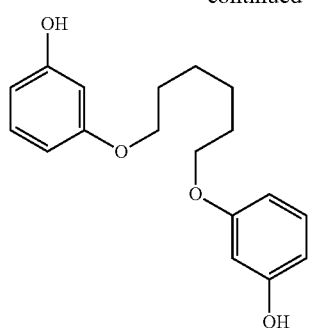
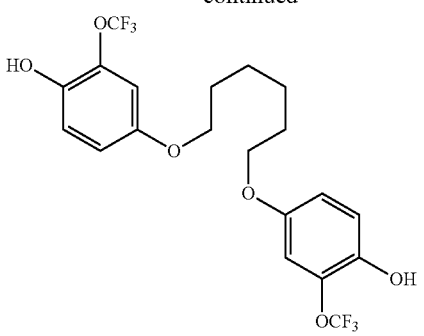
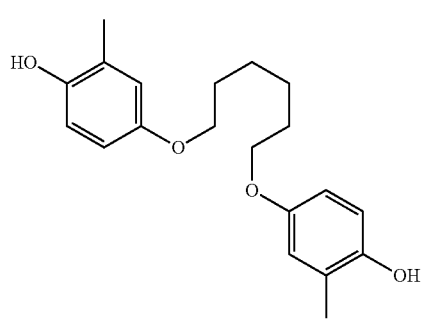
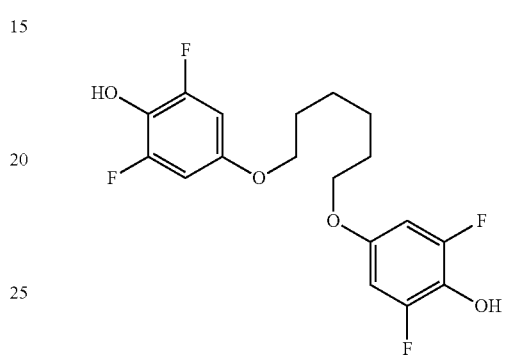
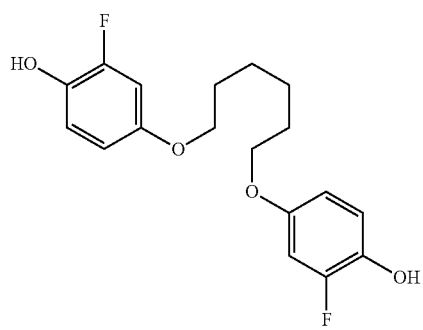
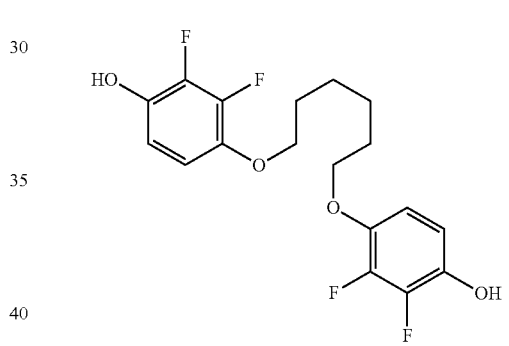
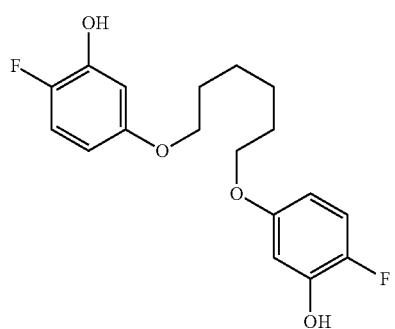
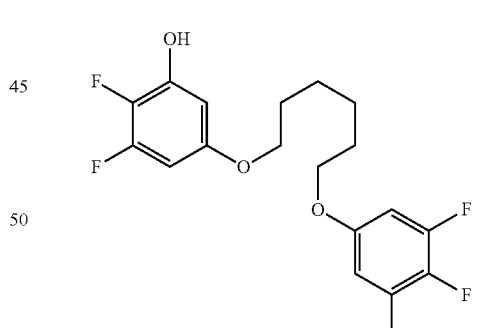
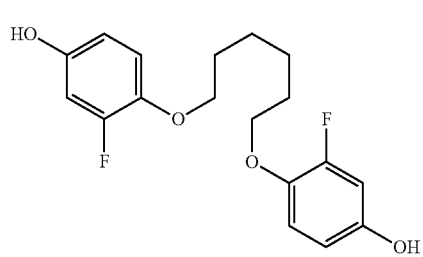
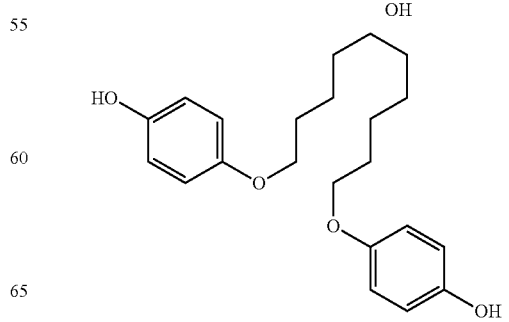

37
-continued
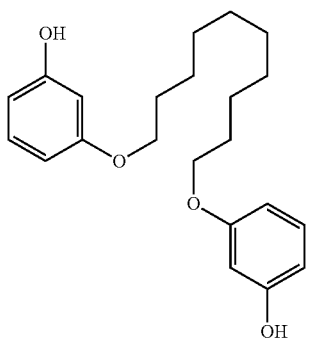
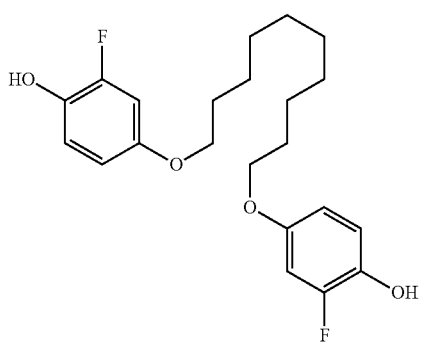
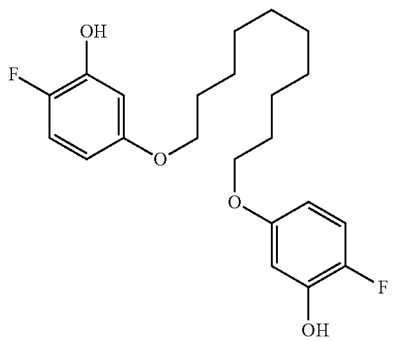
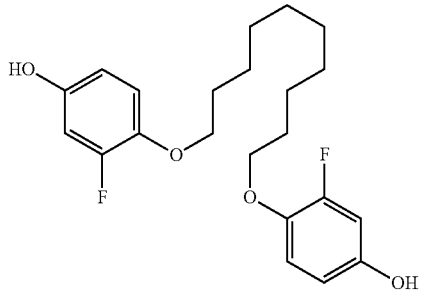
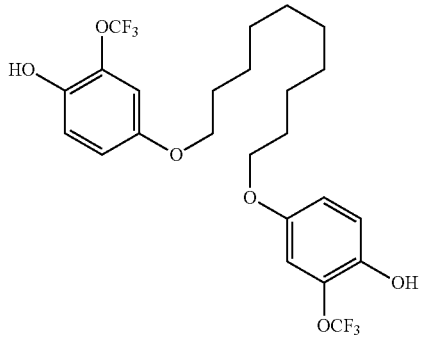
38
-continued
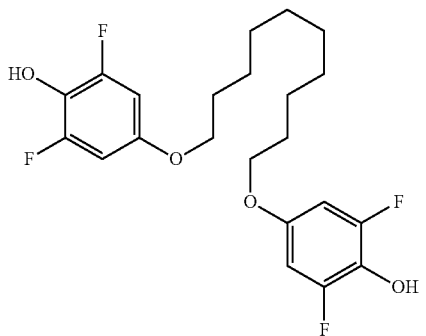
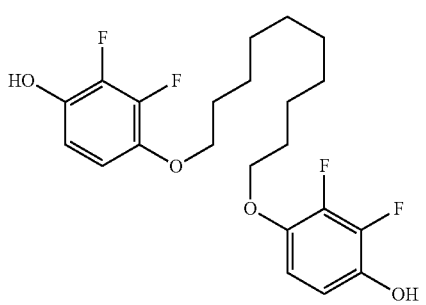
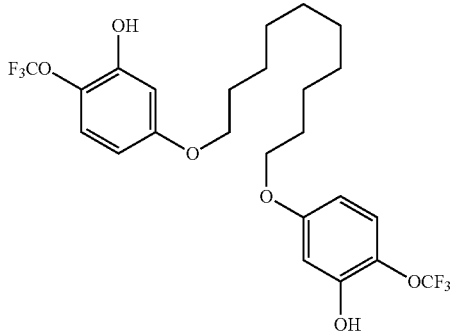
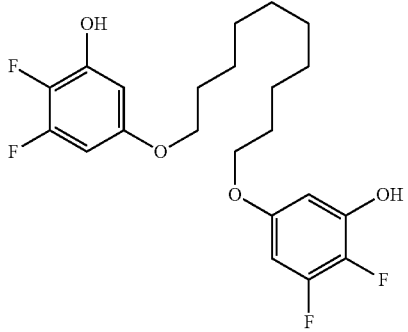
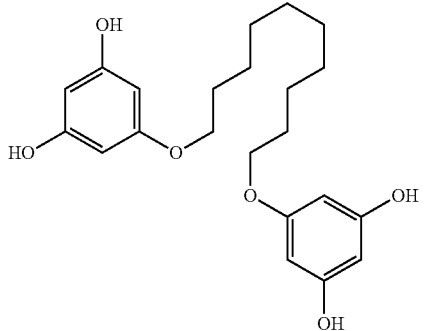

39
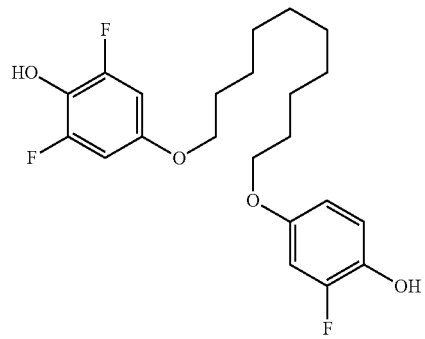
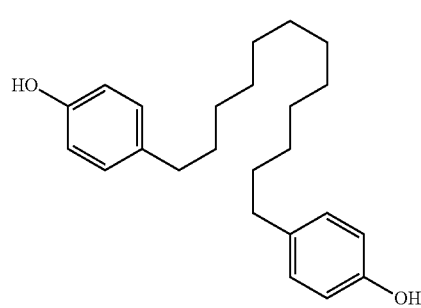
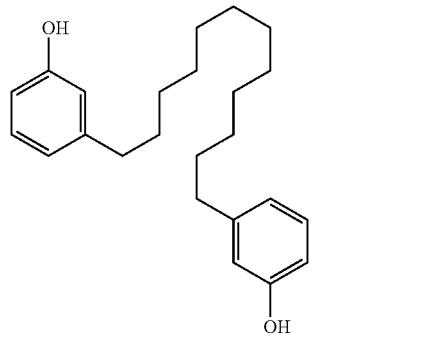
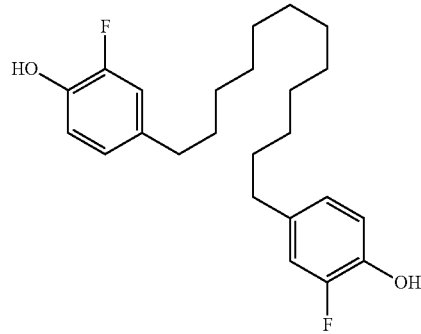
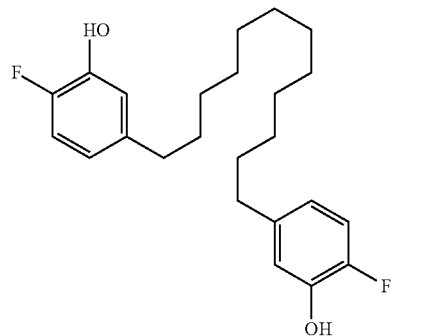
40
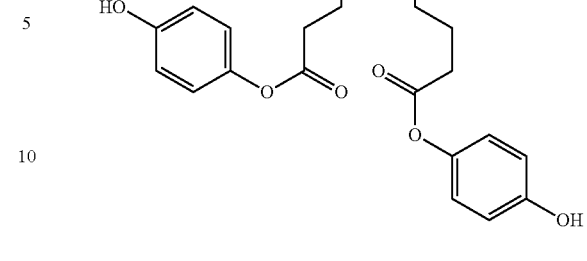
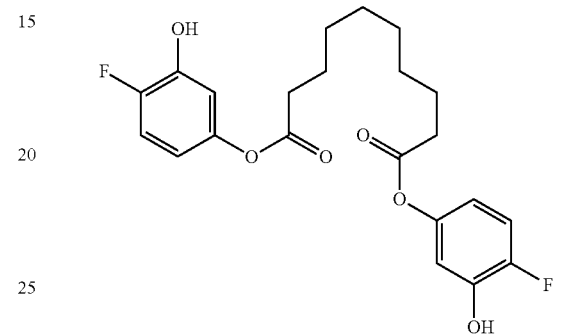
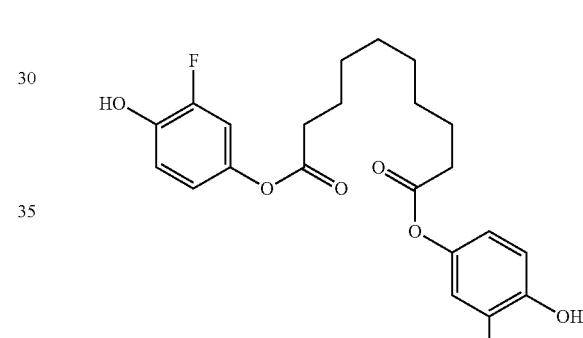
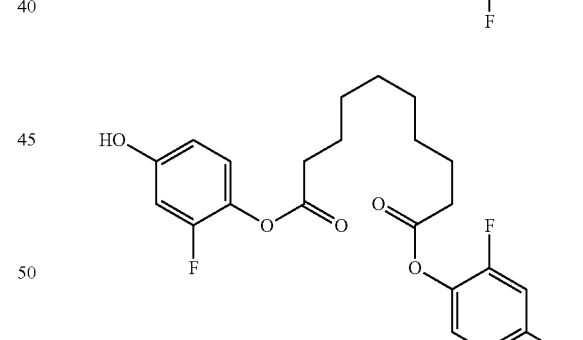
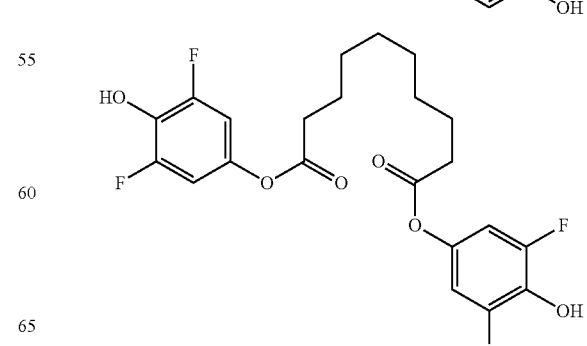

-continued
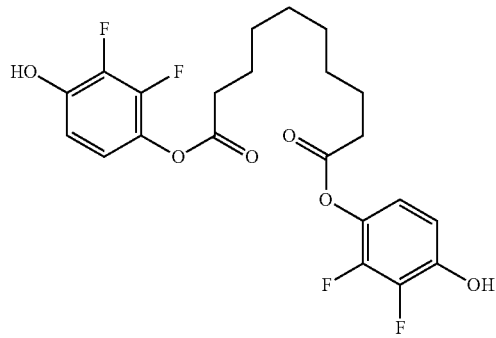
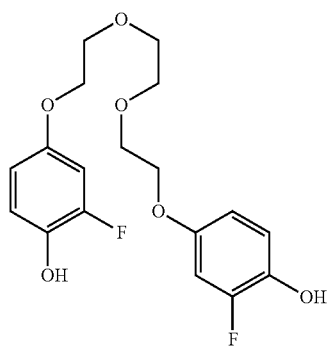
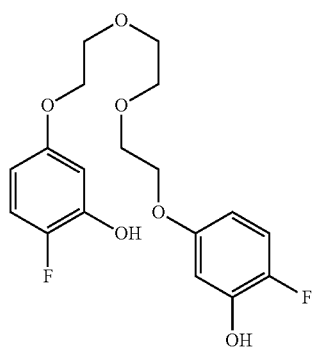
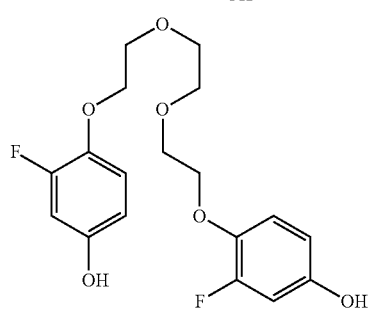
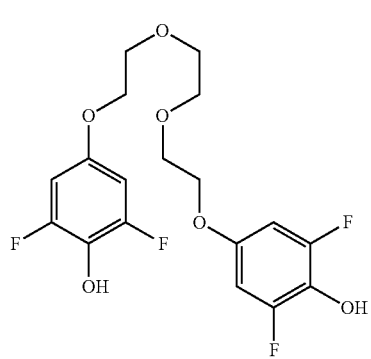
-continued
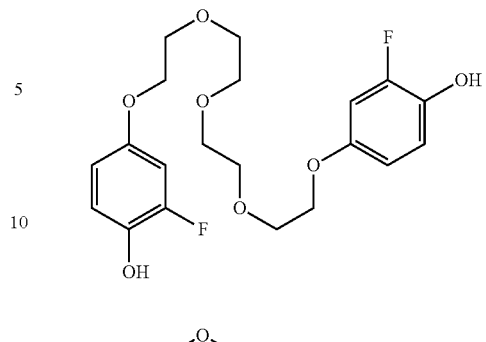
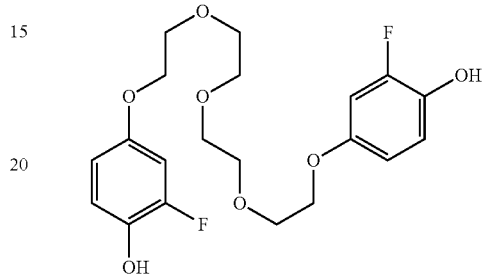
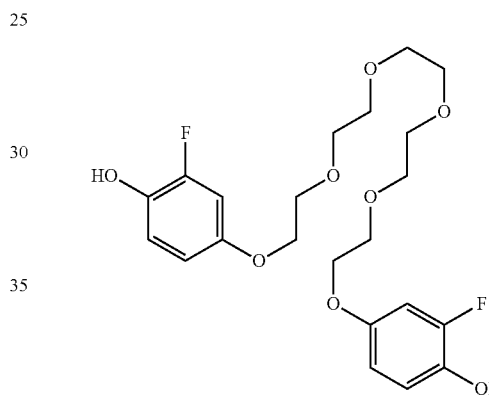
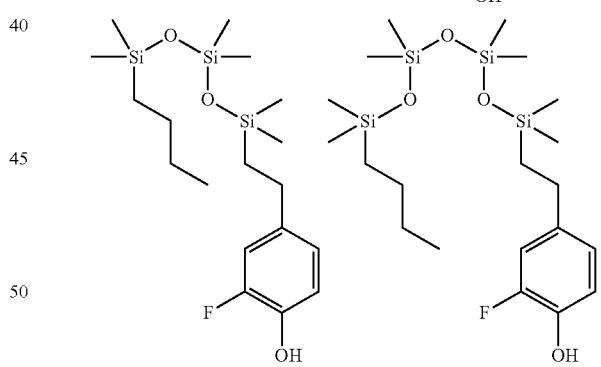
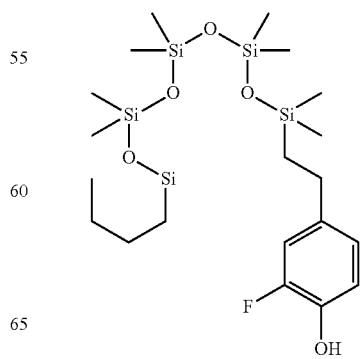

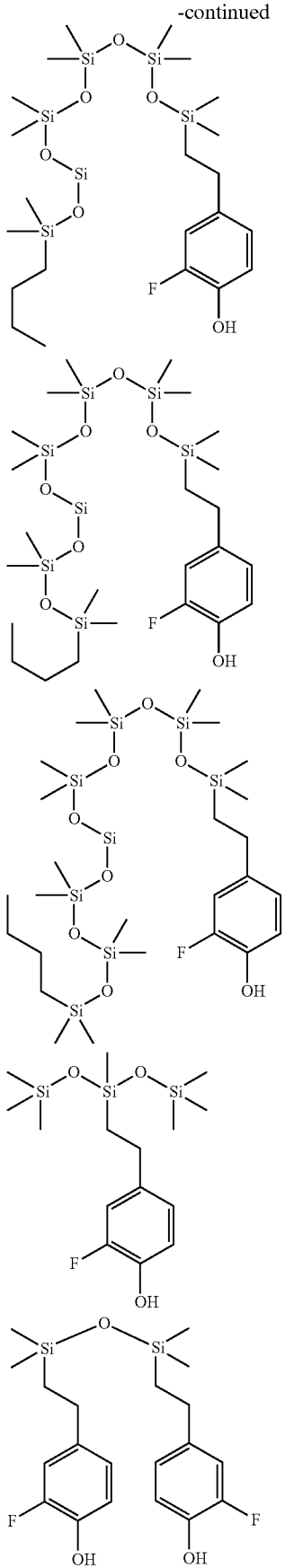
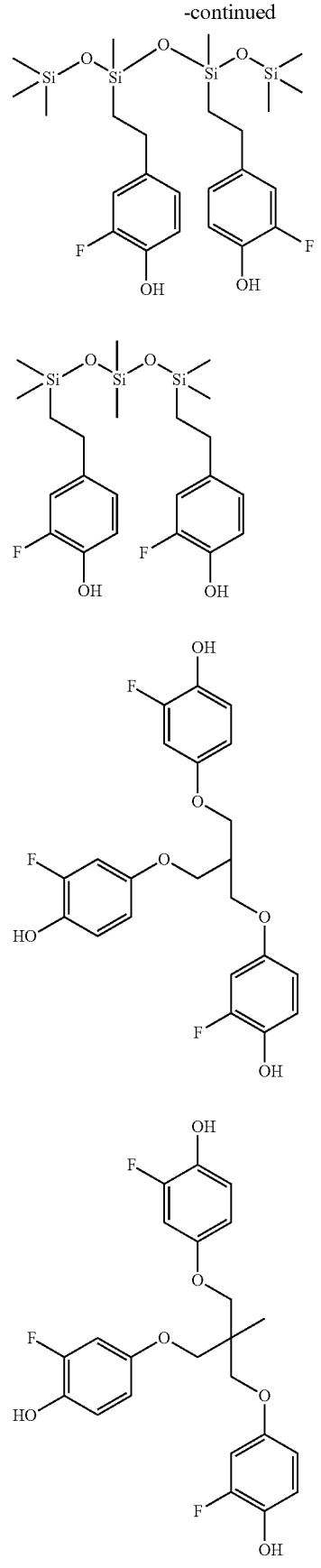

-continued
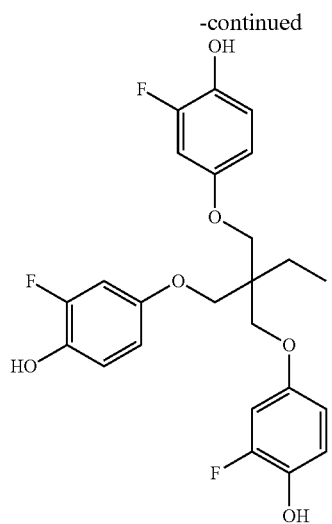
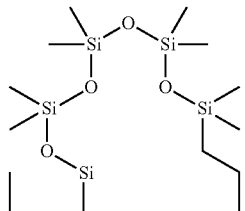
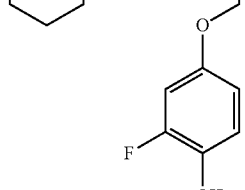
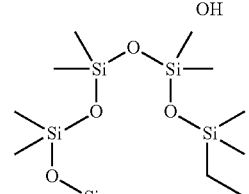
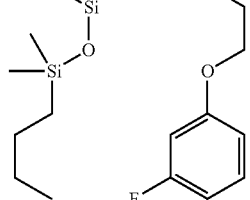
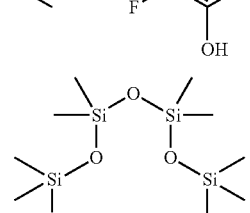
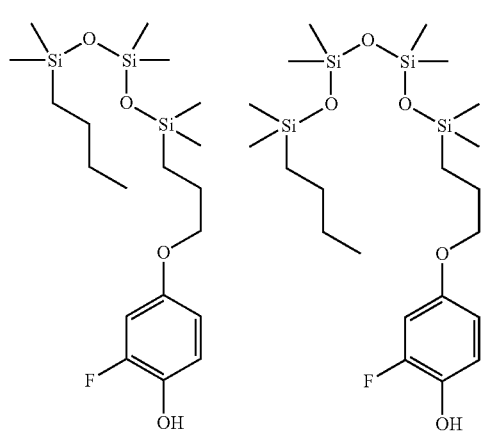

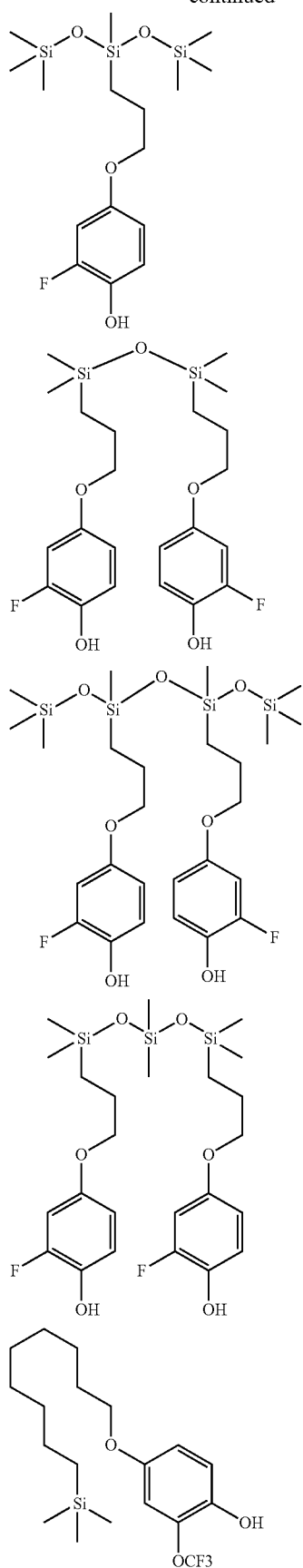
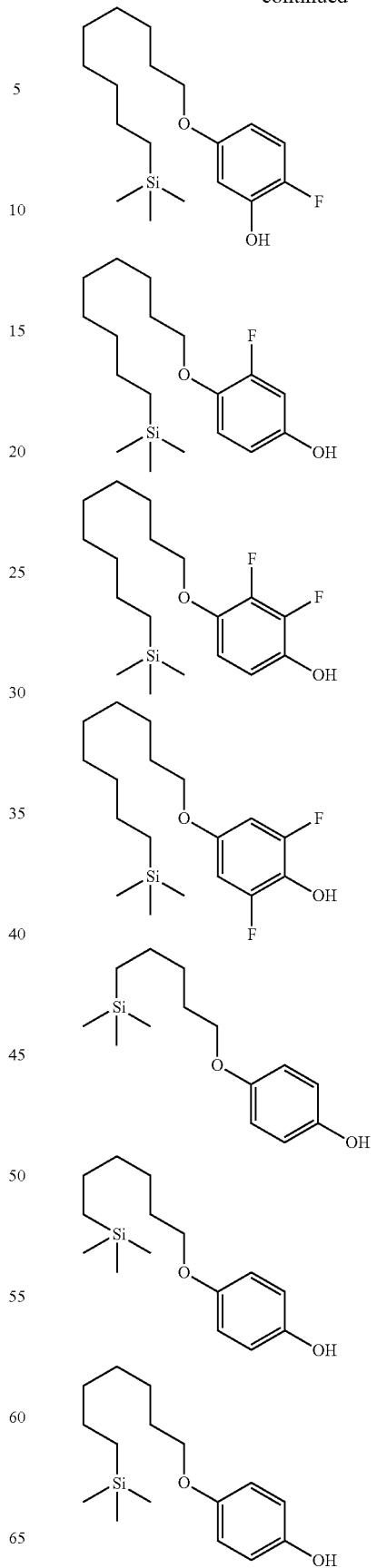

49
-continued

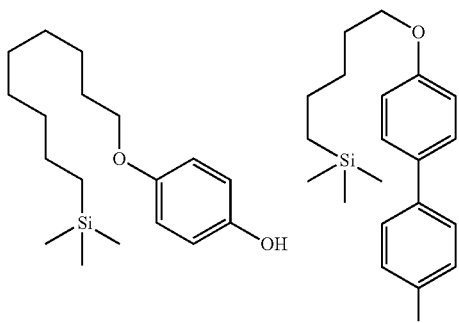

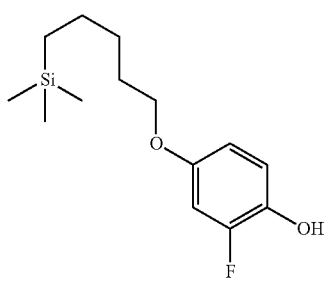

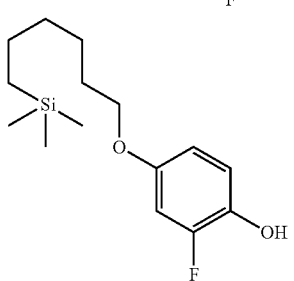

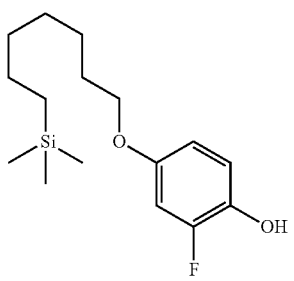

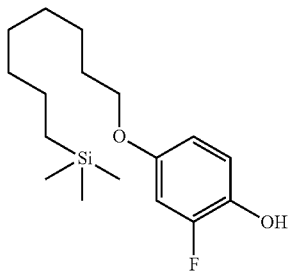

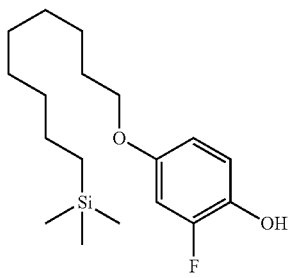

50
-continued

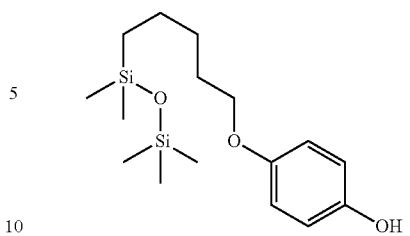

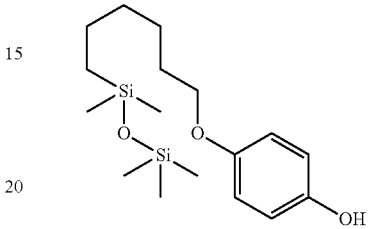

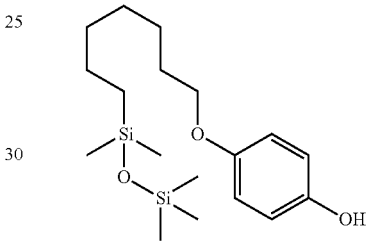

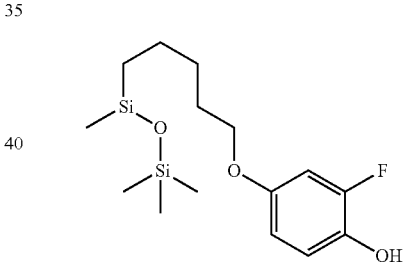

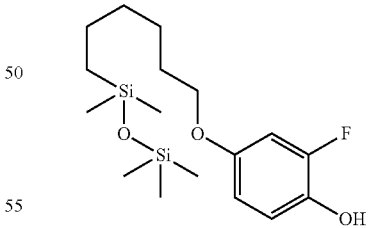

The method for synthesizing the phenol compounds represented by the general formulae (1A) and (1B) above is not particularly limited, and an optimal method can be selected to conduct the synthesis according to the structure. For example, in the case of the general formula (1B) in which "kb" and "kc" are 1, the synthesis can be performed by the steps (i) to (v) shown in the following reaction formula.

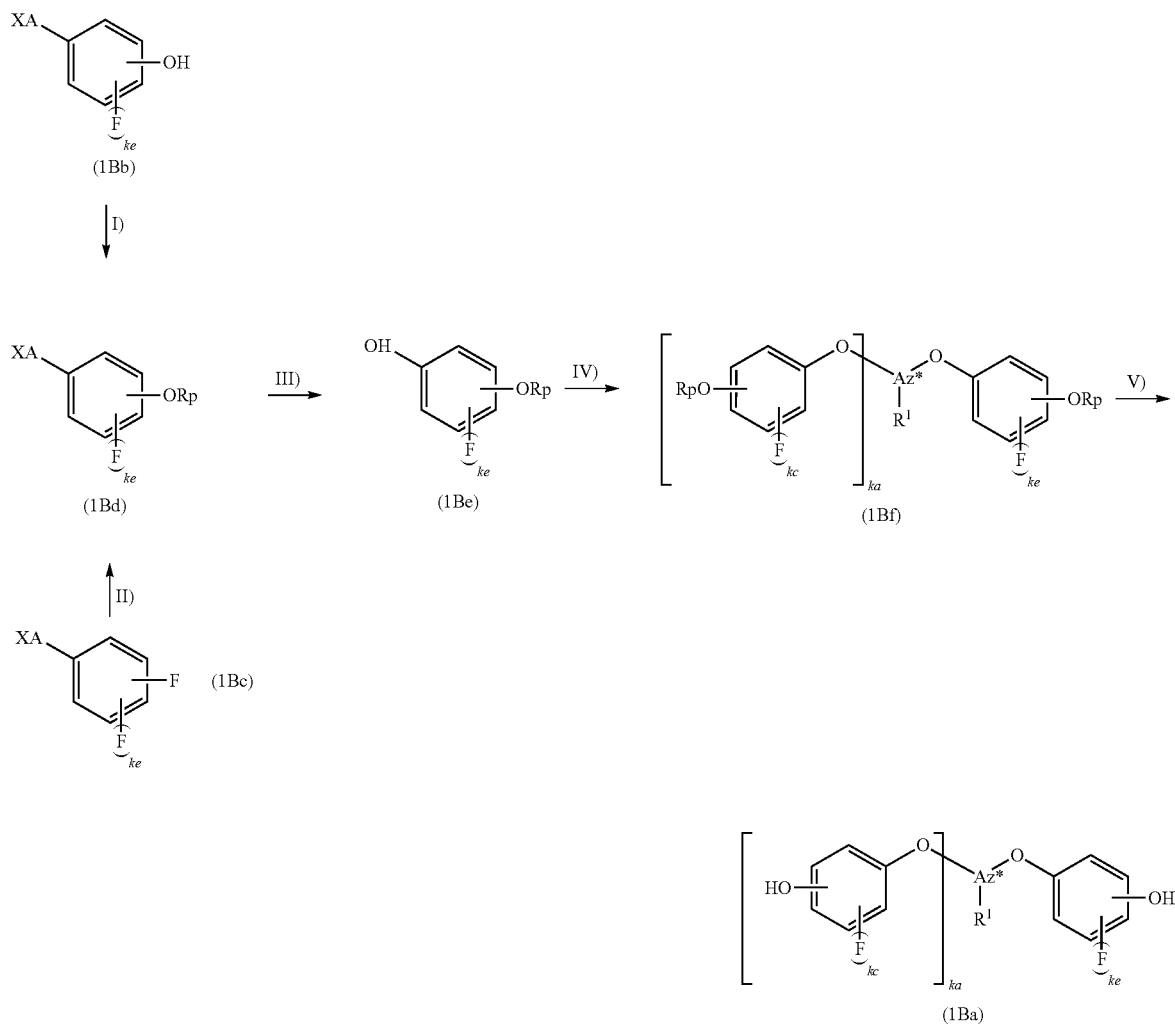

wherein $R^1$, $Az'$, ka, kc and ke are as defined above; Rp represents an acid labile group; and XA represents a halogen atom.

The step (i) is a step of protecting a halogenated phenol compound (1Bb) to give an intermediate halogenated aryl compound (1Bd).

The reaction of the step (i) advances easily under known conditions. However, for example, when Rp is a tertiary alkyl group such as a t-butyl group, t-amyl group, methylcyclopentyl group, ethylcyclopentyl group, methylcyclohexyl group, ethylcyclohexyl group, methyladamantyl group or an ethyladamantyl group, the reaction is preferably carried out at a reaction temperature of −20° C. to 50° C. without a solvent or in a solvent such as toluene or hexane using the halogenated phenol compound (1Bb) and olefins corresponding to Rp such as isobutene or isoamylene in the presence of an acid catalyst. Examples of the acid catalyst to be used include inorganic acids such as hydrochloric acid, sulfuric acid, nitric acid and perchloric acid, and organic acids such as methanesulfonic acid, trifluoromethanesulfonic acid, p-toluenesulfonic acid and benzenesulfonic acid.

The step (ii) is a step of subjecting a fluorobenzene compound (1Bc) to a nucleophilic substitution reaction to give the intermediate halogenated aryl compound (1Bd).

The reaction of the step (ii) advances easily under known conditions. However, for example, when Rp is a tertiary alkyl group such as a t-butyl group, t-amyl group, methylcyclopentyl group, ethylcyclopentyl group, methylcyclohexyl group, ethylcyclohexyl group, methyladamantyl group or an ethyladamantyl group, the reaction is preferably carried out at a reaction temperature of 10° C. to 80° C. in a solvent such as tetrahydrofuran or N-methyl-2-pyrrolidone using the fluorobenzene compound (1Bc) and alcohol corresponding to Rp such as t-butyl alcohol or t-amyl alcohol, or corresponding alkoxides such as potassium t-butoxide in the presence of a base. Examples of the base to be used include metal hydrides such as borane, alkylborane, sodium hydride, lithium hydride, potassium hydride and calcium hydride; alkyl metal compounds such as trityllithium, tritylsodium, tritylpotassium, methyllithium, phenyllithium, n-butyllithium, sec-butyllithium, tert-butyllithium and ethylmagnesium bromide; metal alkoxides such as sodium methoxide, sodium ethoxide, lithium methoxide, lithium ethoxide, lithium tert-butoxide and potassium tert-butoxide, and the like.

The step (iii) is a step of oxidizing the halogenated aryl compound (1Bd) to give an intermediate phenol compound (1Be).

The reaction easily advances by a known method, and for example, a method of the following reaction scheme may be exemplified.

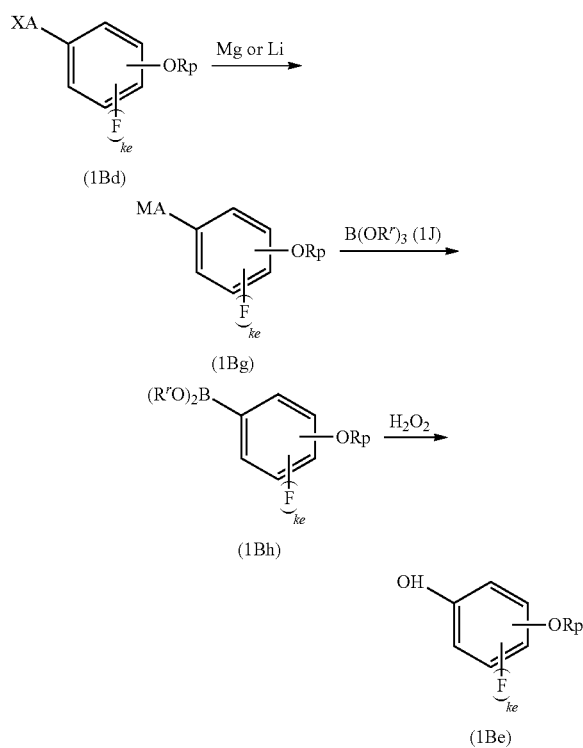

(1Bd)

(1Bg)

(1Bh)

(1Be)

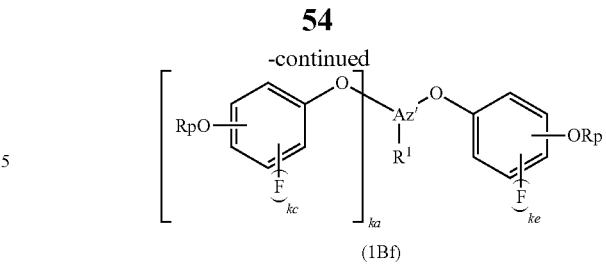

(1Bf)

wherein Rp, ka, ke, and Az' are as defined above; $T^1$ each independently represents a hydroxyl group, a halogen atom, an alkanesulfonyloxy group, or an arenesulfonyloxy group.

Examples of the etherification method include a method of etherifying the intermediate phenol compound (1Be) and a leaving group-containing compound (1Bi) by treating them with a base.

Examples of halogen atom of $T^1$ include a chlorine atom, a bromine atom, and an iodine atom. Examples of alkanesulfonyloxy group and arenesulfonyloxy group of $T^1$ include methanesulfonyloxy, trifluoromethanesulfonyloxy, benzenesulfonyloxy, and p-toluenesulfonyloxy group.

Specific examples of the base to be used include metal alkoxides such as sodium methoxide, sodium ethoxide, lithium methoxide, lithium ethoxide, lithium tert-butoxide, and potassium tert-butoxide; organic amines such as pyridine, triethylamine, N,N-dimethylaniline, and 4-dimethylaminopyridine; inorganic hydroxides such as sodium hydroxide, lithium hydroxide, potassium hydroxide, barium hydroxide, and tetra-n-butylammonium hydroxide; inorganic carbonates such as sodium carbonate, sodium bicarbonate, lithium carbonate, and potassium carbonate; metal hydrides such as borane, alkylborane, sodium hydride, lithium hydride, potassium hydride, and calcium hydride; alkyl metal compounds such as trityllithium, tritylsodium, tritylpotassium, methyllithium, phenyllithium, sec-butyllithium, tert-butyllithium, methylmagnesium chloride, ethylmagnesium chloride, and ethylmagnesium bromide; and metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, and bromomagnesium diisopropylamide, and the like. The amount of the base to be used is preferably 0.9 to 10 moles, particularly preferably 1.0 to 5.0 moles, per mole of the intermediate phenol compound (1Be).

Examples of the solvents include water; ethers such as tetrahydrofuran, diethylether, di-n-butylether and 1,4-dioxane; hydrocarbons such as n-hexane, n-heptane, benzene, toluene, xylene and cumene; alcohols such as methanol, ethanol, isopropyl alcohol and tert-butyl alcohol; aprotic polar solvents such as dimethyl sulfoxide (DMSO) and N,N-dimethylformamide (DMF); and chlorine-based organic solvents such as methylene chloride, chloroform and carbon tetrachloride, which may be used individually or in combination depending on the reaction conditions. The bases listed above may be used themselves as a solvent.

Although the reaction temperature and time vary depending on the reagents and conditions, for example, when the reaction is performed using a bromine atom as $T^1$ and potassium carbonate as the base, the reaction temperature is preferably from room temperature to 120° C., more preferably from 30° C. to 90° C., from the viewpoint of rapid completion of the reaction. The reaction time is preferably determined in view of completing the reaction by monitorwherein Rp, ke and XA are as defined above; MA represents Li, MgCl, MgBr, MgI; $R^r$ is a linear, branched, or cyclic monovalent hydrocarbon group having 1 to 6 carbon atoms.

First, an organometallic reagent (1Bg) is prepared from the halogenated aryl compound (1Bd) and Li or Mg in a solvent such as tetrahydrofuran, diethyl ether, or the like. Subsequently, the reagent is reacted with a boronic acid ester compound (1J) to induce an arylboronate derivative (1Bh), and finally, an oxidant such as hydrogen peroxide, performic acid, peracetic acid, or m-chloroperbenzoic acid is used to obtain an intermediate phenol compound (1Be). In this step, the reaction can be usually advanced in one pot without a purification step.

The step (iv) is a step of etherifying the intermediate phenol compound (1Be) to give an aryl ether compound (1Bf).

The reaction easily advances by a known method, and for example, a method of the following reaction scheme may be exemplified.

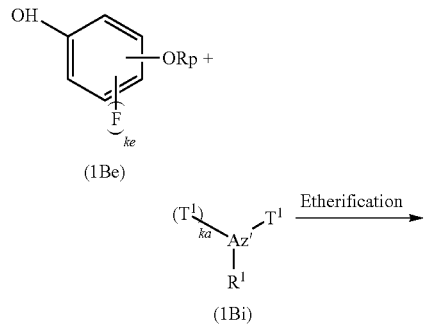

(1Be)

(1Bi)

ing the reaction by gas chromatography (GC) or silica gel thin layer chromatography (TLC) from the viewpoint of yield. The reaction time is usually about 1 to 60 hours. From the reaction mixture, an aryl ether compound (1Bf) can be obtained by ordinary aqueous work-up, and the aryl ether compound can be, if necessary, purified by a standard method such as distillation, chromatography, and the like.

The step (v) is a step of subjecting the aryl ether compound (1Bf) to a deprotection reaction to give the phenol compound of the present invention.

Examples of the solvents include hydrocarbons such as toluene, xylene, hexane, and heptane; chlorine-based solvents such as methylene chloride, chloroform, and dichloroethane; ethers such as diethylether, tetrahydrofuran, and dibutylether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, which may be used individually or in combination of two or more kinds. The reaction can also be performed without a solvent.

The deprotection reaction can be performed in the presence of an acid. Examples of the acid include inorganic acids such as hydrochloric acid, sulfuric acid, nitric acid, and perchloric acid; organic acids such as methanesulfonic acid, trifluoromethanesulfonic acid, p-toluenesulfonic acid, and benzenesulfonic acid; and Lewis acids such as boron trifluoride, trimethylsilyl triflate, aluminum chloride, magnesium chloride, iron chloride, zinc chloride, and titanium chloride; and the like. The amount of the acid to be used is preferably 0.001 to 5 moles, particularly preferably 0.01 to 0.5 moles, per mole of the aryl ether compound (1Bf). When the amount of the acid is 0.001 mole or more, the reaction rate does not decrease, and there is no disadvantage in terms of cost due to an increase in the reaction time. When the amount of the acid is 5 moles or less, a side reaction due to strong acidity does not occur, and the yield does not decrease. In order to reduce the acidity, a base, for example, amines such as ammonia, triethylamine, pyridine, lutidine, collidine, and N,N-dimethylaniline and the like may be added.

In the deprotection reaction, an appropriate reaction temperature can be selected depending on the reaction conditions. Since the reaction may not be advanced under low temperature conditions, the reaction temperature is usually preferably 40° C. to 120° C. In addition, the reaction time is preferably determined by tracking the progress of the reaction by thin layer chromatography, gas chromatography or the like in order to improve the yield. The reaction time is usually about 2 hours to 1 day. The reaction can be performed by diluting the aryl ether compound (1Bf) with a solvent, adding an acid thereto, followed by heating and stirring. After completion of the reaction, a phenol compound (1Ba) can be obtained by ordinary aqueous work-up, and the phenol compound can be, if necessary, purified by a standard method such as distillation, recrystallization, chromatography, or the like.

Conductive Paste Composition

The conductive paste composition of the present invention is characterized by comprising (A) a conductive filler, (B) a phenol compound, (C) an elastomer resin, and (D) a solvent, wherein the phenol compound as the component (B) is a phenol compound represented by the following general formula (1A) or (1B).

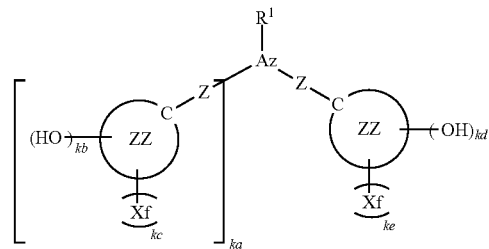

(1A)

wherein $R^1$ represents a hydrogen atom, a halogen atom, a cyano group, or a hydroxyl group, Az represents a linear, branched, or cyclic (ka+2)-valent hydrocarbon group or fluorinated hydrocarbon group having 1 to 20 carbon atoms, and —$CH_2$— constituting the (ka+2)-valent hydrocarbon group is optionally substituted with —O—, —C(=O)— or —Si($R^2R^3$)—, each of $R^2$ and $R_3$ is a linear, branched, or cyclic alkyl group having 1 to 6 carbon atoms, or a phenyl group, each Xf independently represents a hydrogen atom, a halogen atom, a linear, branched, or cyclic monovalent hydrocarbon group having 1 to 10 carbon atoms optionally substituted with a fluorine atom, an alkoxy group having 1 to 10 carbon atoms optionally substituted with a fluorine atom, or an electron-withdrawing group, Z represents a single bond or an oxygen atom; Each of a ring ZZ independently represents an aromatic monocyclic or polycyclic ring having 5 to 20 carbon atoms, each carbon atom of the ring ZZ is optionally substituted with a nitrogen atom, an oxygen atom, or a sulfur atom; "ka" represents an integer of 0 to 2; "kb" and "kd" each represent 1 or 2; "kc" and "ke" each represent an integer of 0 to 2.

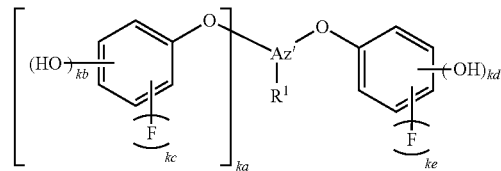

(1B)

Az' represents a linear, branched, or cyclic (ka+2)-valent hydrocarbon group or fluorinated hydrocarbon group having 1 to 19 carbon atoms, and —$CH_2$— constituting the (ka+2)-valent hydrocarbon group is optionally substituted with —O—, —C(=O)— or —Si($R^2R^3$)—; "ka" represents 0 or 1, "kb", "kc", "kd", and "ke" each represent 1 or 2, $R^1$, $R^2$ and $R^3$ are as defined above.

Hereinbelow, each component of the conductive paste composition is described.

Component (A)

The conductive filler as the component (A) to be used for the conductive paste composition of the present invention is preferably selected from the group consisting of gold, silver, silver chloride, platinum, copper, tin, iron, titanium, nickel, palladium, aluminum, tungsten, molybdenum, ruthenium, chromium, indium, solder, carbon, and composites thereof. Examples include metal particles or alloyparticles, such as powders of gold, silver, platinum, copper, tin, iron, titanium, nickel, palladium, aluminum, tungsten, molybdenum, ruthenium, chromium, indium, or solder, and silver-plated powders thereof; powders of carbon black, carbon nanotube, silver chloride, zinc oxide, titanium oxide, or indium tin oxide; and the like.

From the viewpoint of conductivity, gold, silver, or platinum is preferable. From the viewpoint of price, silver, copper, tin, iron, titanium, nickel, aluminum, tungsten, molybdenum, ruthenium, chromium, or stainless steel is preferable. Comprehensively, silver (silver powder) is most preferable.

In particular, silver powder having an average particle size of 5 nm to 10 μm is preferably used as the conductive filler as the component (A).

The method for measuring the average particle size is not particularly limited. For example, a laser diffraction-type particle size distribution measurement apparatus can be used for the measurement.

The conductive filler particles may have any shape, such as spherical, granular, angular, dendritic, flaky, needle-like, or irregular shape. Several types of such fillers may be used in combination.

The conductive filler is added in an amount within a range preferably exceeding 70 parts by mass, more preferably 80 parts by mass or more and 90 parts by mass or less, per 100 parts by mass of the total of the conductive filler (A) and the elastomer resin (C).

Component (B)

The phenol compound described above is incorporated in the conductive paste composition of the present invention as the component (B).

The phenol compound is added in an amount within a range preferably exceeding 0.5 parts by mass, more preferably 1 parts by mass or more and 10 parts by mass or less, per 100 parts by mass of the total of the conductive filler (A), the elastomer resin (C), and the phenol compound (B).

Component (D)

The solvent as the component (D) serves to adjust the viscosity of the conductive paste composition of the present invention to ensure appropriate workability in printing or the like. The solvent may be the same as or different from the organic solvent used in the polymerization of the polyurethane described below.

Specific examples of the solvent as the component (D) used for the conductive paste composition of the present invention include aromatic hydrocarbon-based solvents such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon-based solvents such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methyl-enecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undec-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, or isoparaffin; ketone solvents such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, methyl n-pentyl ketone, methyl isobutyl ketone, and isophorone; alcohol solvents such as 3-methoxybutanol, 3-methyl-3-methoxybutanol, 1-methoxy-2-propanol, and 1-ethoxy-2-propanol; ether solvents such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diethylene glycol diethyl ether, diethylene glycol monomethyl ether, diethylene glycol monoethyl ether, diethylene glycol monopropyl ether, diethylene glycol monobutyl ether, diisopropyl ether, diisobutyl ether, diisopentyl ether, di-n-pentyl ether, methylcyclopentyl ether, methylcyclohexyl ether, di-n-butyl ether, di-sec-butyl ether, di-sec-pentyl ether, di-tert-amyl ether, di-n-hexyl ether, and anisole; ester solvents such as ethylene glycol monobutyl ether acetates, propylene glycol monomethyl ether acetates, propylene glycol monoethyl ether acetates, propylene glycol monopropyl ether acetates, propylene glycol monobutyl ether acetates, propylene glycol diacetates, diethylene glycol monomethyl ether acetates, diethylene glycol monoethyl ether acetates, diethylene glycol monobutyl ether acetates, ethyl lactate, ethyl pyruvate, butyl acetate, methyl 3-methoxypropionate, ethyl 3-ethoxypropionate, tert-butyl acetate, tert-butyl propionate, and propylene glycol monotert-butyl ether acetates; lactone solvents such as γ-butyrolactone; terpene solvents such as α-terpineol, α-pinene, dihydroterpineol, and dihydroterpinyl acetates; and the like. These solvents may be used individually or as a mixture of two or more kinds.

Diethylene glycol monobutyl ether, diethylene glycol monoethyl ether acetate, or diethylene glycol monobutyl ether acetate is particularly preferable because the solvents hardly evaporate during printing and impart suitable viscosity for printing.

The solvent (D) is preferably added in an amount within a range of 100 to 1,000 parts by mass, per 100 parts by mass of the elastomer (C).

Component (C)

The elastomer resin as the component (C) used for the conductive paste composition of the present invention is not particularly limited. Examples thereof include polyurethane, polyester, polyamide, polyvinyl chloride, polystyrene, polyolefin, acrylic rubber, butadiene rubber, styrene-butadiene rubber, isoprene rubber, ethylene-propylene rubber, chloroprene rubber, silicone rubber, fluororubber, and the like. Among them, polyurethane is more preferable.

By incorporating the elastomer resin, the stretchability of the baked product obtained from the conductive paste composition of the present invention is sufficiently exhibited.

Further, the elastomer as the component (C) is more preferably a polyurethane having the structure represented by the following general formulae (1a) to (1c).

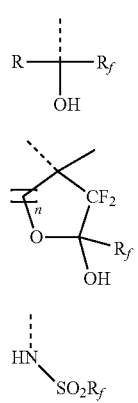

wherein R represents a hydrogen atom, a fluorine atom, or a linear, branched, or cyclic hydrocarbon group having 1 to 10 carbon atoms optionally substituted with a fluorine atom; $R_f$ represents a fluorine atom, or a linear, branched, or cyclic fluorinated hydrocarbon group having 1 to 10 carbon atoms; "n" is an integer of 1 or 2; and the dashed line represents a bonding arm.

Examples of the structures represented by the general formulae (1a) to (1c) above include the following compounds.

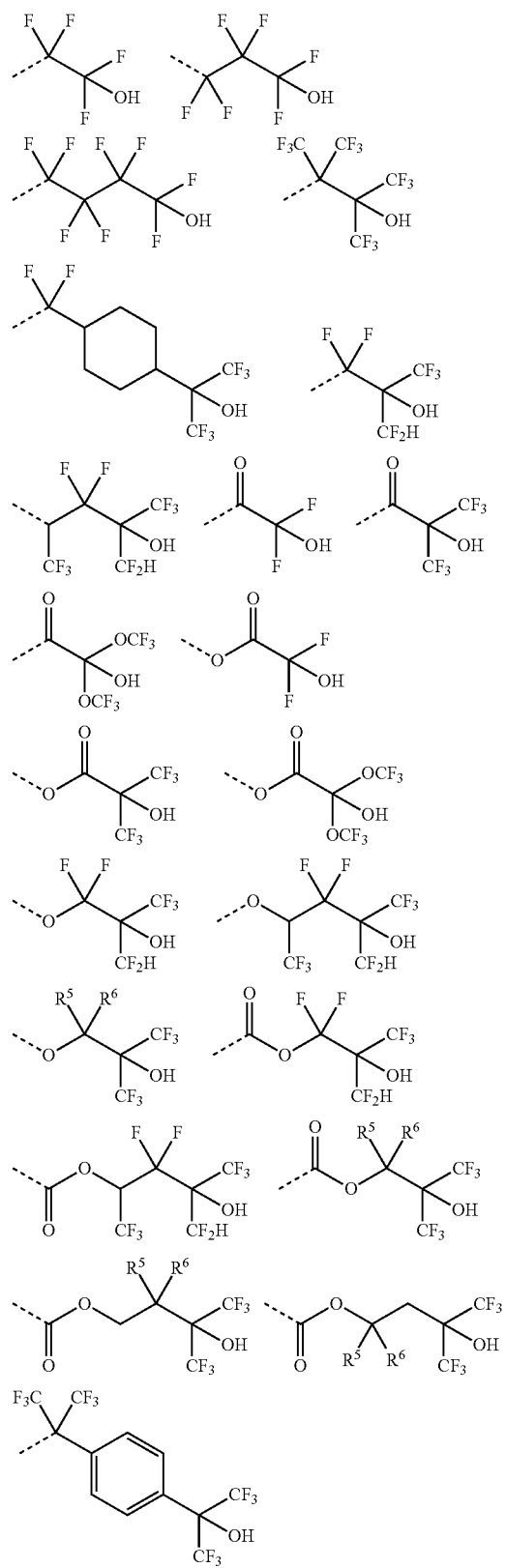

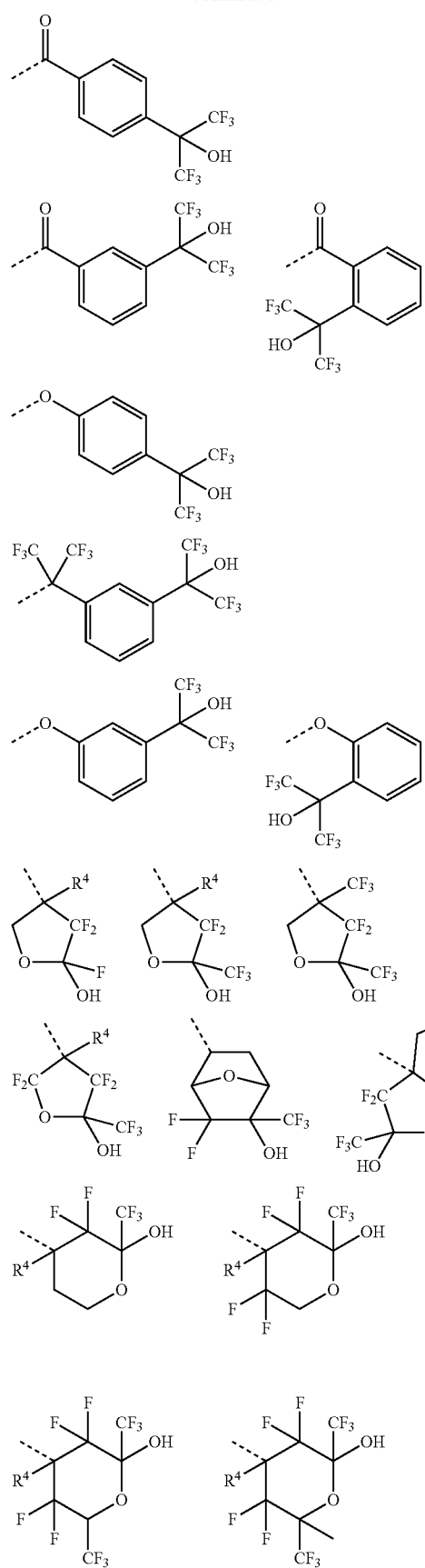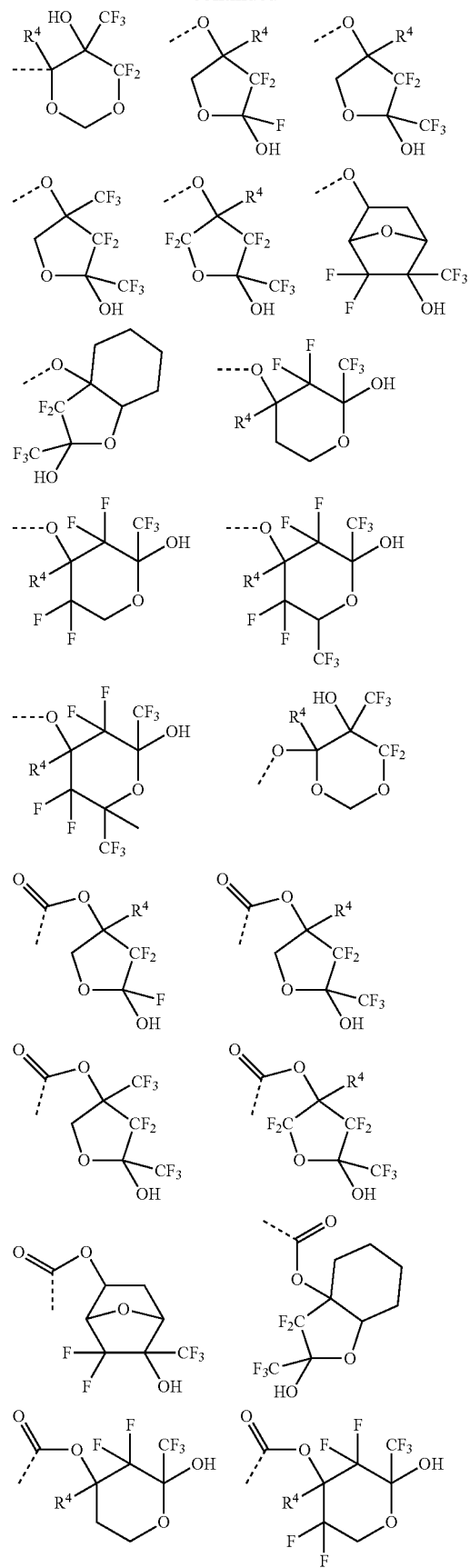

-continued

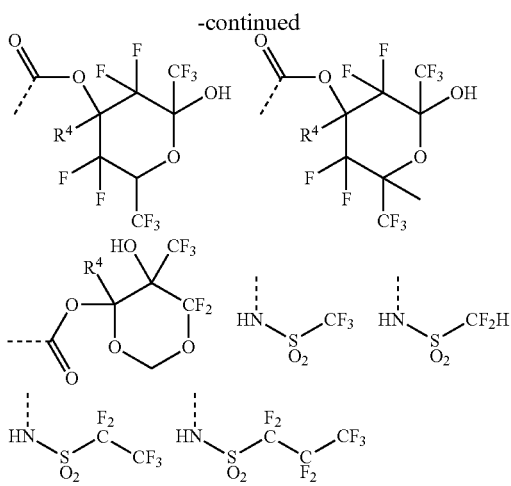

wherein $R^4$ is a hydrogen atom or a monovalent hydrocarbon group having 1 to 3 carbon atoms; $R^5$ and $R^6$ each independently represent a hydrogen atom or a linear, branched, or cyclic hydrocarbon group having 1 to 6 carbon atoms, and $R^5$ and $R^6$ are optionally bonded to each other to form a non-aromatic ring having 3 to 8 carbon atoms together with a carbon atom bonded to $R^5$ and $R^6$; and the dashed line represents a bonding arm.

A polyurethane having the structure represented by the general formulae (1a) to (1c) above can be obtained, for example, by a reaction between a polyisocyanate and a polyol, polyamine, polycarboxylic acid, or the like having the structure represented by the general formulae (1a) to (1c) above according to a known method such as one-shot method or prepolymer method. Preferably, prepolymer method is employed.

In the prepolymer method, a polyurethane is synthesized through steps of: (a) reacting a diisocyanate and a high-molecular-weight polyol with excess isocyanate groups to obtain a reaction mixture containing a prepolymer having an isocyanate group at a terminal; and (b) reacting the prepolymer with a low-molecular-weight diol, diamine, or dicarboxylic acid (chain extender) to polymerize the prepolymer. Further, a polyisocyanate having three or more reactive groups, or a polyol, polyamine, or polycarboxylic acid having three or more reactive groups, may be added to obtain a polyurethane having a crosslink structure.

Further, after the polymerization in (b) is performed with excess amount of isocyanate groups, a capping agent having a reactive group (such as a hydroxyl group, an amino group, a carboxyl group, or the like) that can react with an isocyanate group may be added to introduce a functional group derived from the capping agent to the urethane terminal.

In the reactions of (a) and (b) described above, all or part of at least one of the high-molecular-weight polyol, the chain extender, and the capping agent can be substituted with the structure represented by the general formulae (1a) to (1c) above, so that structure is introduced into the polyurethane.

Further, in a case where the structure represented by the general formulae (1a) to (1c) above can react with an isocyanate, a polyurethane may be formed while the structure represented by the general formulae (1a) to (1c) above is protected with a suitable protective group, followed by a deprotection reaction, thereby synthesizing a polyurethane containing the structure represented by the general formulae (1a) to (1c).

Further, the conductive paste composition of the present invention is more preferably such that the elastomer resin as the component (C) is a polyurethane having the structures represented by the following general formulae (2a) to (2c),

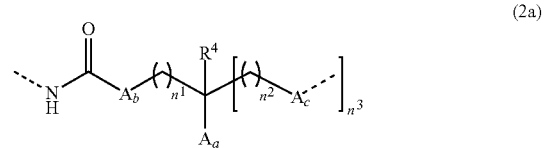

(2a)

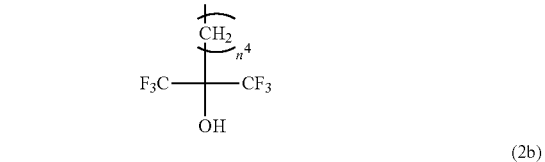

(2b)

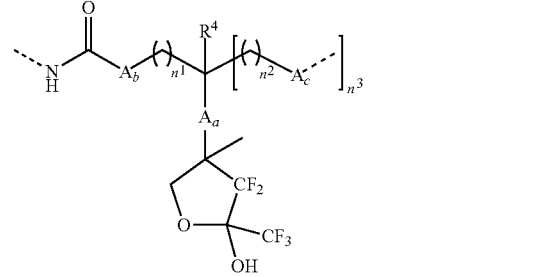

(2c)

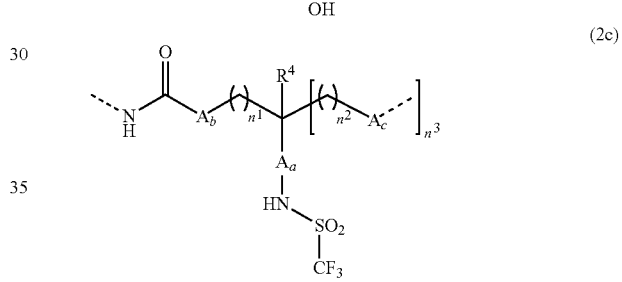

wherein $R^4$ is a hydrogen atom or a monovalent hydrocarbon group having 1 to 3 carbon atoms; $A_a$ represents a single bond, or a linear, branched, or cyclic divalent hydrocarbon group having 1 to 20 carbon atoms; and $-CH_2-$ constituting $A_a$ is optionally substituted with $-O-$, $-C(=O)-$, $-C(=O)O-$ or $-C_6H_4-$, or $-NR^8-C(=O)-$; $R^8$ is a hydrogen atom, or a linear or branched alkyl group having 1 to 4 carbon atoms; $A_b$ represents $-O-$, $-NR^8-$, or $-C(=O)O-$; $A_c$ represents $-O-$, $-NR^8-$, $-C(=O)O-$, or $-NR^8-C(=O)-$; each of $n^1$, $n^2$, and $n^4$ is an integer of 0 to 10; $n^3$ is an integer of 0 or 1; and a dashed line represents a bonding arm.

Polyisocyanate

Examples of the polyisocyanate as a constituent component of the polyurethane include: aliphatic and alicyclic polyisocyanates, such as ethylene diisocyanate, trimethylene diisocyanate, tetramethylene diisocyanate, pentamethylene diisocyanate, hexamethylene diisocyanate (HDI), octamethylene diisocyanate, nonamethylene diisocyanate, 2-methylpentane-1,5-diisocyanate, 3-methylpentane-1,5-diisocyanate, 2,2'-dimethylpentane diisocyanate, 2,2,4-trimethylhexane diisocyanate, decamethylene diisocyanate, butene diisocyanate, 1,3-butadiene-1,4-diisocyanate, 2,4,4-trimethylhexamethylene diisocyanate, 1,6,11-undecamethylene triisocyanate, 1,3,6-hexamethylene triisocyanate, 1,8-diisocyanato-4-isocyanatomethyloctane, 2,5,7-trimethyl-1,8-diisocyanato-5-isocyanatomethyloctane, bis (isocyanatoethyl) carbonate, bis (isocyanatoethyl)ether, 1,4-butylene glycol dipropyl ether-ω) ω-diisocyanate, lysine isocyanatomethyl ester, lysine triisocyanate, 2-isocyanatoethyl-2,6-diisocyanate hexanoate, 2-isocyanatopropyl-2,6-diisocyanate hexanoate, bis(4-isocyanato-n-butylidene)pentaerythritol, 2,6-diisocyanatomethyl caproate, isophorone diisocyanate (IPDI), 1,3-cyclohexyl diisocyanate, 1,4-cyclohexyl diisocyanate, 1,3-bis(isocyanatomethyl)cyclohexane, 1,4-bis(isocyanatomethyl)cyclohexane, 1,3-bis(isocyanatoethyl)cyclohexane, 1,4-bis(isocyanatoethyl)cyclohexane, methylcyclohexane diisocyanate, 2,2'-dimethyldicyclohexylmethane diisocyanate, 4,4'-dicyclohexylmethane diisocyanate, dimer acid diisocyanate, 2,5-diisocyanatomethylbicyclo[2,2,1]-heptane, 2,6-diisocyanatomethylbicyclo[2,2,1]-heptane, 2-isocyanatomethyl-2-(3-isocyanatopropyl)-5-isocyanatome thylbicyclo-[2,2,1]-heptane, 2-isocyanatomethyl-2-(3-isocyanatopropyl)-6-isocyanatome thylbicyclo-[2,2,1]-heptane, 2-isocyanatomethyl-3-(3-isocyanatopropyl)-5-(2-isocyanat oethyl)-bicyclo-[2,2,1]-heptane, 2-isocyanatomethyl-3-(3-isocyanatopropyl)-6-(2-isocyanat oethyl)-bicyclo-[2,2,1]-heptane, 2-isocyanatomethyl-2-(3-isocyanatopropyl)-5-(2-isocyanat oethyl)-bicyclo-[2,2,1]-heptane, and 2-isocyanatomethyl-2-(3-isocyanatopropyl)-6-(2-isocyanat oethyl)-bicyclo-[2,2,1]-heptane; aromatic polyisocyanates, such as 2,4-tolylene diisocyanate or 2,6-tolylene diisocyanate and isomer mixture thereof (TDI), 4,4'-diphenylmethane diisocyanate or 2,4'-diphenylmethane diisocyanate and isomer mixture thereof (MDI), tolidine diisocyanate (TODI), para-phenylene diisocyanate, naphthalene diisocyanate (NDI), and 4,4'-dibenzyl diisocyanate; aromatic-aliphatic polyisocyanates, such as ortho-xylylene diisocyanate, meta-xylylene diisocyanate, para-xylylene diisocyanate, 1,3-tetramethylxylylene diisocyanate, and 1,4-tetramethylxylylene diisocyanate; polymers thereof prepared as urethane-modified products, biuret-modified products, carbodiimide-modified products, uretonimine-modified products, uretdione-modified products, isocyanurate-modified products, or allophanate-modified products; and the like.

These polyisocyanates may be used individually or two or more kinds thereof may be combined.

High-Molecular-Weight Polyol

The high-molecular-weight polyol used as a constituent component of the polyurethane can be a polyol having a number-average molecular weight of 500 to 5,000 containing two or more hydroxyl groups that can react with an isocyanate group. Examples of the high-molecular-weight polyol include polyether polyol, polyester polyol, polycarbonate polyol, acrylic polyol, polyolefin having a terminal hydroxyl group, silicone polyol, castor oil-based polyol, and the like.

Examples of the polyether polyol include polyoxypropylene glycols, polyoxyethylene glycols, polyoxytetramethylene glycols, copolymers thereof, and the like.

The polyoxypropylene glycols and polyoxyethylene glycols are alkylene-oxide addition polymers using a low-molecular-weight polyol, polyamine, or amino alcohol as an initiator. Examples of the low-molecular-weight polyol include: dihydric alcohols, such as ethylene glycol, 1,2-propanediol, 1,3-propanediol, 1,2-butanediol, 1,3-butanediol, 1,4-butanediol, 1,5-pentanediol, 1,6-hexanediol, 1,7-heptanediol, 1,8-octanediol, 1,9-nonanediol, neopentyl glycol, 3-methyl-1,5-pentanediol, 3,3-dimethylolheptane, 2,2,2-trimethylpentanediol, 1,4-dihydroxy-2-butene, 2,6-dimethyl-1-octene-3,8-diol, diethylene glycol, triethylene glycol, dipropylene glycol, cyclohexane-1,3-diol, cyclohexane-1,4-diol, cyclohexane-1,3-dimethanol, cyclohexane-1,4-dimethanol, 1,3-adamantanedimethanol, dimer acid diol, 1,2-benzenediol, 1,3-benzenediol, 1,4-benzenediol, hydroquinone di(2-hydroxyethyl ether), bisphenol A, bis(β-hydroxyethyl)benzene, and xylylene glycol; trihydric alcohols, such as glycerin, trimethylolpropane, and triisopropanolamine; tetrahydric alcohols, such as pentaerythritol, α-methyl glucoside, and diglycerin; and polyhydric alcohols, such as sorbitol and sucrose. Examples of the low-molecular-weight amino alcohol include monoethanolamine, dimethanolamine, and triethanolamine. Examples of the low-molecular-weight polyamine include ethylenediamine, propylenediamine, butanediamine, pentamethylenediamine, hexamethylenediamine, isophorone diamine, piperazine, toluenediamine, metaphenylenediamine, diphenylmethanediamine, xylylenediamine, dimethylthiotoluenediamine, 4,4-methylenebis-o-chloroaniline, and the like. These initiators may be used individually or two or more kinds thereof may be combined.

Further, by using the low-molecular-weight polyol containing the structures represented by the general formulae (1a) to (1c), a polyether polyol containing the structures represented by the general formulae (1a) to (1c) can be obtained. Such a polyether polyol can also be synthesized by performing the polymerization while protecting the structure represented by the general formulae (1a) to (1c), followed by a deprotection reaction.

Examples of the alkylene oxide include ethylene oxide, propylene oxide, butylene oxide, and the like. One or a combination of two or more thereof can be used. Polyalkylene polyol obtained from a combination of two or more kinds may have either a block or random structure.

The polyoxytetramethylene glycol is a ring-opening polymerization product obtained through cationic polymerization of tetrahydrofuran (THF). Examples thereof include crystalline polytetramethylene glycol, amorphous polytetramethylene glycol obtained by copolymerizing THE with alkyl-substituted tetrahydrofuran, such as 3-methyltetrahydrofuran, aforementioned dihydric alcohols, or the like.

Examples of the polyester polyol include polymerization condensates between any of the aforementioned low-molecular-weight polyols and polycarboxylic acid or oligomer acid; and ring-opening polymers of lactone or lactide using the low-molecular-weight polyol as an initiator.

Examples of the polycarboxylic acid include oxalic acid, malonic acid, succinic acid, glutaric acid, adipic acid, pimelic acid, suberic acid, glutaconic acid, azelaic acid, sebacic acid, 1,1-dimethyl-1,3-dicarboxypropane, 3-methyl-3-ethylglutaric acid, 1,4-cyclohexyldicarboxylic acid, hexahydrophthalic acid, maleic acid, fumaric acid, itaconic acid, muconic acid, α-hydromuconic acid, β-hydromuconic acid, phthalic acid, ortho-phthalic acid, terephthalic acid, isophthalic acid, toluenedicarboxylic acid, naphthalenedicarboxylic acid, HET acid, dimer acid, hydrogenated dimer acid. It is also possible to use a derivative, acid anhydride, or acid halide thereof, for example.

Examples of the lactone include β-propiolactone, β-butyrolactone, γ-butyrolactone, γ-valerolactone, δ-valerolactone, ε-caprolactone, and the like. Examples of the lactide include L-lactide and D-lactide.

One kind of the low-molecular-weight polyol, polycarboxylic acid, oligomer acid, lactone, or lactide, which are constituent components of the polyester polyol, may be used, or two or more kinds of each constituent component may be used in combination.

Further, it is also possible to use polyester-amide polyol obtained by substituting a part of the low-molecular-weight polyol of the polyester polyol with the aforementioned low-molecular-weight polyamine or amino alcohol.

Examples of the polycarbonate polyol include polymerization condensates between any of the aforementioned polyols and a carbonate compound.

Examples of the carbonate compound include dimethyl carbonate, diethyl carbonate, ethylene carbonate, propylene carbonate, diphenyl carbonate, dinaphthyl carbonate, dianthryl carbonate, diphenanthryl carbonate, diindanyl carbonate, tetrahydronaphthyl carbonate, and the like.

One kind of the low-molecular-weight polyol or carbonate compound, which are constituent components of the polycarbonate polyol may be used, or two or more kinds of each constituent component may be used in combination.

Examples of the acrylic polyol include copolymers obtained by copolymerizing hydroxy group-containing (meth)acrylate with vinyl monomer.

Examples of the hydroxyl group-containing (meth)acrylate include 2-hydroxyethyl (meth)acrylate, hydroxypropyl (meth)acrylate, hydroxybutyl (meth)acrylate, 3-hydroxy-2,2-dimethylpropyl acrylate, 2,2-dihydroxymethylbutyl (meth)acrylate, pentaerythritol tri(meth)acrylate, polyhydroxyalkyl maleate, polyhydroxyalkyl fumarate, and the like. These (meth)acrylates may be used individually or two or more kinds thereof may be combined.

Examples of the vinyl monomer include: (meth)acrylic esters, such as methyl (meth)acrylate, ethyl (meth)acrylate, propyl(meth)acrylate, isopropyl(meth)acrylate, butyl(meth)acrylate, isobutyl(meth)acrylate, s-butyl(meth)acrylate, t-butyl(meth)acrylate, pentyl(meth)acrylate, isopentyl (meth)acrylate, hexyl(meth)acrylate, 2-ethylhexyl(meth)acrylate, octyl(meth)acrylate, nonyl(meth)acrylate, isononyl (meth)acrylate, decyl(meth)acrylate, dodecyl(meth)acrylate, cyclohexyl(meth)acrylate, phenyl(meth)acrylate, benzyl (meth)acrylate, allyl(meth)acrylate, ethylene glycol di(meth)acrylate, butylene glycol di(meth)acrylate, hexanediol di(meth)acrylate, and oligo ethylene glycol di(meth)acrylate; aromatic vinyls, such as styrene, vinyltoluene, and α-methylstyrene; vinyl cyanides, such as (meth)acrylonitrile; carboxyl group-containing vinyl monomers, such as fumaric acid, maleic acid, and itaconic acid, or alkyl esters thereof; isocyanate group-containing monomers, such as 3-(2-isocyanato-2-propyl)-α-methylstyrene; fluorine-containing vinyl monomers, such as tetrafluoroethylene, chlorotrifluoroethylene, trichlorofluoroethylene, hexafluoropropylene, vinylidene fluoride, vinyl fluoride, and trifluoromethyltrifluoroethylene; silicone monomers, such as γ-(meth)acryloxypropyltrimethoxysilane; and the like. These monomers may be used individually or two or more kinds thereof may be combined.

Examples of the polyolefin having a terminal hydroxyl group include compounds obtained by attaching a hydroxyl group to a terminal of one or more olefin polymers. Examples of the olefin include ethylene, propylene, butadiene, isoprene, styrene, acrylonitrile, vinyl ether, and vinyl acetate. Further, part of these structures may be substituted with a halogen, such as fluorine, chlorine, or bromine.

Examples of the silicone polyol include vinyl group-containing silicone compounds obtained by polymerizing γ-methacryloxypropyltrimethoxysilane or the like; and polysiloxanes having at least one terminal hydroxyl group per molecule, such as α,ω-dihydroxypolydimethylsiloxane and α,ω-dihydroxypolydiphenylsiloxane.

Examples of the vegetable oil-based polyol include hydroxyl group-containing vegetable oils, such as castor oil and coconut oil; ester-modified castor oil polyol, dehydrated castor oil, partially dehydrated castor oil, and hydrogenated castor oil, which can be obtained from a reaction between castor oil fatty acid and polyol; and the like.

The high-molecular-weight polyol has a number-average molecular weight in a range of preferably 500 or more and 5,000 or less, more preferably 1,000 or more and 3,000 or less, further preferably 1,000 or more and 2,000 or less.

When the number-average molecular weight of the high-molecular-weight polyol is at the lower limit or more, it is possible to suppress excessive increase in the urethane group concentration in the polyurethane, increase in the hardness due to this concentration increase, and decrease in performance such as stretchability. Further, when the number-average molecular weight is at the upper limit or less, it is possible to suppress excessive decrease in the urethane group concentration, prevent the strength attributable to the urethane bond from decreasing, and achieve both strength and stretchability at appropriate levels.

The high-molecular-weight polyol is preferably bifunctional polyol or trifunctional polyol, more preferably bifunctional polyol.

Chain Extender

Examples of the chain extender to be employed include: dihydric alcohols, such as ethylene glycol, 1,2-propanediol, 1,3-propanediol, 1,2-butanediol, 1,3-butanediol, 1,4-butanediol, 1,5-pentanediol, 1,6-hexanediol, 1,7-heptanediol, 1,8-octanediol, 1,9-nonanediol, neopentyl glycol, 3-methyl-1,5-pentanediol, 3,3-dimethylolheptane, 2,2,2-trimethylpentanediol, 1,4-dihydroxy-2-butene, 2,6-dimethyl-1-octene-3,8-diol, diethylene glycol, triethylene glycol, dipropylene glycol, cyclohexane-1,3-diol, cyclohexane-1,4-diol, cyclohexane-1,3-dimethanol, cyclohexane-1,4-dimethanol, 1,3-adamantanedimethanol, dimer acid diol, 1,2-benzenediol, 1,3-benzenediol, 1,4-benzenediol, hydroquinone di(2-hydroxyethyl ether), bisphenol A, bis(β-hydroxyethyl)benzene, and xylylene glycol; amines, such as ethanolamine, dimethanolamine, triethanolamine, ethylenediamine, propylenediamine, butanediamine, pentamethylenediamine, hexamethylenediamine, isophorone diamine, piperazine, toluenediamine, metaphenylenediamine, diphenylmethanediamine, xylylenediamine, dimethylthiotoluenediamine, and 4,4-methylenebis-o-chloroaniline; and the like.

Furthermore, the polyols represented by the following general formulae (3a) to (3c) may be used as a chain extender to introduce it into a side chain of the polyurethane. As the chain extender, the polyols represented by the general formulae (3a) to (3c) may be used individually, or they may be combined with any of the aforementioned chain extenders.

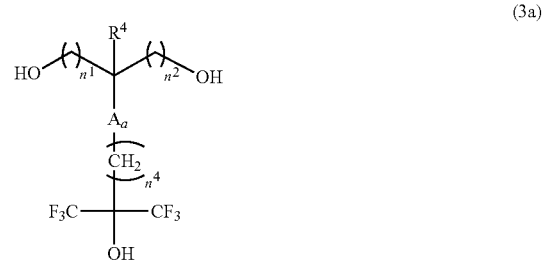

(3a)

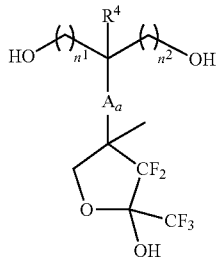
(3b)
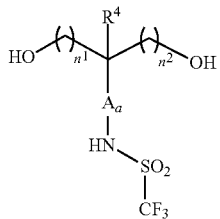
(3c)
wherein R⁴, $A_a$, $n^1$, $n^2$ and $n^4$ are as defined above.
Specific examples of the linear, branched, or cyclic hydrocarbon group having 1 to 20 carbon atoms, which is represented by $A_a$, include the following substances.
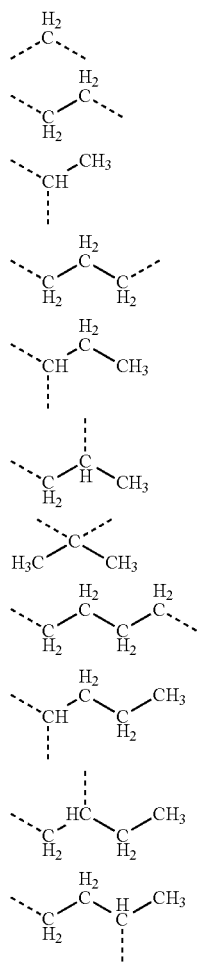
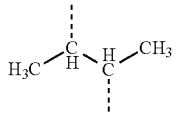
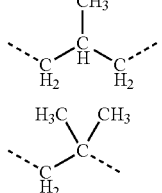
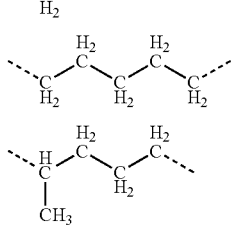
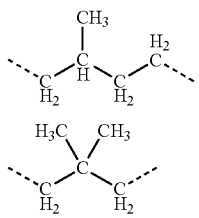
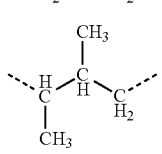
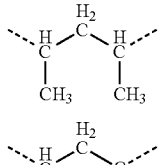
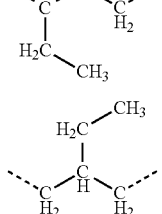
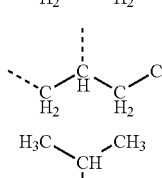
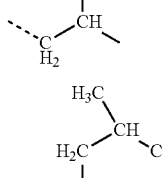
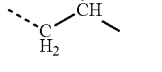

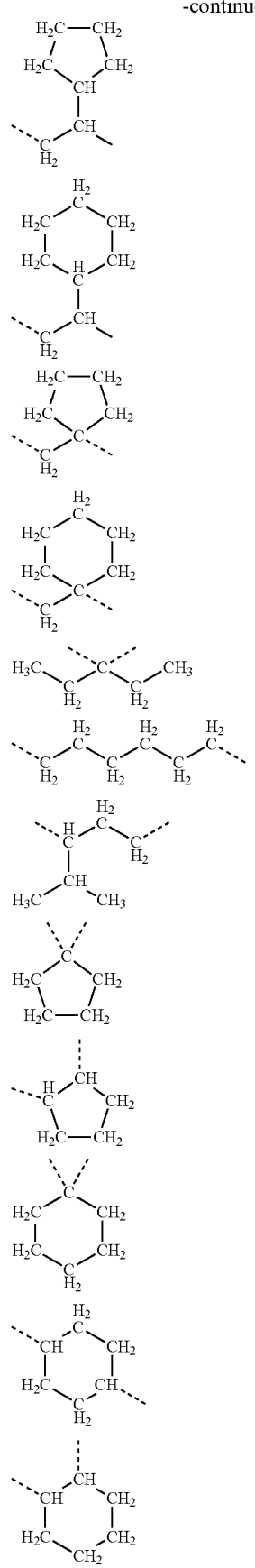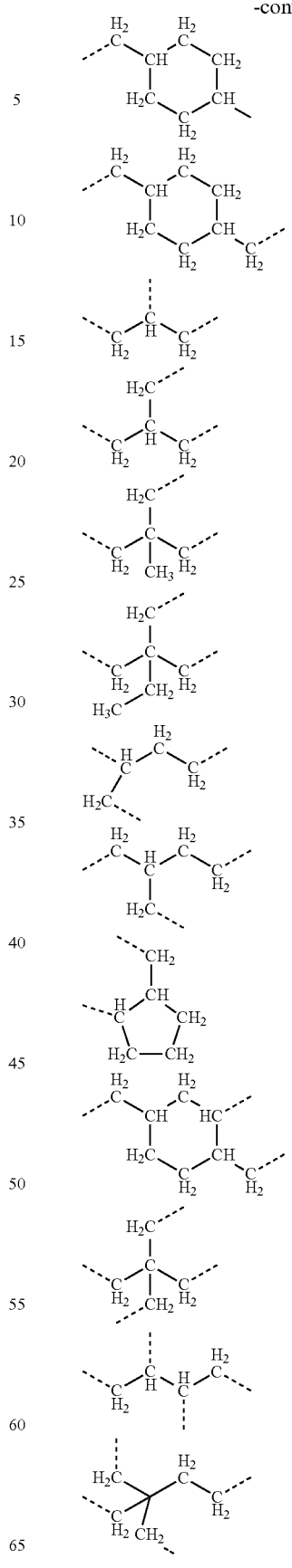

The examples can further include ones in which any —CH$_2$— in A$_a$ above is substituted with —O—, —C(=O)—, —C(=O) O—, —C$_6$H$_4$—, or —NR$^8$—C (=O)—, wherein R$^8$ is a hydrogen atom, or a linear or branched alkyl group having 1 to 4 carbon atoms.
Examples of the chain extenders represented by the general formulae (3a) to (3c) include, but not limited to, the following substances.
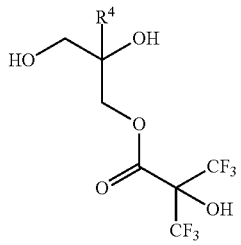
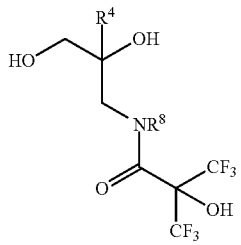
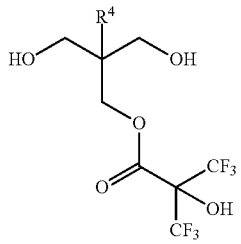
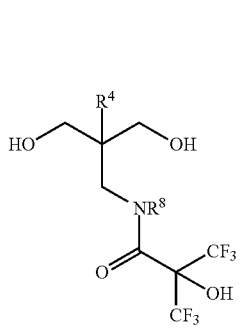
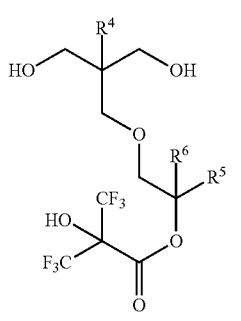
-continued
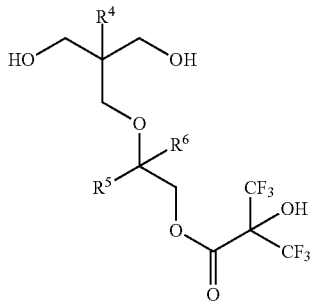
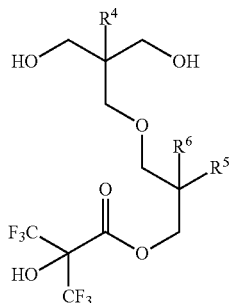
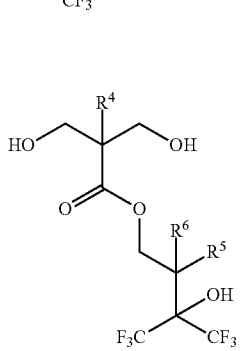
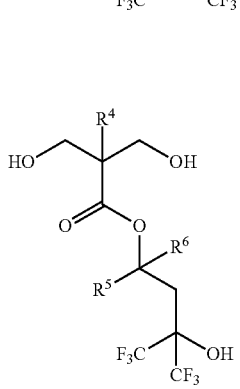
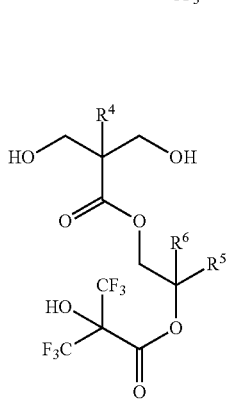

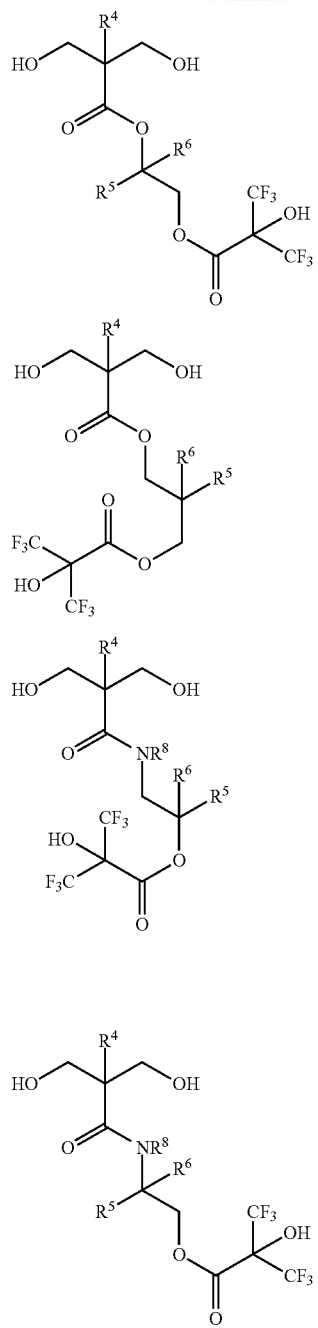
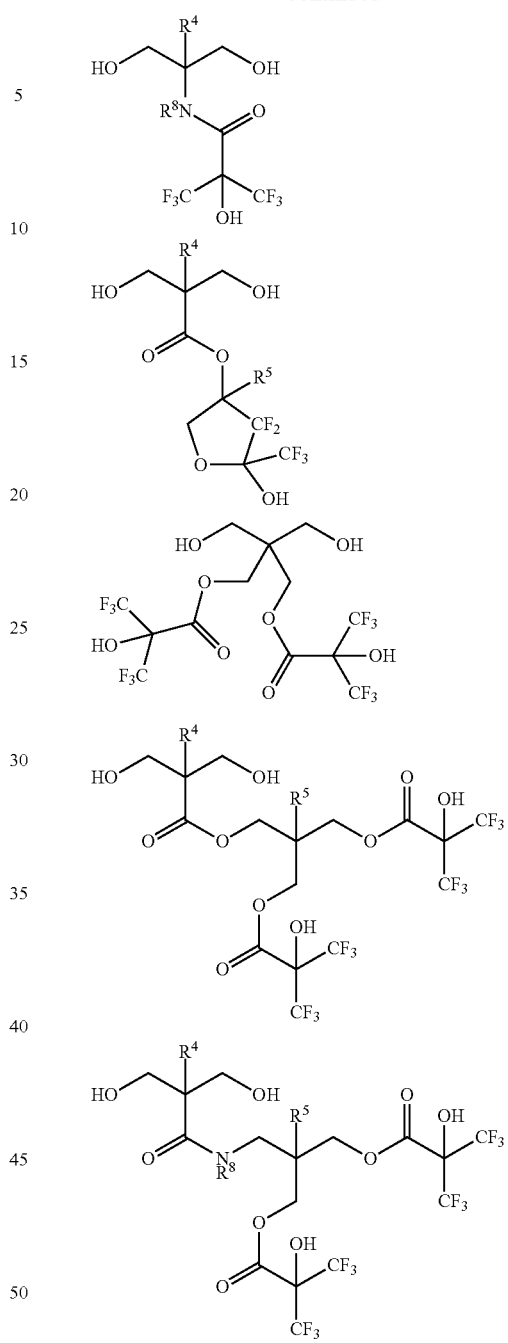
wherein $R^4$, $R^5$, $R^6$ and $R^8$ are as defined above.
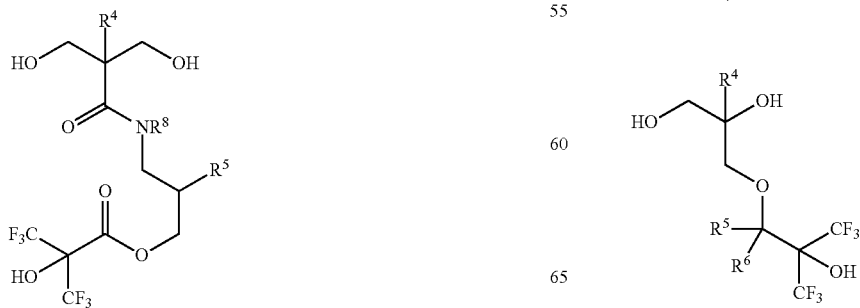

-continued
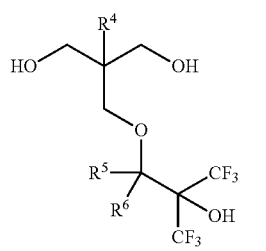
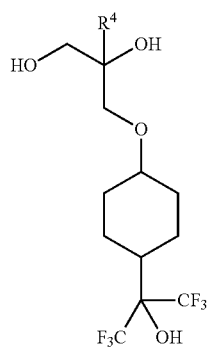
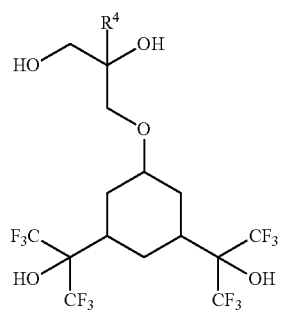
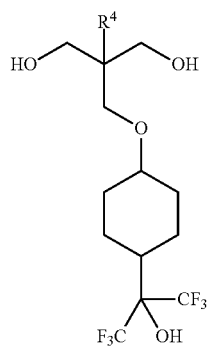
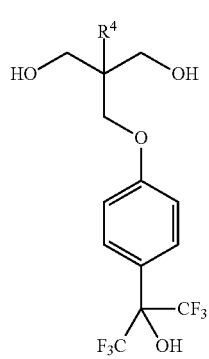
-continued
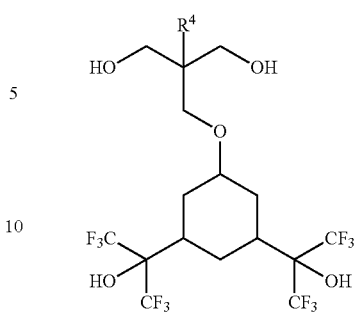
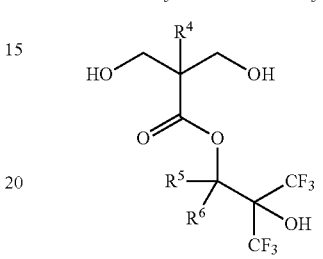
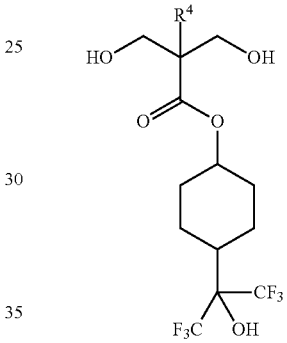
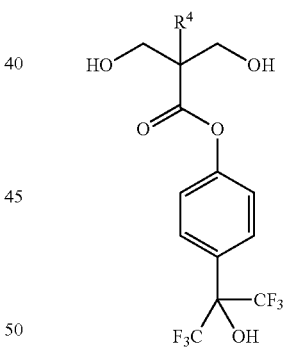
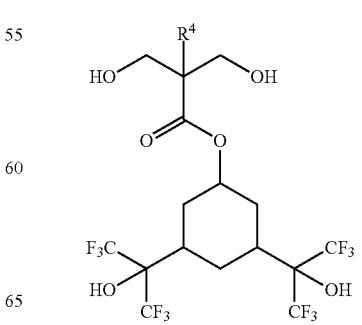

-continued

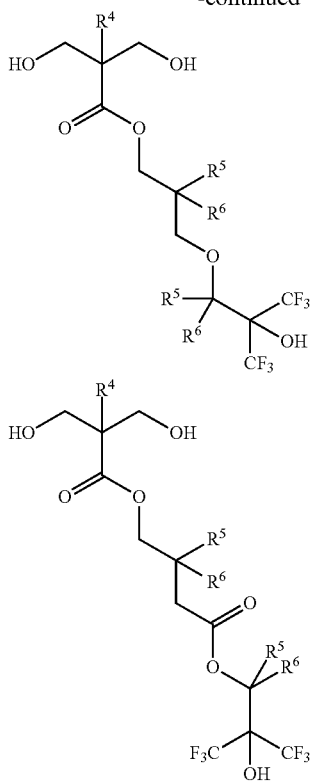

wherein R⁴, R⁵, and R⁶ are as defined above.

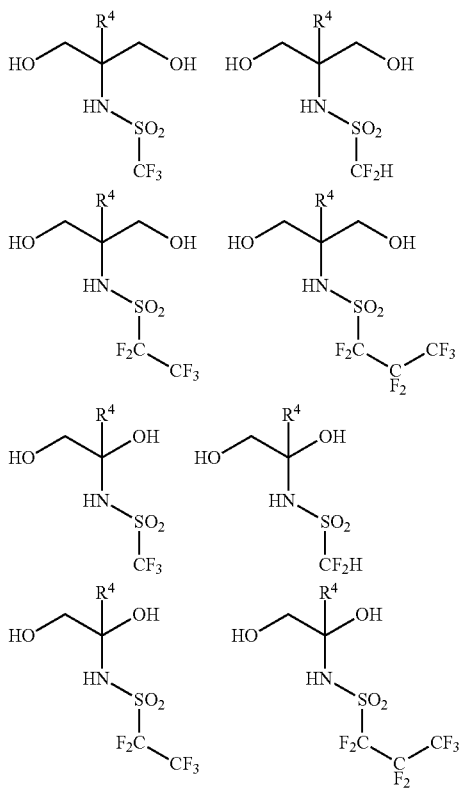

wherein R⁴ is as defined above.

The chain extenders having the structures represented by the general formulae (3a) to (3c) above are used in an amount of preferably 5 to 50 mass %, more preferably 20 to 40 mass %, relative to the total amount of the constituent components of the urethane.

Crosslinking Agent

Examples of crosslinking agent to be used include trihydric alcohols, such as glycerin, trimethylolpropane, and triisopropanolamine; and polyhydric alcohols, such as pentaerythritol, α-methyl glucoside, and diglycerin.

The crosslinking agent is added in an amount within preferably 0 to 5 mass %, more preferably 0 to 3 mass %, relative to the total amount of the constituent components of the urethane.

When the amount of the crosslinking agent to be added is at this upper limit or less, the strength does not excessively increase, and the flexibility and stretchability are not impaired. This is suitable in terms of the use of the conductive paste composition of the present invention.

Organic Solvent

The polyurethane is synthesized by bulk polymerization or solution polymerization. Examples of an organic solvent used in the solution polymerization include: aromatic hydrocarbon solvents, such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvents, such as n-heptane, isoheptane, n-hexane, octane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, cyclohexane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvents, such as cyclohexanone, cyclopentanone, acetone, methyl ethyl ketone, 2-octanone, 2-nonanone, 2-heptanone, 3-heptanone, 4-heptanone, 2-hexanone, 3-hexanone, diisobutyl ketone, methyl isobutyl ketone, methylcyclohexanone, and methyl n-pentyl ketone; ether solvents, such as ethylene glycol dimethyl ether, propylene glycol dimethyl ether, diethylene glycol dimethyl ether, diethylene glycol diethyl ether, diethylene glycol dibutyl ether, diethylene glycol ethyl methyl ether, diethylene glycol butyl methyl ether, diethyl ether, diisopropyl ether, di-n-butyl ether, di-sec-butyl ether, diisobutyl ether, amyl ether, isoamyl ether, di-tert-amyl ether, methyl cyclopentyl ether, methyl cyclohexyl ether, methyl-tert-butyl ether, di-n-hexyl ether, anisole, dihydroterpinyl acetate, tetrahydrofuran, and dioxane; ester solvents, such as ethylene glycol monomethyl ether acetate, ethylene glycol monoethyl ether acetate, ethylene glycol monobutyl ether acetate, ethylene glycol monopropyl ether acetate, ethylene glycol diacetate, propylene glycol monomethyl ether acetate, propylene glycol monoethyl ether acetate, propylene glycol monopropyl ether acetate, propylene glycol monobutyl ether acetate, propylene glycol mono-tert-butyl ether acetate, propylene glycol diacetate, diethylene glycol monomethyl ether acetate, diethylene glycol monoethyl ether acetate, diethylene glycol monopropyl ether acetate, diethylene glycol monobutyl ether acetate, methyl acetate, ethyl acetate, butyl acetate, isobutyl acetate, acetate-tert-butyl, ethyl pyruvate, methyl 3-methoxypropionate, ethyl 3-ethoxypropionate, tert-butyl propionate, 3-methoxybutyl acetate, and ethyl-3-ethoxypropionate; lactone solvents, such as γ-butyrolactone; nitrile solvents, such as acetonitrile; halogen-based solvents, such as methyl chloride, methylene chloride, chloroform, carbon tetrachloride, 1,2-dichloroethane, and 1,1,2,2-tetrachloroethane; polar nonprotic solvents, such as N-methylpyrrolidone, N,N'-dimethylformamide, N,N'-dimethylacetamide, dimethyl sulfoxide, and hexamethylphosphoramide; and the like.

The organic solvent is added in an amount within preferably 20 parts by mass or more and 500 parts by mass or less, more preferably 25 parts by mass or more and 100 parts by mass or less, per 100 parts by mass of the total amount of the polyurethane constituent components (polyisocyanate, high-molecular-weight polyol, chain extender, cross-linking agent).

The organic solvent may be removed by distillation under reduced pressure or by crystallization after the polymerization reaction, or may be applied to a conductive paste composition in a form of polyurethane solution without being removed.

Catalyst

In the polyurethane synthesis, a catalyst is preferably added to promote the urethane bond formation reaction, as necessary.

The catalyst to be used for the urethane formation can be appropriately selected from known catalysts. Examples thereof include amine-based catalysts, ammonium salt-based catalysts, potassium salt-based catalysts, organometallic catalysts, and the like.

Examples of the amine-based catalysts include triethylamine, N,N-dimethylcyclohexylamine, triethylenediamine, 2-methyltriethylenediamine, N,N,N',N'-tetramethylethylenediamine, N,N,N',N'-tetramethylpropylenediamine, N,N,N',N",N"-pentamethyldiethylenetriamine, N,N,N',N",N"-pentamethyl-(3-aminopropyl)ethylenediamine, N,N,N',N", N"-pentamethyldipropylenetriamine, N,N,N',N'-tetramethylhexamethylenediamine, bis(2-dimethylaminoethyl) ether, dimethylethanolamine, dimethylisopropanolamine, dimethylaminoethoxyethanol, N,N-dimethylhexanolamine, N,N-dimethyl-N'-(2-hydroxyethyl)ethylenediamine, N,N-dimethyl-N'-(2-hydroxyethyl) propanediamine, N,N,N'-trimethylaminoethylethanolamine, bis(dimethylaminopropyl)amine, bis(dimethylaminopropyl) isopropanolamine, N-methyl-N'-(2-dimethylaminoethyl) piperazine, N-methyl-N'-(2-hydroxyethyl)piperazine, N-methylmorpholine, N-ethylmorpholine, 1-methylimidazole, 1,2-dimethylimidazole, 1-isobutyl-2-methylimidazole, 1-dimethylaminopropylimidazole, 1-(2-hydroxyethyl)imidazole, 1-(2-hydroxypropyl)imidazole, 1-(2-hydroxyethyl)-2-methylimidazole, 1-(2-hydroxypropyl)-2-methylimidazole, and the like.

Examples of the ammonium salt-based catalysts include quaternary ammonium salts, such as tetraethyl hydroxyl ammonium; ammonium salts of 1,8-diazabicyclo(5,4,0)-undecene-7 or 1,5-diazabicyclo(4,3,0)-nonene-5 with octylic acid, oleic acid, p-toluenesulfonic acid, formic acid, phenolic acid, ortho-phthalic acid, acetic acid, maleic acid, or boric acid; and the like.

Examples of the potassium salt-based catalysts include potassium carbonate, potassium acetate, potassium octylate, and the like.

Examples of the organometallic catalysts include: organotin compounds, such as tin acetate, tin octylate (tin 2-ethylhexaonate), tin oleate, tin laurate, dibutyltin diacetate, dimethyltin dilaurate, dibutyltin dilaurate, dibutyltin dimercaptide, dibutyltin maleate, dibutyltin dineodecanoate, dioctyltin dimercaptide, dioctyltin dilaurate, dibutyltin dichloride; organolead compounds, such as lead octoate and lead naphthenate; organonickel compounds, such as nickel naphthenate; organocobalt compounds, for example, cobalt naphthenate; organocopper compounds, such as copper octenoate; organobismuth compounds, such as bismuth octylate and bismuth neodecanoate; and the like.

Since the polyurethane used as the elastomer as the component (C) of the present invention contains the structures represented by the general formulae (1a) to (1c), and therefore may be capable of inhibiting the activity of a basic catalyst, it is preferable to use an organometallic catalyst, and more preferable example thereof is an organobismuth compound.

These catalysts for the urethane formation may be used individually or in a combination of two or more kinds thereof. The catalyst for the urethane formation is used in an amount within preferably 0 parts by mass or more and 5 parts by mass or less, more preferably 0.1 parts by mass or more and 2 parts by mass or less, per 100 parts by mass of the total amount of the polyurethane constituent components.

Capping Agent

To the polyurethane according to the present embodiments after the polymerization with excess isocyanate groups, a terminal capping agent may be added to introduce a functional group derived from the capping agent to the polyurethane terminal.

For example, as the capping agent for polyurethane terminal, the following hydroxy(meth)acrylates can be used to synthesize urethane acrylate.

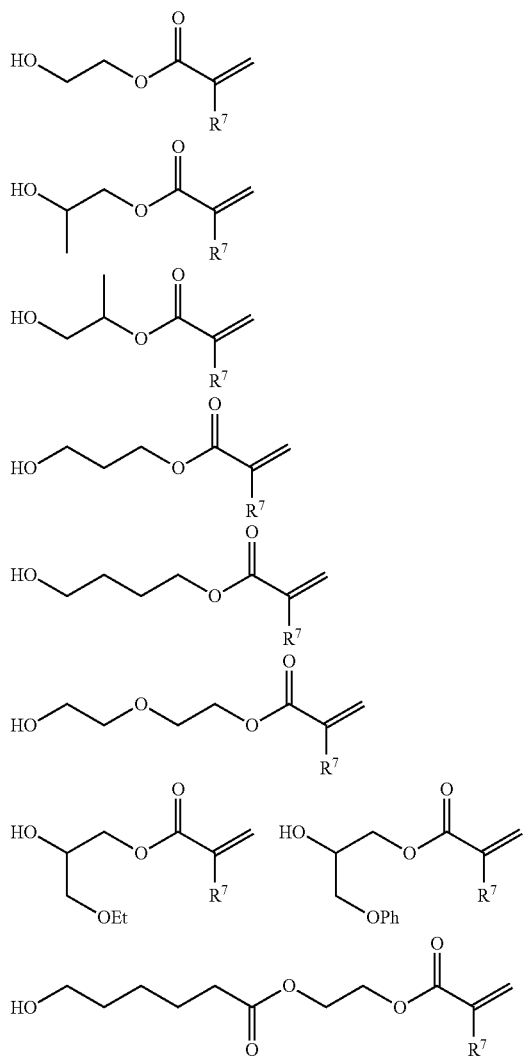

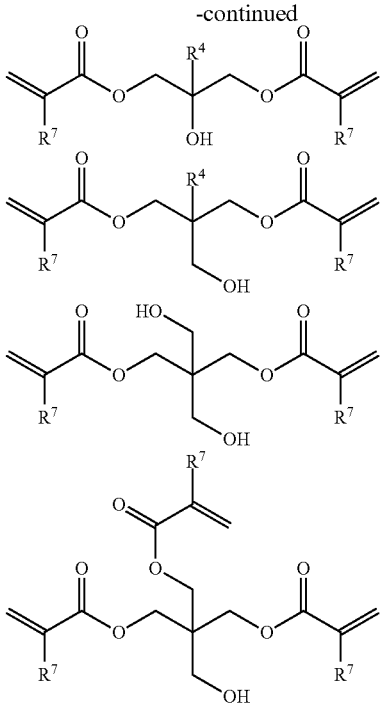

wherein $R^7$ represents a hydrogen atom or a methyl group, Et represents an ethyl group, and Ph represents a phenyl group; and $R^4$ is as defined above.

The urethane acrylate, together with a reactive monomer and a polymerization initiator as necessary, can be polymerized and cured to form a cured product by heating or irradiation with active energy beam, such as ultraviolet ray, visible light, laser beam, electron beam, X-ray, γ-ray, plasma, or microwave.

Examples of the reactive monomer include (meth)acrylic acid aralkyl esters phenyl(meth)acrylates, such as methyl (meth)acrylate, ethyl (meth)acrylate, isopropyl (meth)acrylate, n-butyl (meth)acrylate, t-butyl (meth)acrylate, isobutyl (meth)acrylate, isoamyl (meth)acrylate, lauryl (meth)acrylate, dodecyl (meth)acrylate, stearyl acrylate, cyclohexyl (meth)acrylate, isobornyl (meth)acrylate, adamantyl (meth)acrylate, phenoxymethyl (meth)acrylate, phenoxyethyl (meth)acrylate, benzyl (meth)acrylate and phenethyl (meth)acrylate; monofunctional (meth)acrylate compounds, such as 2-hydroxyethyl (meth)acrylate, 2-hydroxypropyl (meth)acrylate, 3-hydroxypropyl (meth)acrylate, and 4-hydroxybutyl (meth)acrylate; tri(meth)acrylates, such as butanediol di(meth)acrylate, hexanediol di(meth)acrylate, octanediol di(meth)acrylate, nonanediol di(meth)acrylate, dodecanediol di(meth)acrylate, ethoxylated hexanediol di(meth)acrylate, propoxylated hexanediol di(meth)acrylate, diethylene glycol di(meth)acrylate, polyethylene glycol di(meth)acrylate, polypropylene glycol di(meth)acrylate, neopentyl glycol di(meth)acrylate, ethoxylated neopentyl glycol di(meth)acrylate, trimethylolpropane tri(meth)acrylate, ethoxylated trimethylolpropane tri(meth)acrylate, propoxylated trimethylolpropane tri(meth)acrylate, tris(2-hydroxyethyl)isocyanurate tri(meth)acrylate, and glycerin tri(meth)acrylate; polyfunctional (meth)acrylate compounds, such as pentaerythritol tri(meth)acrylate, dipentaerythritol tri(meth)acrylate, ditrimethylolpropane tri(meth)acrylate, pentaerythritol tetra(meth)acrylate, ditrimethylolpropane tetra(meth)acrylate, dipentaerythritol tetra(meth)acrylate, dipentaerythritol penta(meth)acrylate, ditrimethylolpropane penta(meth)acrylate, dipentaerythritol hexa(meth)acrylate, and ditrimethylolpropane hexa(meth)acrylate; and ethyleneoxy-modified products, propyleneoxy-modified products, and lactone-modified products thereof. One of these may be used alone, or two or more thereof may be used in combination.

Examples of the polymerization initiator include acetophenone, 2,2-diethoxyacetophenone, p-dimethylaminoacetophenone, benzophenone, 2-chlorobenzophenone, 4,4'-bisdiethylaminobenzophenone, benzoin ethyl ether, benzoin-n-propyl ether, benzoin isopropyl ether, benzoin isobutyl ether, benzoin-n-butyl ether, benzoin dimethyl ketal, thioxanthone, p-isopropyl-α-hydroxyisobutylphenone, 2,2-dimethoxy-2-phenylacetophenone, 1-hydroxycyclohexyl phenyl ketone, 2-methyl-1-[4-(methylthio)phenyl]-2-morpholinopropan-1-o ne, 2-hydroxy-2-methyl-1-phenylpropan-1-one, 2,4,6-trimethylbenzophenone, 4-methylbenzophenone, (2,4,6-trimethylbenzoyl)-diphenylphosphine oxide, bis(2,4,6-trimethylbenzoyl)-phenylphosphine oxide, 2,2-dimethoxy-1,2-diphenylethanone, and the like. Preferably, 1-hydroxycyclohexyl phenyl ketone or bis(2,4,6-trimethylbenzoyl)phenylphosphine oxide is used. One of these may be used alone, or two or more thereof may be used in combination.

Further, by using the capping agent containing the structures represented by the general formulae (1a) to (1c), the structures represented by the general formulae (1a) to (1c) can be introduced into the polyurethane terminal. Examples of such a capping agent include the following compounds, each of which contains the structure represented by the general formulae (1a) to (1c) above and a hydroxyl group or amino group that can react with isocyanate.

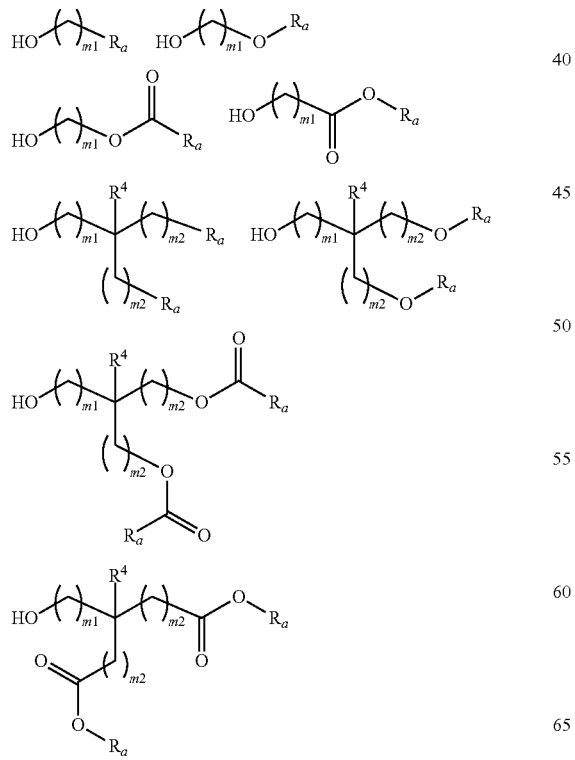

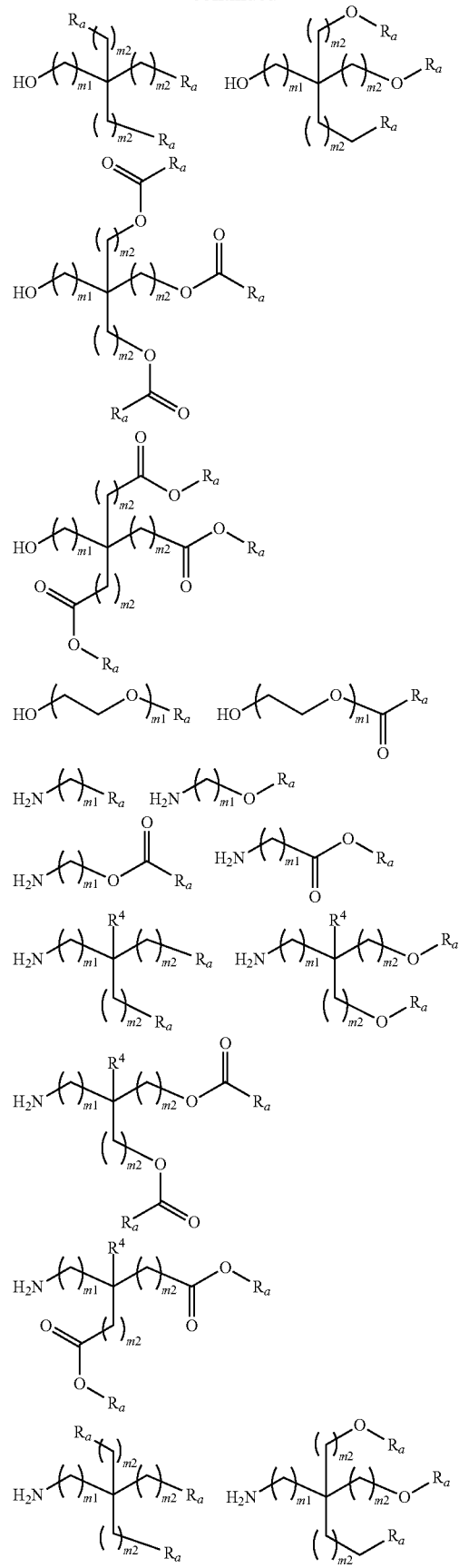

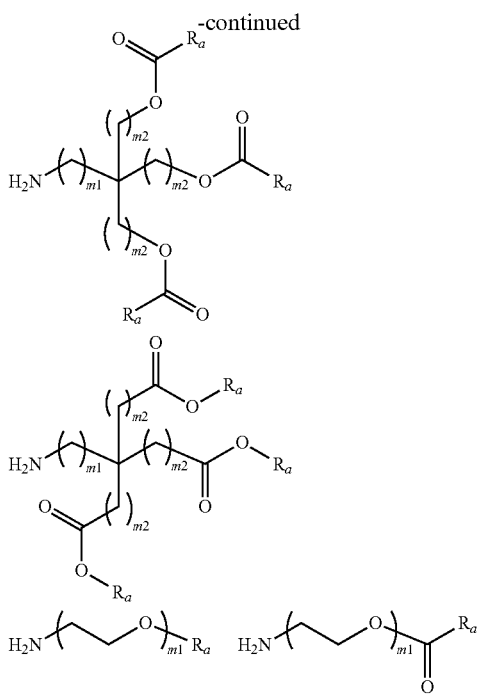

wherein Ra represents the structure represented by the general formulae (3a) to (3c); m1 and m2 each represent an integer of 0 to 20; and $R^4$ is as defined above.

The reaction temperature in the polyurethane synthesis is appropriately changed according to the kind of the reaction substrate. In general, the temperature is preferably 30° C. to 200° C., more preferably 40° C. to 120° C.

The polyurethane has a weight-average molecular weight of preferably 10,000 to 500,000, more preferably 15,000 to 200,000, further preferably 20,000 to 150,000.

In the present embodiments, the polyurethane may further contain, as an additive, an antioxidant, defoamer, ultraviolet absorber, and the like, if necessary.

Conductive Wire

Moreover, the present invention provides a conductive wire, which is formed on a substrate by using the conductive paste composition described above. Moreover, the present invention provides a stretchable conductive wire, which is formed on a stretchable substrate by using the conductive paste composition described above.

The stretchable conductive wire of the present invention is described below in detail; however, the present invention is not limited to the examples described below.

Examples of the substrate on which the stretchable conductive wire is formed include polyurethane, polyester, silicone, nitrile rubber, butadiene rubber, polyethylene, polypropylene, polyolefin, PTFE, PFA, and the like. The substrate is preferably stretchable, and is more preferably a stretchable sheet or film, further preferably a stretchable polyurethane substrate, particularly preferably a thermoplastic polyurethane substrate. The surface of the sheet may be flat or uneven. An uneven surface allows formation of a stretchable wire having a bellows-shaped structure in a direction orthogonal to the substrate, and makes it possible to suppress changes in conductivity at the time of elongation and shrinkage. Alternatively, it is also possible to use a nonwoven fabric or a fabric made of stretchable fibers.

The stretchable substrate preferably has a stretchability of 1000% at maximum. Human skins are known to stretch, according to the movements, by 10% on bones of chest and so forth, by 20% on abdominal portions and so forth, and by 50% on joints. The stretchability required for conductive wires thus vary depending on the attachment location on skin.

A conductive wire made from the conductive paste composition of the present invention is formed on a stretchable substrate. The method for applying such conductive wire onto a stretchable substrate is not particularly limited. Examples of suitable methods include dip coating, spray coating, spin coating, roll coating, flow coating, doctor coating, screen printing, flexographic printing, gravure printing, inkjet printing, and the like. In particular, forming a wire pattern by printing can enhance the productivity and enables flexible design, including wire width.

The conductive wire preferably has a thickness in a range of 10 nm to 1000 μm, more preferably 5 μm to 50 μm.

The conductive paste composition is applied onto a stretchable substrate by printing, followed by baking. The baking temperature is preferably in a range of 60° C. to 160° C., more preferably 120° C. to 150° C., and the baking time is preferably 1 second to 10 hours, more preferably 10 minutes to 5 hours. The baking can be performed on a hot plate or in an oven, or may be performed by flash annealing in a shorter period of time at a higher temperature than the above temperatures. It is also possible to perform the baking by irradiation with infrared light.

The electric conductivity of the stretchable conductive wire can be evaluated by measuring the electric resistance between both ends of the stretchable conductive wire formed on the substrate. The stretchable conductive wire can be evaluated as excellent when the change in electric resistance before and after the elongation of the substrate is small and the degradation of the electric conductivity after the elongated substrate is shrunk and returned to the original shape is small. It is more preferable that when elongations and shrinkages are repeated, no wire breakage occurs and the change in electric resistance is small.

Further, in the conductive wire of the present invention, the electric resistance at 20% elongation is preferably 500& or less relative to the electric resistance before elongation. The lower limit is not particularly limited, and is preferably as low as possible; for example, 150% or more. The maximum electric resistance when elongations and shrinkages are repeated 1000 times at an elongation rate of 20% is preferably 5000% or less relative to the electric resistance before elongation. The lower limit is not particularly limited, and is preferably as low as possible; for example, 300% or more. These electric resistances can be measured according to the measurement method described later.

Further, a cover film may be formed to cover the conductive wire. Forming a cover film can improve the water resistance and mechanical strength. The cover film also needs to be stretchable since both of the substrate and the conductive wire are stretchable. As with the substrate, the material of the cover film can be selected from polyurethane, urethane acrylate, polyester, silicone, nitrile rubber, butadiene rubber, polyethylene, polypropylene, polyolefin, PTFE, PFA, and the like. The cover film to be used preferably has a thickness in a range of 10 nm to 1 mm.

In the conductive paste composition of the present invention, for example, when the conductive filler as the component (A) is a silver powder, it is presumed that a silver salt is formed by the functional groups represented by the general formulae (1a) to (1c) in the elastomer as the component (C) and an oxide film of the silver powder, and the silver salt is reduced by heat or the like to form silver nanoparticles. Furthermore, it is also presumed that the phenol compound as the component (B) is also weakly acidic, and forms a silver salt with the oxide film of the silver powder, thereby generating silver nanoparticles by reduction in the same manner as described above. In addition, when the phenol compound as the component (B) is the phenol compound of the general formula (1A) or (1B), the compound has a fluorine atom on the aromatic ring, and a nucleophilic substitution reaction occurs between the fluorine atom and the silver salt, and silver fluoride is formed as a by-product during the process. It is presumed that this silver fluoride is reduced by heat or the like to form silver nanoparticles.

In the conductive wire formed by using the conductive paste composition of the present invention, it is presumed that silver nanoparticles are generated through the three routes as described above in the baking process of the wire, and the generated silver nanoparticles are dispersed in the insulating polymer between the silver powder particles, whereby the conductive wire exhibits high electric conductivity. Furthermore, even when the distances among the silver powder particles are increased as a result of the wire elongation, the electric conduction path is not easily cut off because of the silver nanoparticles dispersed among the silver powder particles. Therefore, the wire does not easily break, and the electric conductivity varies only slightly.

EXAMPLES

The present invention is more specifically described below with reference to Examples and Comparative Examples. However, the present invention is not limited to these Examples. Note that, in the formulae below, Me represents a methyl group, and the weight average molecular weight (Mw) and the number average molecular weight (Mn) were measured on polystyrene basis by gel permeation chromatography (GPC). The GPC measurement conditions are as follows.

Column: TSKgel G4000H$_{XL}$, TSKgel G3000H$_{XL}$, TSKgel G2000H$_{XL}$(two)
Mobile phase: tetrahydrofuran
Column oven temperature: 40° C.
Sample concentration: 0.20 mass %
Sample injection amount: 100 μL
Flow rate: 1 mL/min Example 1

The phenol compound of the present invention was synthesized by the following method.

Example 1-1: Synthesis of Phenol 1

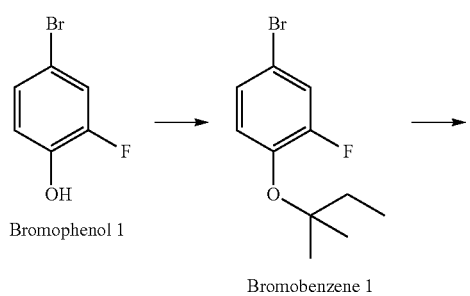

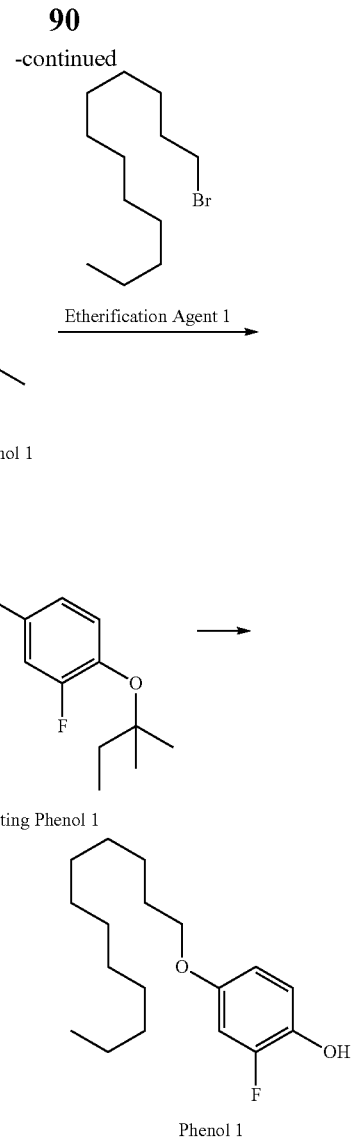

Example 1-1-1: Synthesis of Bromobenzene 1

In an atmosphere of nitrogen, methanesulfonic acid (4.8 g) was added to bromophenol 1 (76.4 g) and isoamylene (112.2 g) dissolved in toluene (10 g) at −20° C. to −10° C. After stirring at the same temperature for 3 hours, triethylamine (10.1 g) and then a 25 mass % of caustic soda (32.0 g) were added dropwise to stop the reaction. A typical aqueous work-up was performed. By distillation under reduced pressure, bromobenzene 1 (84.6 g, yield=81%) was obtained.
Boiling point: 67° C./10 Pa Example 1-1-2: Synthesis of Intermediate Phenol 1

In an atmosphere of nitrogen, a Grignard reagent prepared in advance by using bromobenzene 1 (52.2 g), magnesium (5.1 g), and 140 mL of tetrahydrofuran was added dropwise to a solution of trimethyl borate (22.9 g) and tetrahydrofuran (310 mL) at an internal temperature of −5° C. or less. The stirring was continued at a reaction temperature of 5° C. for 3 hours. Thereafter, at an internal temperature of 30° C. or less, acetic acid (18.0 g) and 35% hydrogen peroxide (25.3 g) were added. The stirring was continued at room temperature for 3 hours, followed by an ordinary post-treatment method and recrystallization with a mixed solution of toluene/n-hexane to obtain an intermediate phenol 1 (29.7 g, yield=75%).

IR (D-ATR): ν=3233, 3071, 2941, 2929, 2853, 1622, 1601, 1512, 1480, 1465, 1447, 1378, 1334, 1311, 1205, 1196, 1158, 1111, 1097, 975, 966, 870, 816 cm$^{-1}$.

$^1$H-NMR (600 MHz in DMSO-d6): δ=9.52 (1H, s), 6.88 (1H, t), 6.55 (1H, dd), 6.46 (1H, dd), 1.62 (2H, q), 1.14 (6H, s), 0.93 (3H, t) ppm.

$^{19}$F-NMR (565 MHz in DMSO-d6): δ=−126.6 (1F, s) ppm.

Example 1-1-3: Synthesis of Protecting Phenol 1

In an atmosphere of nitrogen, etherification agent 1 (20.9 g) was added to a slurry solution of the intermediate phenol 1 (13.9 g), potassium carbonate (10.6 g), sodium iodide (100 mg), and dimethylformaldehyde (50 g) at 60° C. to 80° C. After stirring at the same temperature for 6 hours, water (100 g) was added dropwise to stop the reaction. A typical aqueous work-up was performed to obtain a protecting phenol 1 (24.5 g, yield=95%).

Example 1-1-4: Synthesis of Phenol 1

A solution of the protecting phenol 1 (7.3 g) thus obtained, p-toluenesulfonic acid monohydrate (0.1 g), and toluene (20 mL) was continuously heated and stirred at an internal temperature of 70° C. to 90° C. for 4 hours. Thereafter, at an internal temperature of 30° C. or less, 15 g of water was added to stop the reaction. An ordinary post-treatment method was performed, followed by recrystallization with a mixed solution of toluene/n-hexane to obtain phenol 1 (5.0 g, yield=84).

IR (D-ATR): ν=3402, 2953, 2942, 2920, 2870, 2854, 1607, 1516, 1479, 1471, 1460, 1398, 1313, 1275, 1255, 1205, 1158, 1111, 1028, 840, 788 cm$^{-1}$.

$^1$H-NMR (600 MHz in DMSO-d6): δ=9.18 (1H, s), 6.82 (1H, t), 6.72 (1H, dd), 6.54 (1H, dd), 3.82 (2H, t), 1.62 (2H, m), 1.14-1.38 (18H, m), 0.83 (3H, t) ppm.

$^{19}$F-NMR (565 MHz in DMSO-d6): δ=−133.7 (1F, t) ppm.

Example 1-2: Synthesis of Phenol 2

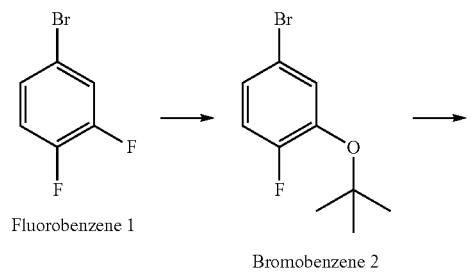

Fluorobenzene 1

Bromobenzene 2

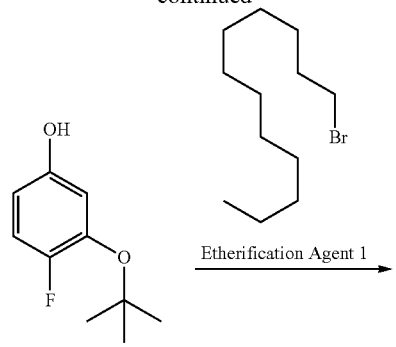

Intermediate Phenol 2

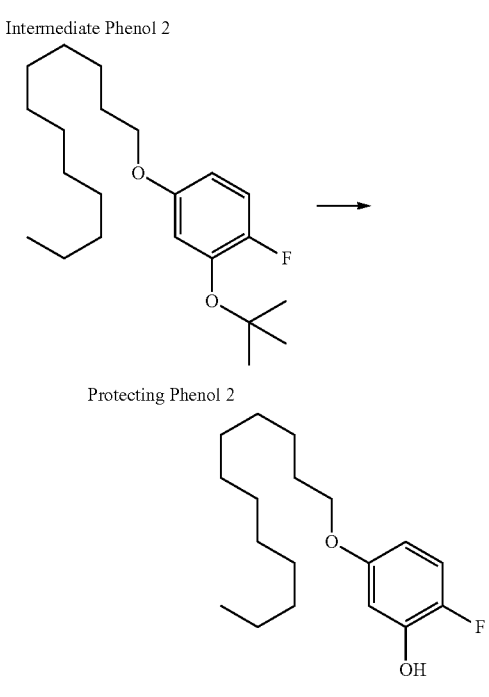

Protecting Phenol 2

Phenol 2

Example 1-2-1: Synthesis of Bromobenzene 2

In an atmosphere of nitrogen, fluorobenzene 1 (100 g) was added dropwise to t-butoxy potassium (63.9 g) dissolved in THF (360 g) at 0° C. to 10° C. After stirring at the same temperature for 10 hours, water (150 g) was added dropwise to stop the reaction. A typical aqueous work-up was performed. By distillation under reduced pressure, bromobenzene 2 (98.6 g, yield=77%) was obtained.

Boiling point: 97-100° C./700 Pa

Example 1-2-2: Synthesis of Intermediate Phenol 2

Intermediate phenol 2 was obtained in the same manner as in Example 1-1-2, except that bromobenzene 2 was used instead of bromobenzene 1 (yield=77%).

Example 1-2-3: Synthesis of Protecting Phenol 2

Protecting phenol 2 was obtained in the same manner as in Example 1-1-3, except that intermediate phenol 2 was used instead of intermediate phenol 1 (yield=92%).

Example 1-2-4: Synthesis of Phenol 2

Phenol 2 was obtained in the same manner as in Example 1-1-4, except that protecting phenol 2 was used instead of protecting phenol 1 (yield=80%).

Example 1-3: Synthesis of Phenol 3

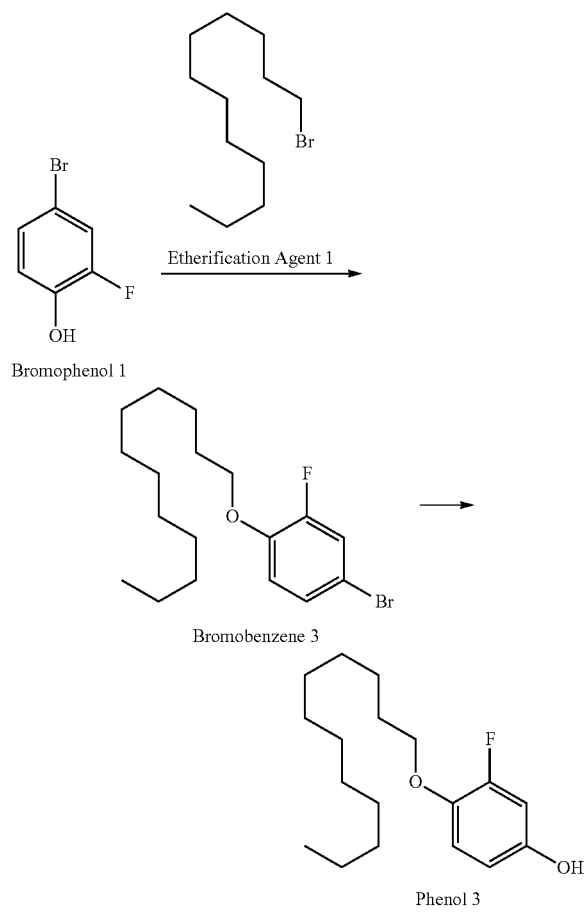

Example 1-3-1: Synthesis of Bromobenzene 3

Bromobenzene 3 was obtained in the same manner as in Example 1-1-3, except that bromophenol 1 was used instead of intermediate phenol 1 (yield=94%).

Example 1-3-2: Synthesis of Phenol 3

Phenol 3 was obtained in the same manner as in Example 1-1-2, except that bromobenzene 3 was used instead of bromobenzene 1 (yield=74%).

IR (D-ATR): ν=3404, 2957, 2918, 2872, 2850, 1599, 1523, 1482, 1470, 1455, 1400, 1376, 1305, 1288, 1239, 1219, 1153, 1115, 1026, 964, 851, 811, 800 cm$^{-1}$.

$^1$H-NMR (600 MHz in DMSO-d6): δ=9.31 (1H, s), 6.90 (1H, t), 6.55 (1H, dd), 6.47 (1H, dd), 3.86 (2H, t), 1.63 (2H, m), 1.16-1.39 (18H, m), 0.83 (3H, t) ppm.

$^{19}$F-NMR (565 MHz in DMSO-d6): δ=−132.4 (1F, t) ppm.

Example 1-4: Synthesis of Phenol 4

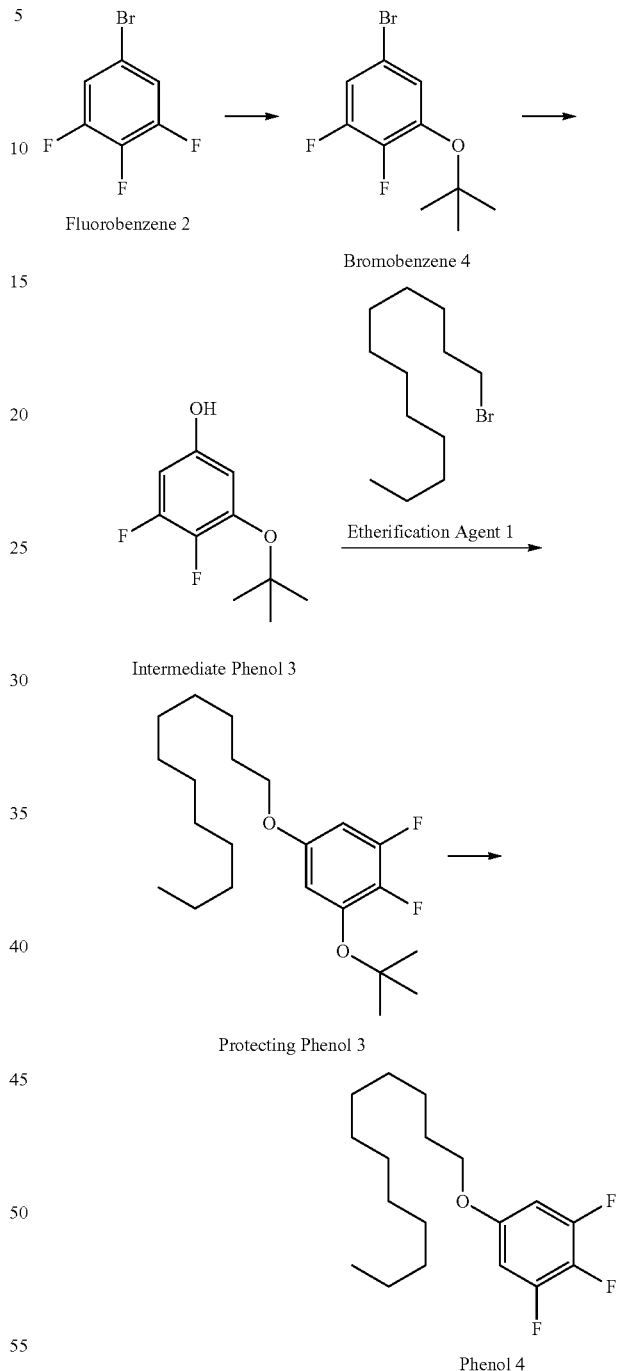

Example 1-4-1: Synthesis of Bromobenzene 4

Bromobenzene 4 was obtained in the same manner as in Example 1-2-1, except that fluorobenzene 2 was used instead of fluorobenzene 1 (yield=94%).

Boiling point: 82-84° C./300 Pa

Example 1-4-2: Synthesis of Intermediate Phenol 3

Intermediate phenol 3 was obtained in the same manner as in Example 1-1-2, except that bromobenzene 4 was used instead of bromobenzene 1 (yield=62%).

Example 1-4-3: Synthesis of Protecting Phenol 3

Protecting phenol 3 was obtained in the same manner as in Example 1-1-3, except that intermediate phenol 3 was used instead of intermediate phenol 1 (yield=88).

Example 1-4-4: Synthesis of Phenol 4

Phenol 4 was obtained in the same manner as in Example 1-1-4, except that protecting phenol 3 was used instead of protecting phenol 1 (yield=72%).

IR (D-ATR): ν=3423, 2954, 2942, 2920, 2853, 1639, 1616, 1531, 1478, 1472, 1379, 1400, 1379, 1244, 1214, 1152, 1054, 1032, 1020, 828, 822, 809, 789 cm$^{-1}$.

$^{1}$H-NMR (only main isomers, 600 MHz in DMSO-d6): δ=10.32 (1H, s), 6.38 (1H, m), 6.27 (1H, m), 3.82 (2H, t), 1.63 (2H, m), 1.16-1.40 (18H, m), 0.82 (3H, t) ppm.

$^{19}$F-NMR (only main isomers, 565 MHz in DMSO-d6): δ=−137.4 (1F, m), −171.7 (1F, m) ppm.

Example 1-5: Synthesis of Phenol 5

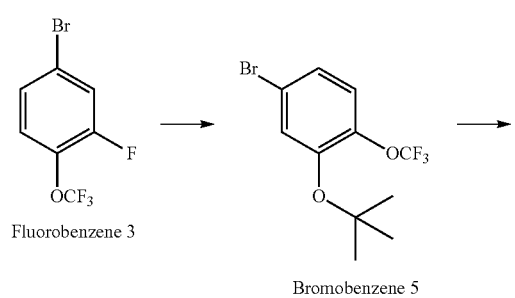

Fluorobenzene 3 → Bromobenzene 5

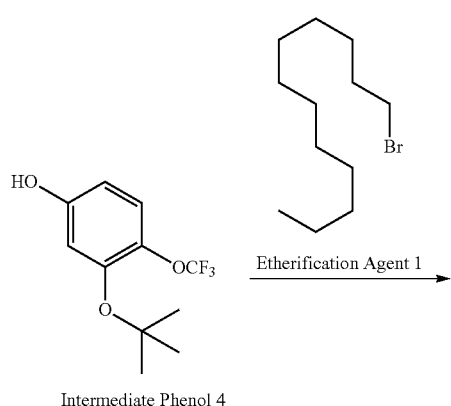

Intermediate Phenol 4

Etherification Agent 1

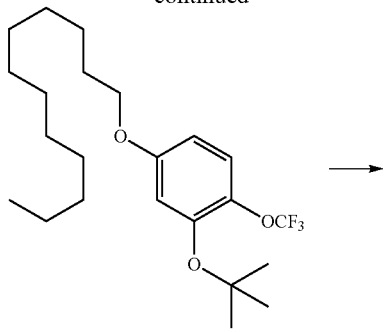

Protecting Phenol 4

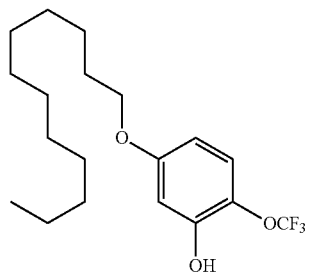

Phenol 5

Example 1-5-1: Synthesis of Bromobenzene 5

Bromobenzene 5 was obtained in the same manner as in Example 1-2-1, except that fluorobenzene 3 was used instead of fluorobenzene 1 (yield=77%).

Boiling point: 99-100° C./1 KPa

Example 1-5-2: Synthesis of Intermediate Phenol 4

Intermediate phenol 4 was obtained in the same manner as in Example 1-1-2, except that bromobenzene 5 was used instead of bromobenzene 1 (yield=68%).

Example 1-5-3: Synthesis of Protecting Phenol 4

Protecting phenol 4 was obtained in the same manner as in Example 1-1-3, except that intermediate phenol 4 was used instead of intermediate phenol 1 (yield=90%).

Example 1-5-4: Synthesis of Phenol 5

Phenol 5 was obtained in the same manner as in Example 1-1-4, except that protecting phenol 4 was used instead of protecting phenol 1 (yield=81').

IR (D-ATR): ν=3591, 3446, 2926, 2855, 1605, 1507, 1468, 1391, 1254, 1204, 1172, 1026, 983, 912, 836, 792 cm$^{-1}$.

$^{1}$H-NMR (600 MHz in DMSO-d6): δ=10.06 (1H, s), 7.08 (1H, d), 6.49 (1H, d), 6.34 (1H, dd), 3.86 (2H, t), 1.64 (2H, m), 1.15-1.38 (18H, m), 0.83 (3H, t) ppm.

$^{19}$F-NMR (565 MHz in DMSO-d6): δ=−57.5 (3F, t) ppm.

Example 1-6: Synthesis of Phenol 6

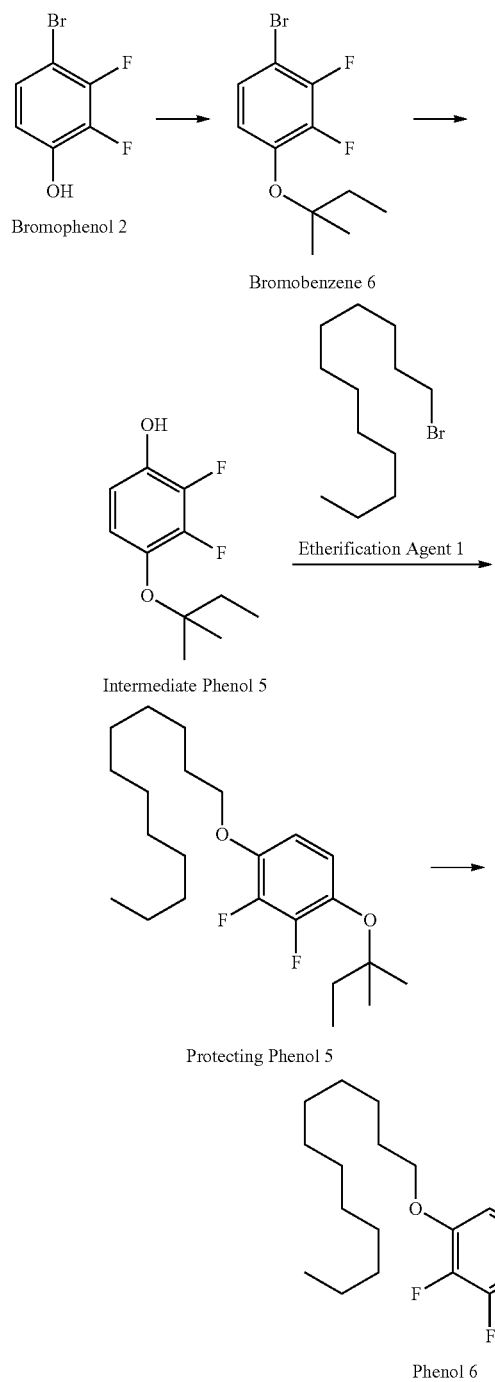

Intermediate Phenol 5

Protecting Phenol 5

Phenol 6

Example 1-6-1: Synthesis of Bromobenzene 6

Bromobenzene 6 was obtained in the same manner as in Example 1-1-1, except that bromophenol 2 was used instead of bromophenol 1 (yield=77%).

Boiling point: 66° C./6 Pa

Example 1-6-2: Synthesis of Intermediate Phenol 5

Intermediate phenol 5 was obtained in the same manner as in Example 1-1-2, except that bromobenzene 6 was used instead of bromobenzene 1 (yield=62%).

Example 1-6-3: Synthesis of Protecting Phenol 5

Protecting phenol 5 was obtained in the same manner as in Example 1-1-3, except that intermediate phenol 5 was used instead of intermediate phenol 1 (yield=91%).

Example 1-6-4: Synthesis of Phenol 6

Phenol 6 was obtained in the same manner as in Example 1-1-4, except that protecting phenol 5 was used instead of protecting phenol 1 (yield=76%).

IR (D-ATR): ν=3290, 2956, 2918, 2873, 2849, 1615, 1526, 1502, 1470, 1420, 1398, 1284, 1265, 1216, 1180, 1089, 1062, 1053, 1042, 1030, 1016, 975, 945, 802 $cm^{-1}$.

$^{1}$H-NMR (600 MHz in DMSO-d6): δ=9.74 (1H, s), 6.70 (2H, dt), 3.91 (2H, t), 1.64 (2H, m), 1.32-1.39 (2H, m), 1.16-1.32 (16H, m), 0.82 (3H, t) ppm.

$^{19}$F-NMR (565 MHz in DMSO-d6): δ=−158.1~−157.9 (1F, m), −159.3~−159.1 (1F, m) ppm.

Example 1-7: Synthesis of Phenol 7

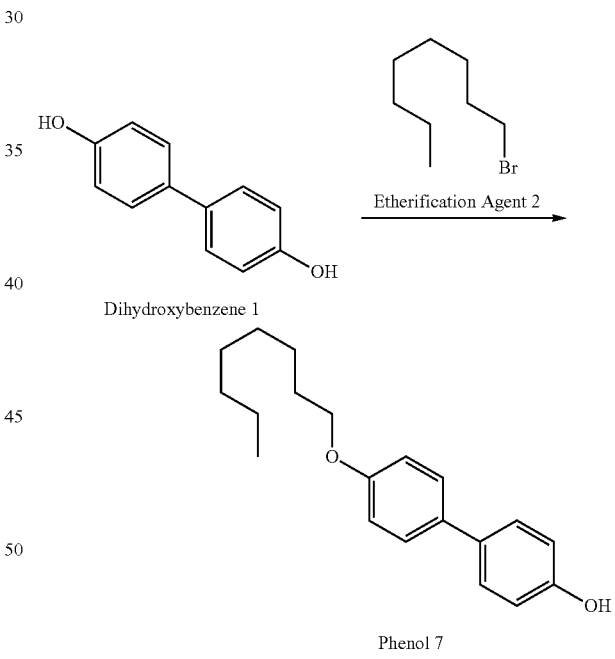

Dihydroxybenzene 1

Phenol 7

Example 1-7-1: Synthesis of Phenol 7

In an atmosphere of nitrogen, etherification agent 2 (19.3 g) was added to a slurry solution of dihydroxybenzene 1 (55.9 g), potassium carbonate (41.5 g), sodium iodide (100 mg), and dimethylformaldehyde (300 g) at 60° C. to 80° C. After stirring at the same temperature for 3 hours, water (400 g) was added dropwise to stop the reaction. A typical aqueous work-up was performed. Recrystallization was performed with a mixed solution of ethyl acetate/n-hexane to obtain phenol 7 (15.4 g, yield=52%).

Example 1-8: Synthesis of Phenol 8

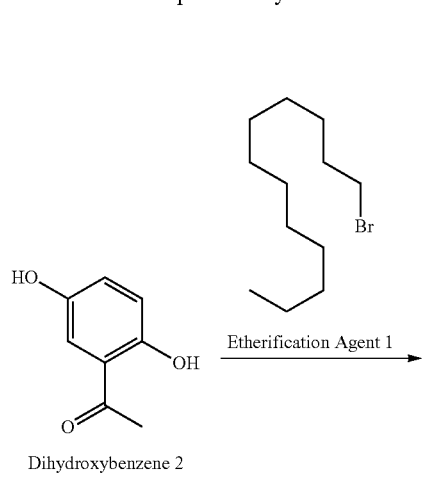

Dihydroxybenzene 2

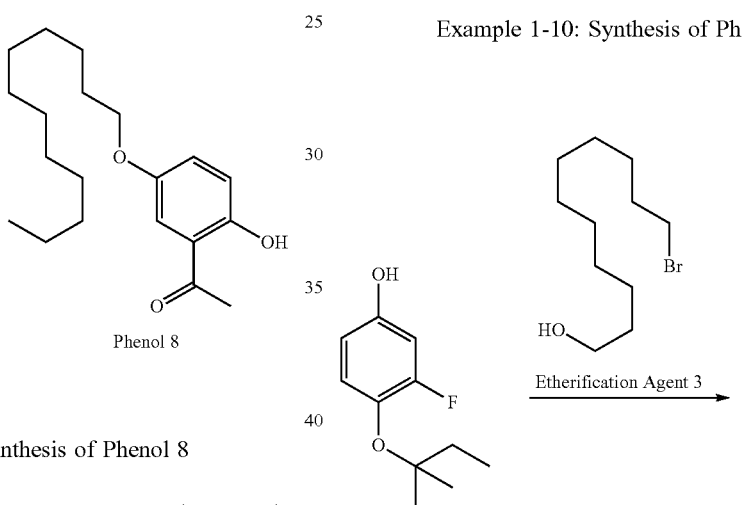

Phenol 8

Example 1-8-1: Synthesis of Phenol 8

Phenol 8 was obtained in the same manner as in Example 1-7-1, except that dihydroxybenzene 2 was used instead of dihydroxybenzene 1, and etherification agent 1 was used instead of etherification agent 2 (yield=43%).

Example 1-9: Synthesis of Phenol 9

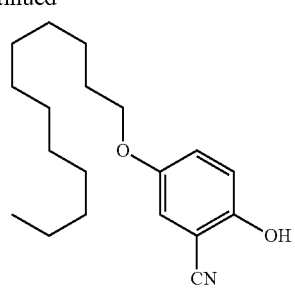

Dihydroxybenzene 3

Phenol 9

Example 1-9-1: Synthesis of Phenol 9

Phenol 9 was obtained in the same manner as in Example 1-7-1, except that dihydroxybenzene 3 was used instead of dihydroxybenzene 1, and etherification agent 1 was used instead of etherification agent 2 (yield=40%).

Example 1-10: Synthesis of Phenol 10

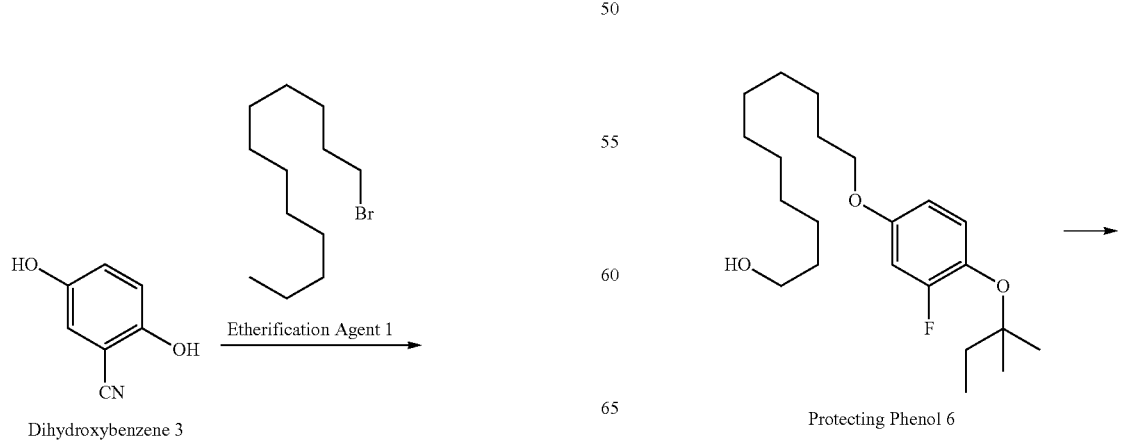

Intermediate Phenol 1

Protecting Phenol 6

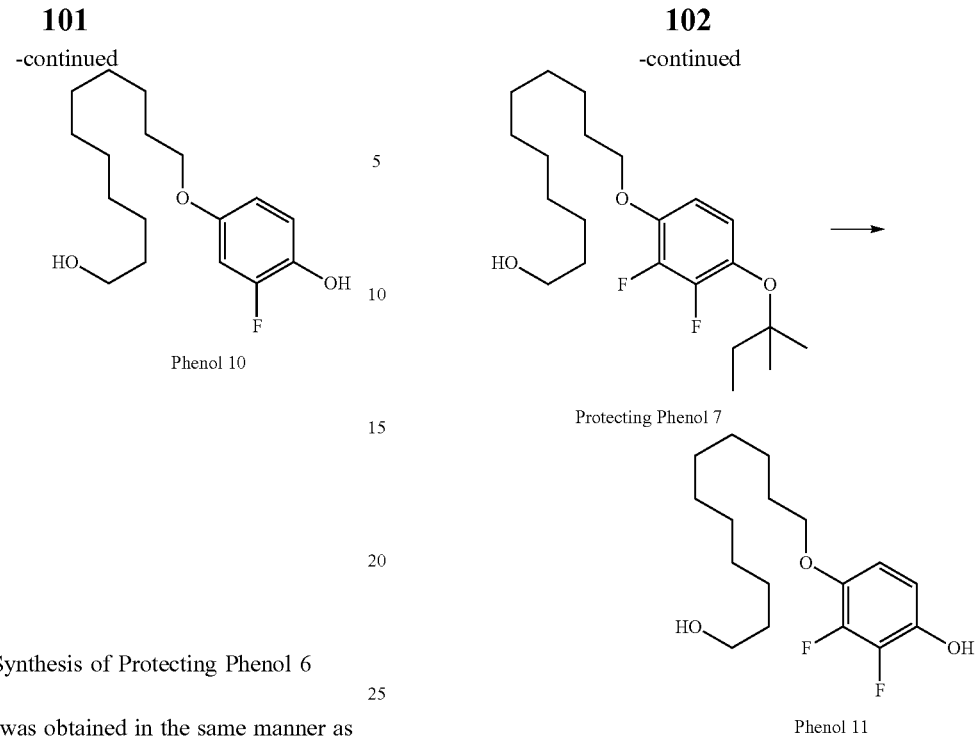

Phenol 10

Phenol 11

Example 1-10-1: Synthesis of Protecting Phenol 6

Protecting phenol 6 was obtained in the same manner as in Example 1-1-3, except that etherification agent 3 was used instead of etherification agent 1 (yield=83%).

Example 1-10-2: Synthesis of Phenol 10

Phenol 10 was obtained in the same manner as in Example 1-1-4, except that protecting phenol 6 was used instead of protecting phenol 1 (yield=92%).

IR (D-ATR): ν=3483, 3189, 2919, 2852, 1605, 1521, 1477, 1468, 1449, 1395, 1313, 1275, 1263, 1243, 1205, 1163, 1113, 1046, 1032, 1008, 955, 864, 840, 799, 788 cm$^{-1}$.

$^1$H-NMR (600 MHz in DMSO-d6): δ=9.18 (1H, s), 6.82 (1H, t), 6.74 (1H, dd), 6.54 (1H, dd), 4.29 (1H, s), 3.83 (2H, t), 3.36 (2H, t), 1.63 (2H, m), 1.16-1.44 (16H, m) ppm.

$^{19}$F-NMR (565 MHz in DMSO-d6): δ=−133.7 (1F, t) ppm.

Example 1-11: Synthesis of Phenol 11

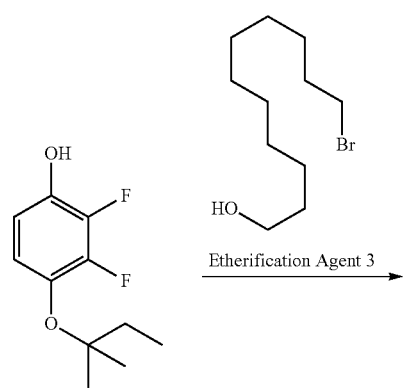

Intermediate Phenol 5

Etherification Agent 3

Example 1-11-1: Synthesis of Protecting Phenol 7

Protecting phenol 7 was obtained in the same manner as in Example 1-1-3, except that intermediate phenol 5 was used instead of intermediate phenol 1, and etherification agent 3 was used instead of etherification agent 1 (yield=82%).

Example 1-11-2: Synthesis of Phenol 11

Phenol 11 was obtained in the same manner as in Example 1-1-4, except that protecting phenol 7 was used instead of protecting phenol 1 (yield=92%).

IR (D-ATR): ν=3494, 3215, 2932, 2918, 2849, 1613, 1526, 1503, 1480, 1470, 1434, 1400, 1287, 1264, 1212, 1183, 1091, 1077, 1054, 1020, 1004, 967, 942, 804 cm$^{-1}$.

$^1$H-NMR (600 MHz in DMSO-d6): δ=9.75 (1H, s), 6.70 (2H, dt), 4.28 (1H, t), 3.92 (2H, t), 3.35 (2H, m), 1.65 (2H, m), 1.32-1.42 (4H, m), 1.20-1.32 (12H, m) ppm.

$^{19}$F-NMR (565 MHz in DMSO-d6): δ=−158.1∼−157.9 (1F, m), −159.3∼−159.1 (1F, m) ppm.

Example 1-12: Synthesis of Phenol 12

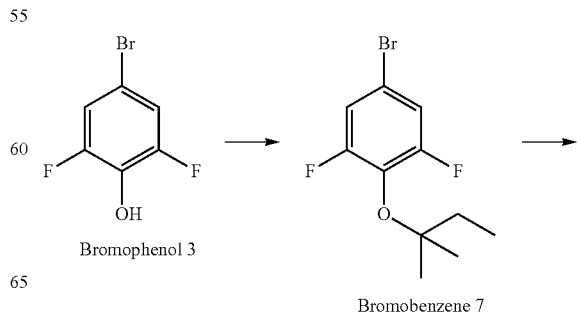

Bromophenol 3

Bromobenzene 7

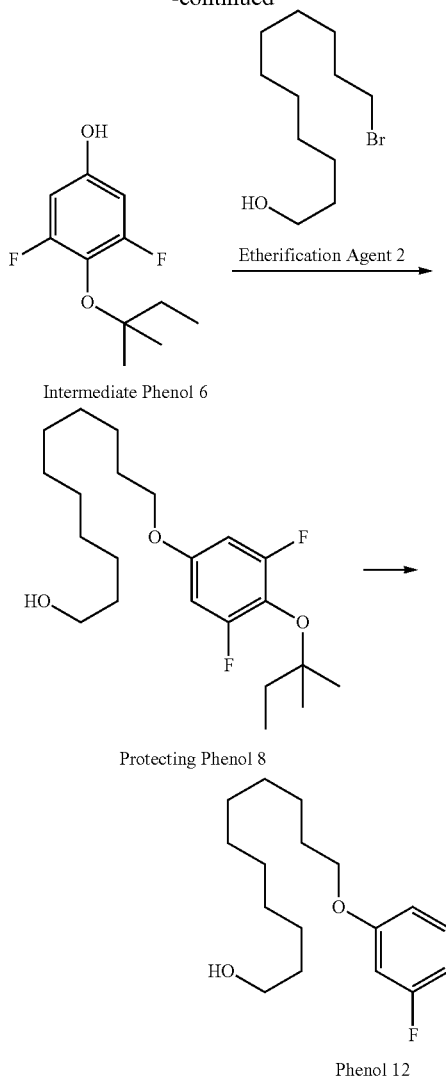

Intermediate Phenol 6

Protecting Phenol 8

Phenol 12

Example 1-12-1: Synthesis of Bromobenzene 7

Bromobenzene 7 was obtained in the same manner as in Example 1-1-1, except that bromophenol 3 was used instead of bromophenol 1 (yield=72%).
Boiling point: 53° C./15 Pa

Example 1-12-2: Synthesis of Intermediate Phenol 6

Intermediate phenol 6 was obtained in the same manner as in Example 1-1-2, except that bromobenzene 7 was used instead of bromobenzene 1 (yield=64%).
$^1$H-NMR (600 MHz in DMSO-d6): δ=9.99 (1H, s), 6.44 (2H, m), 1.62 (2H, m), 1.15 (6H, s), 0.94 (3H, t) ppm.
$^{19}$F-NMR (565 MHz in DMSO-d6): δ=−122.9 (2F, d) ppm.

Example 1-12-3: Synthesis of Protecting Phenol 8

Protecting phenol 8 was obtained in the same manner as in Example 1-1-3, except that intermediate phenol 6 was used instead of intermediate phenol 1, and etherification agent 3 was used instead of etherification agent 1 (yield=89%).

Example 1-12-4: Synthesis of Phenol 12

Phenol 12 was obtained in the same manner as in Example 1-1-4, except that protecting phenol 8 was used instead of protecting phenol 1 (yield=73%).
IR (D-ATR): ν=3532, 3101, 2922, 2853, 2801, 1649, 1613, 1530, 1468, 1457, 1426, 1397, 1268, 1254, 1239, 1200, 1156, 1046, 1036, 1018, 855, 817, 804 cm$^{-1}$.
$^1$H-NMR (600 MHz in DMSO-d6): δ=9.38 (1H, s), 6.63 (2H, m), 4.30 (1H, s), 3.85 (2H, t), 3.36 (2H, t), 1.63 (2H, m), 1.32-1.42 (4H, m), 1.20-1.32 (12H, m) ppm.
$^{19}$F-NMR (565 MHz in DMSO-d6): δ=−131.0 (1F, d) ppm.

Example 1-13: Synthesis of Phenol 13

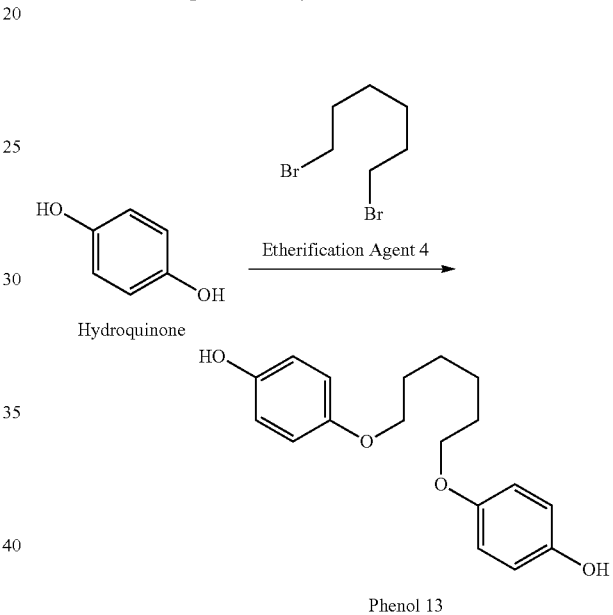

Hydroquinone

Phenol 13

Example 1-13-1: Synthesis of Phenol 13

Phenol 13 was obtained in the same manner as in Example 1-7-1, except that hydroquinone was used instead of dihydroxybenzene 1, and etherification agent 4 was used instead of etherification agent 2 (yield=59%).

Example 1-14: Synthesis of Phenol 14

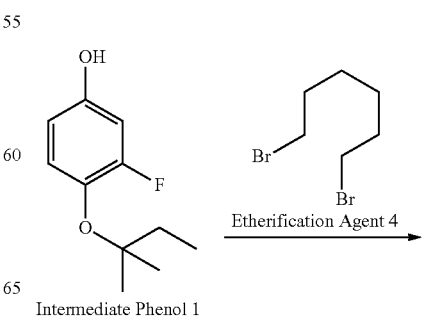

Intermediate Phenol 1

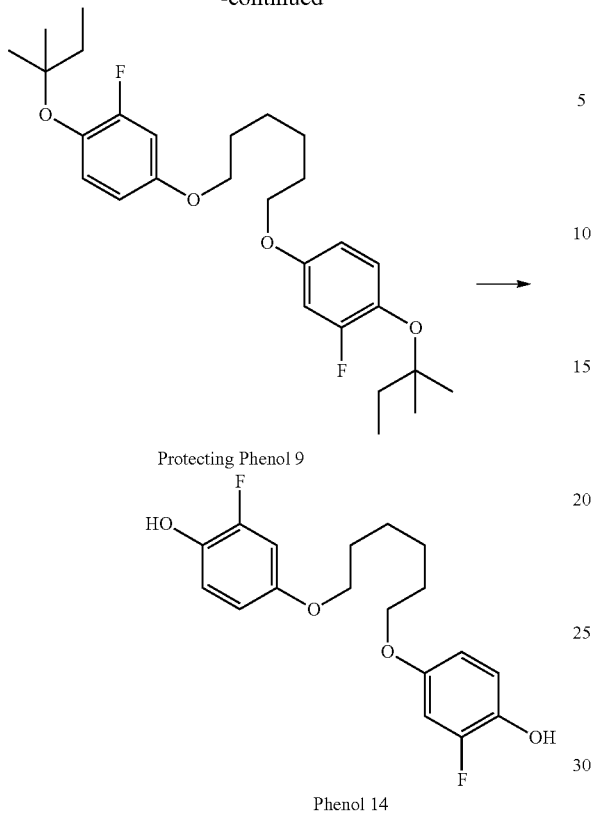

Protecting Phenol 9

Phenol 14

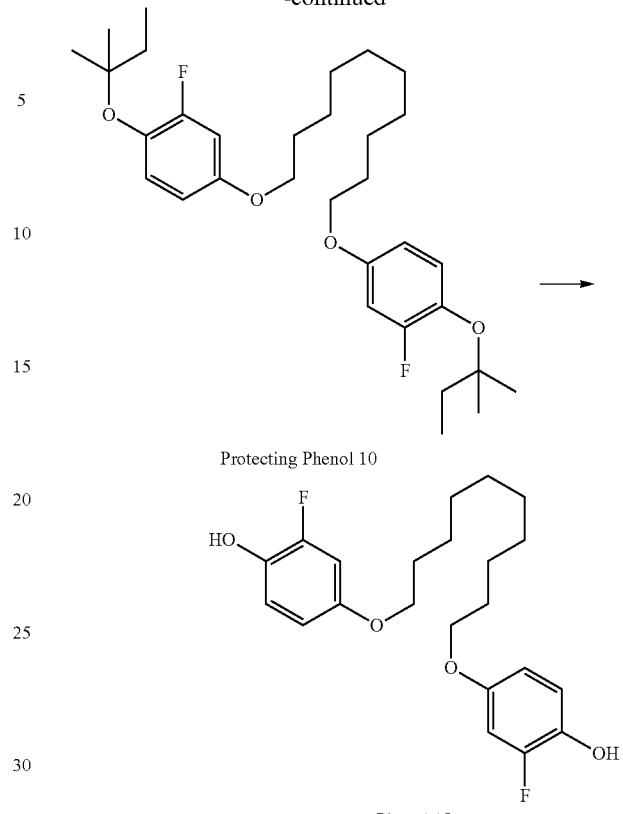

Protecting Phenol 10

Phenol 15

Example 1-14-1: Synthesis of Protecting Phenol 9

Protecting phenol 9 was obtained in the same manner as in Example 1-1-3, except that etherification agent 4 was used instead of etherification agent 1 (yield=94%).

Example 1-14-2: Synthesis of Phenol 14

Phenol 14 was obtained in the same manner as in Example 1-1-4, except that protecting phenol 9 was used instead of protecting phenol 1 (yield=90%).

IR (D-ATR): ν=3380, 2944, 2869, 1642, 1606, 1516, 1477, 1446, 1394, 1368, 1317, 1263, 1242, 1195, 1162, 1109, 1023, 969, 956, 867, 838, 796 cm$^{-1}$.

$^1$H-NMR (600 MHz in DMSO-d6): δ=9.19 (2H, s), 6.82 (2H, t), 6.75 (2H, dd), 6.55 (2H, dd), 3.85 (4H, t), 1.66 (4H, quin), 1.42 (4H, m) ppm.

$^{19}$F-NMR (565 MHz in DMSO-d6): δ=−133.6 (2F, t) ppm.

Example 1-15: Synthesis of Phenol 15

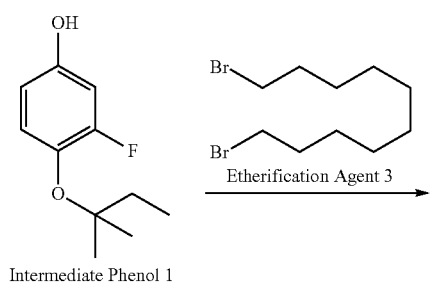

Intermediate Phenol 1

Etherification Agent 3

Example 1-15-1: Synthesis of Protecting Phenol 10

Protecting phenol 10 was obtained in the same manner as in Example 1-1-3, except that etherification agent 5 was used instead of etherification agent 1 (yield=92%).

Example 1-15-2: Synthesis of Phenol 15

Phenol 15 was obtained in the same manner as in Example 1-1-4, except that protecting phenol 10 was used instead of protecting phenol 1 (yield=87%).

IR (D-ATR): ν=3385, 2941, 2923, 2856, 1608, 1514, 1479, 1468, 1455, 1288, 1276, 1253, 1203, 1156, 1110, 1042, 1022, 988, 956, 842, 818, 802, 787, 748 cm$^{-1}$.

$^1$H-NMR (600 MHz in DMSO-d6): δ=9.18 (2H, s), 6.82 (2H, t), 6.74 (2H, dd), 6.55 (2H, dd), 3.83 (4H, t), 1.66 (4H, quin), 1.20-1.41 (12H, m) ppm.

$^{19}$F-NMR (565 MHz in DMSO-d6): δ=−133.7 (2F, t) ppm.

Example 1-16: Synthesis of Phenol 16

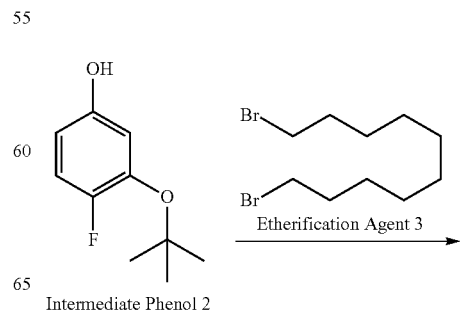

Intermediate Phenol 2

Etherification Agent 3

-continued

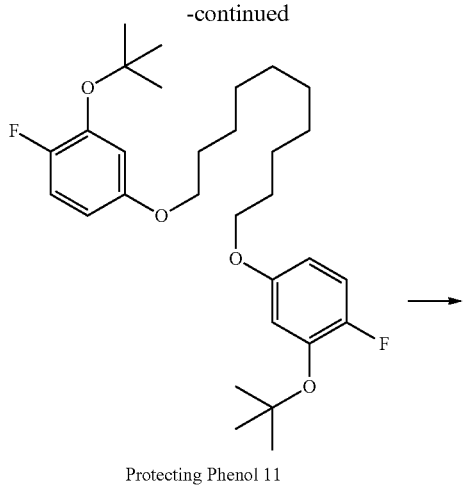

Protecting Phenol 11

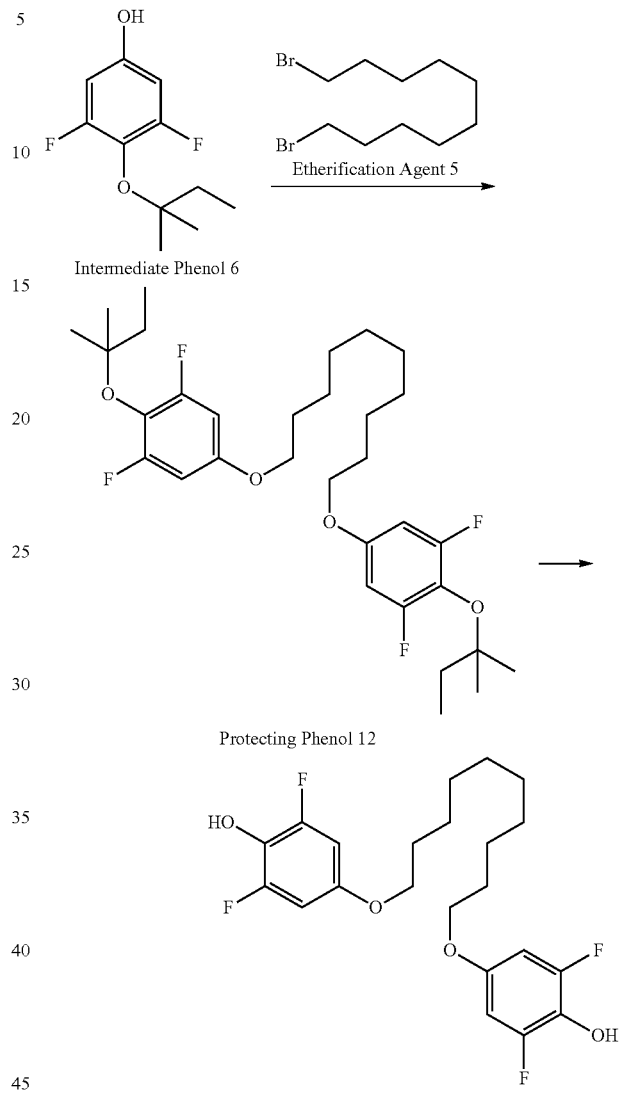

Phenol 16

Example 1-16-1: Synthesis of Protecting Phenol 11

Protecting phenol 11 was obtained in the same manner as in Example 1-1-3, except that intermediate phenol 2 was used instead of intermediate phenol 1, and etherification agent 5 was used instead of etherification agent 1 (yield=89%).

Example 1-16-2: Synthesis of Phenol 16

Phenol 16 was obtained in the same manner as in Example 1-1-4, except that protecting phenol 11 was used instead of protecting phenol 1 (yield=85%).

IR (D-ATR): ν=3562, 3537, 3417, 2941, 2921, 2884, 2868, 2854, 1706, 1623, 1615, 1531, 1516, 1477, 1466, 1445, 1396, 1350, 1299, 1256, 1229, 1184, 1161, 1112, 1045, 1021, 983, 931, 854, 838, 786, 772, 757 cm$^{-1}$.

$^{1}$H-NMR (600 MHz in DMSO-d6): δ=9.76 (2H, s), 6.97 (2H, t), 6.46 (2H, dd), 6.27 (2H, dd), 3.82 (4H, t), 1.64 (4H, quin), 1.21-1.40 (12H, m) ppm.

$^{19}$F-NMR (565 MHz in DMSO-d6): δ=−146.6~−146.5 (2F, m) ppm.

Example 1-17: Synthesis of Phenol 17

Example 1-17-1: Synthesis of Protecting Phenol 12

Protecting phenol 12 was obtained in the same manner as in Example 1-1-3, except that intermediate phenol 6 was used instead of intermediate phenol 1, and etherification agent 5 was used instead of etherification agent 1 (yield=88%).

Example 1-17-2: Synthesis of Phenol 17

Phenol 17 was obtained in the same manner as in Example 1-1-4, except that protecting phenol 12 was used instead of protecting phenol 1 (yield=84%).

IR (D-ATR): ν=3401, 2942, 2923, 2856, 1648, 1616, 1528, 1479, 1469, 1459, 1378, 1247, 1202, 1148, 1045, 1023, 1017, 823, 802 cm$^{31}$.

$^1$H-NMR (600 MHz in DMSO-d6): δ=9.38 (2H, s), 6.64 (4H, m), 3.85 (4H, t), 3.36 (2H, t), 1.64 (4H, m), 1.32-1.42 (4H, m), 1.18-1.40 (12H, m) ppm.

$^{19}$F-NMR (565 MHz in DMSO-d6): δ=−131.0 (4F, d) ppm.

Example 1-18: Synthesis of Phenol 18

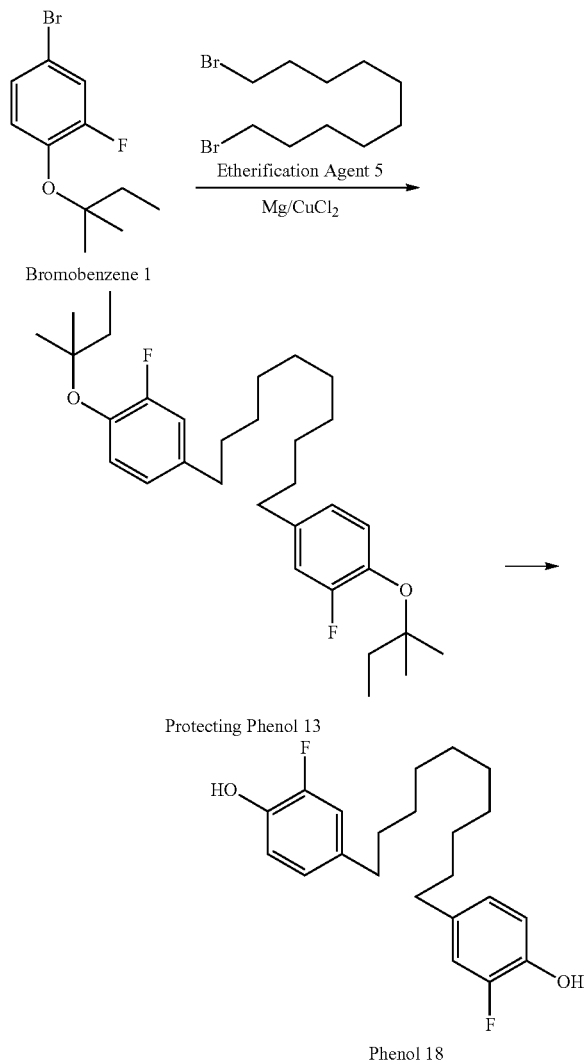

Example 1-18-1: Synthesis of Protecting Phenol 13

In an atmosphere of nitrogen, a Grignard reagent prepared in advance by using bromobenzene 1 (67.9 g), magnesium (6.6 g), and 260 mL of tetrahydrofuran was added dropwise to a slurry solution of etherification agent 5 (30.0 g), cupric chloride (0.80 g) and tetrahydrofuran (150 mL) at an internal temperature of 40° C. to 60° C. The stirring was continued at the same reaction temperature for 20 hours. Thereafter, at an internal temperature of 30° C. or less, a saturated aqueous ammonium chloride solution (18.0 g) was added to stop the reaction. A typical work-up method was performed to obtain protecting phenol 13 (72.7 g, yield=72%).

Example 1-18-2: Synthesis of Phenol 18

Phenol 18 was obtained in the same manner as in Example 1-1-4, except that protecting phenol 13 was used instead of protecting phenol 1 (yield=77%).

IR (D-ATR): ν=3406, 2923, 2852, 1628, 1602, 1516, 1470, 1460, 1448, 1355, 1326, 1284, 1245, 1227, 1200, 1143, 1117, 1101, 1052, 937, 864, 825, 790, 744 cm$^{-1}$.

$^1$H-NMR (600 MHz in DMSO-d6): δ=9.46 (2H, s), 6.91 (2H, dd), 6.81 (2H, t), 6.75 (2H, dd), 2.43 (4H, t), 1.48 (4H, m), 1.21 (12H, m) ppm.

$^{19}$F-NMR (565 MHz in DMSO-d6): δ=−136.8 (2F, t) ppm.

Example 1-19: Synthesis of Phenol 19

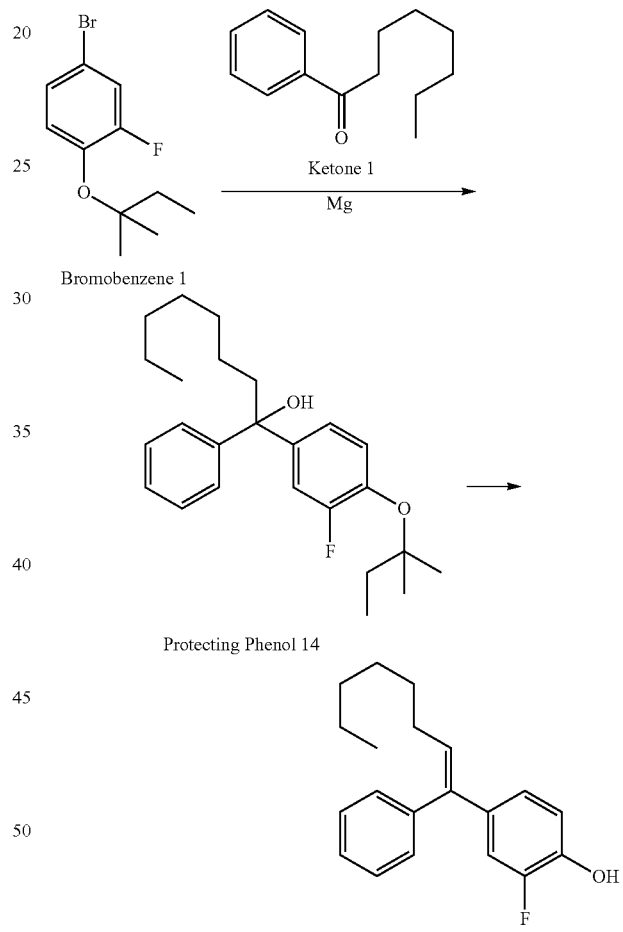

Example 1-19-1: Synthesis of Protecting Phenol 14

In an atmosphere of nitrogen, a solution of ketone 1 (10.2 g) and tetrahydrofuran (50 mL) was added dropwise to a Grignard reagent prepared in advance by using bromobenzene 1 (17.0 g), magnesium (1.7 g), and 40 mL of tetrahydrofuran at an internal temperature of 30° C. or less. The stirring was continued at the same reaction temperature for 3 hours. Thereafter, at an internal temperature of 30° C. or less, a saturated aqueous ammonium chloride solution (40.0 g) was added to stop the reaction. A typical work-up method was performed to obtain protecting phenol 14 (22.4 g, yield=94%).

Example 1-19-2: Synthesis of Phenol 19

Phenol 19 was obtained in the same manner as in Example 1-1-4, except that protecting phenol 14 was used instead of protecting phenol 1 (yield=95%).

IR (D-ATR): ν=3415, 2956, 2924, 2854, 1620, 1594, 1514, 1494, 1443, 1429, 1361, 1280, 1220, 1177, 1102, 1073, 1029, 962, 874, 820, 780, 763, 701 cm$^{-1}$.

$^1$H-NMR (600 MHz in DMSO-d6): δ=9.84 (1H, s), 7.38 (1H, t), 7.18~7.34 (2H, m), 7.12 (2H, dd), 6.79~6.98 (2H, m), 6.73 (1H, t), 6.11 (1H, t), 2.04 (1H, q), 1.95 (1H, q), 1.31~1.41 (2H, m), 1.11~1.28 (6H, m), 0.80 (3H, t) ppm.

$^{19}$F-NMR (565 MHz in DMSO-d6): δ=−136.7-136.6 (1F, m) ppm.

Example 1-20: Synthesis of Phenol 20

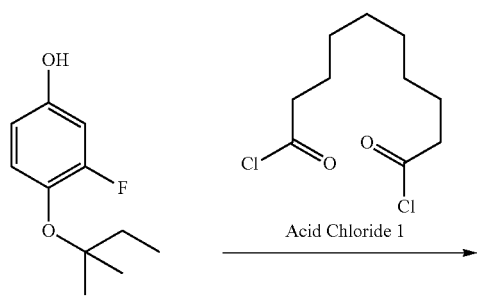

Intermediate Phenol 1

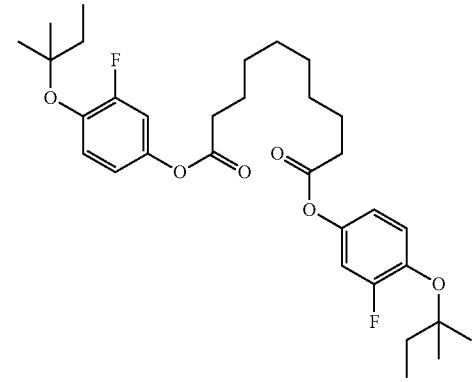

Protecting Phenol 15

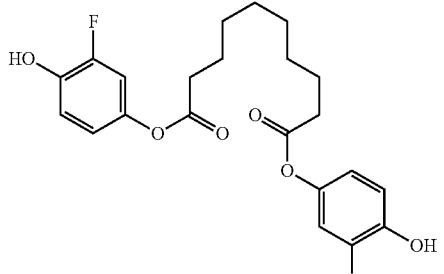

Phenol 20

Example 1-20-1: Synthesis of Protecting Phenol 15

In an atmosphere of nitrogen, a solution of acid chloride 1 (5.8 g) and acetonitrile (10 g) was added dropwise to a solution of intermediate phenol 1 (10.0 g), triethylamine (6.5 g) and acetonitrile (30 g) at an internal temperature of 20° C. to 40° C. The stirring was continued at the same reaction temperature for 3 hours. Thereafter, at an internal temperature of 30° C. or less, water (40 g) was added to stop the reaction. A typical work-up method was performed to obtain protecting phenol 15 (14.2 g, yield=96%).

Example 1-20-2: Synthesis of Phenol 20

Phenol 20 was obtained in the same manner as in Example 1-1-4, except that protecting phenol 15 was used instead of protecting phenol 1 (yield=87%).

IR (D-ATR): ν=3390, 3075, 2934, 2857, 1743, 1609, 1518, 1467, 1448, 1408, 1381, 1363, 1297, 1265, 1214, 1190, 1149, 1105, 964, 923, 863, 822, 795 cm$^{-1}$.

$^1$H-NMR (600 MHz in DMSO-d6): δ=9.81 (1H, s), 6.96 (2H, dt), 6.91 (2H, t), 6.72 (2H, m), 2.47 (4H, t), 1.58 (4H, m), 1.27 (8H, m) ppm.

$^{19}$F-NMR (565 MHz in DMSO-d6): δ=−134.0 (1F, t) ppm.

Example 1-21: Synthesis of Phenol 21 PP-72

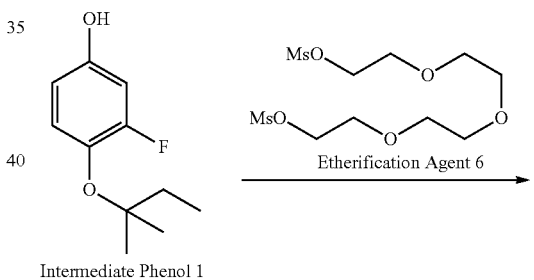

Intermediate Phenol 1

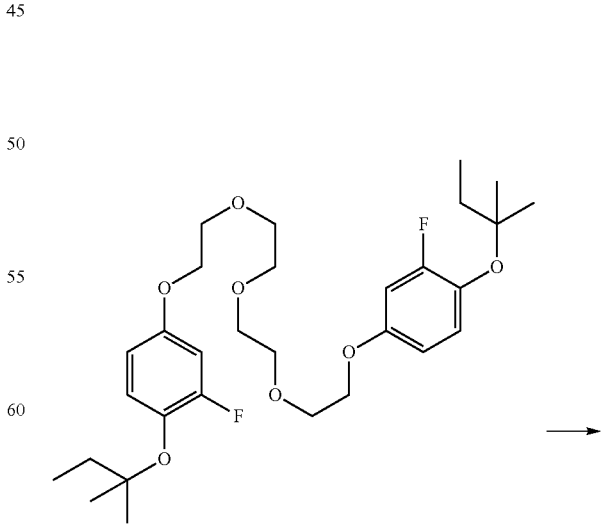

Protecting Phenol 16

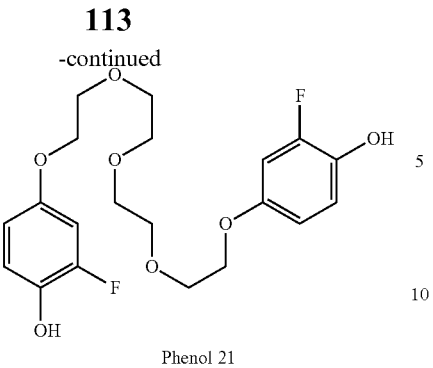

Phenol 21 wherein Ms represents a mesyl group.

Example 1-21-1: Synthesis of Protecting Phenol 16

Protecting phenol 16 was obtained in the same manner as in Example 1-1-3, except that etherification agent 6 was used instead of etherification agent 1 (yield=85%).

Example 1-21-2: Synthesis of Phenol 21

Phenol 21 was obtained in the same manner as in Example 1-1-4, except that protecting phenol 16 was used instead of protecting phenol 1 (yield=81%).

$^1$H-NMR (600 MHz in DMSO-d6): δ=9.22 (2H, s), 6.83 (2H, dd), 6.78 (2H, dd), 6.57 (2H, ddd), 3.95~3.98 (4H, m), 3.65~3.70 (4H, m), 3.50~3.56 (8H, m) ppm.

$^{19}$F-NMR (565 MHz in DMSO-d6): δ=−136.8 (2F, t) ppm.

Example 1-22: Synthesis of Phenol 22

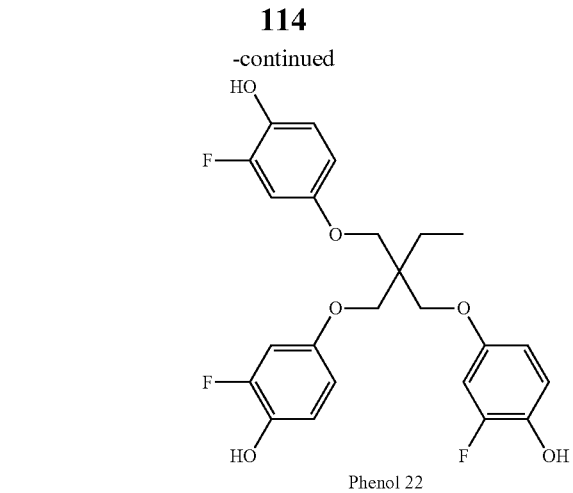

Phenol 22 wherein Ms represents a mesyl group.

Example 1-22-1: Synthesis of Protecting Phenol 17

Protecting phenol 17 was obtained in the same manner as in Example 1-1-3, except that etherification agent 7 was used instead of etherification agent 1 (yield=67%).

Example 1-22-2: Synthesis of Phenol 22

Phenol 22 was obtained in the same manner as in Example 1-1-4, except that protecting phenol 17 was used instead of protecting phenol 1 (yield=90%).

Example 1-23: Synthesis of Phenol 23

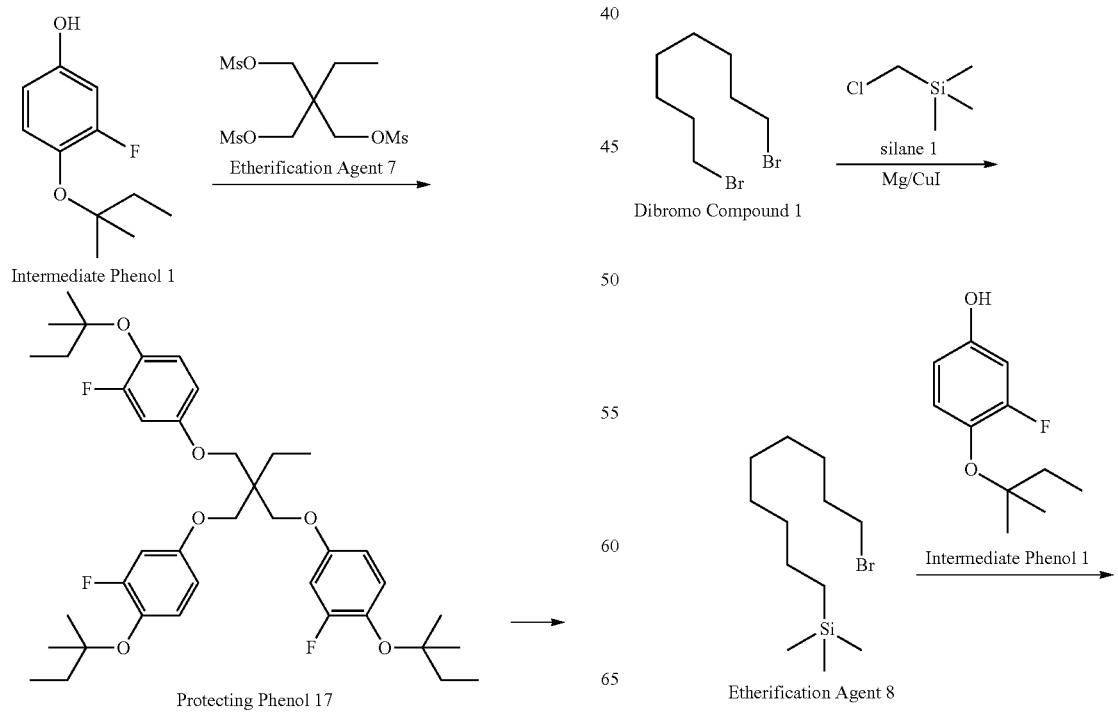

115

-continued

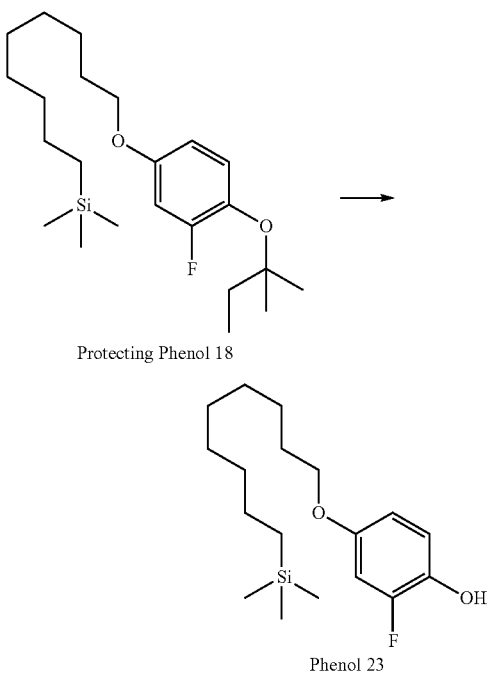

Protecting Phenol 18

Phenol 23

Example 1-23-1: Synthesis of Etherification Agent 8

In an atmosphere of nitrogen, a Grignard reagent prepared in advance by using silane 1 (30.7 g), magnesium (6.7 g), and 120 mL of tetrahydrofuran was added dropwise to a solution of dibromo compound 1 (75.0 g), cuprous iodide (0.52 g), triethyl phosphite (0.96 g), and tetrahydrofuran (100 mL) at an internal temperature of 10° C. to 30° C. The stirring was continued at the same reaction temperature for 20 hours. Thereafter, at an internal temperature of 30° C. or less, a saturated aqueous ammonium chloride solution (200 g) was added to stop the reaction. A typical work-up method was performed to obtain etherification agent 8 (43.3 g, yield=62%).

Boiling point: 72° C./20 Pa

Example 1-23-2: Synthesis of Protecting Phenol 18

Protecting phenol 18 was obtained in the same manner as in Example 1-1-3, except that etherification agent 8 was used instead of etherification agent 1 (yield=85%).

Example 1-23-3: Synthesis of Phenol 23

Phenol 23 was obtained in the same manner as in Example 1-1-4, except that protecting phenol 18 was used instead of protecting phenol 1 (yield=93%).

$^1$H-NMR (500 MHz in DMSO-d6): δ=9.18 (1H, s), 6.81 (1H, t), 6.72 (1H, dd), 6.53 (1H, dd), 3.82 (2H, t), 1.63 (2H, m), 1.19-1.40 (12H, m), 0.44 (2H, m), −0.06 (9H, s) ppm.

$^{19}$F-NMR (470 MHz in DMSO-d6): δ=−133.7 (1F, t) ppm.

Example 1-24: Synthesis of Phenol 24

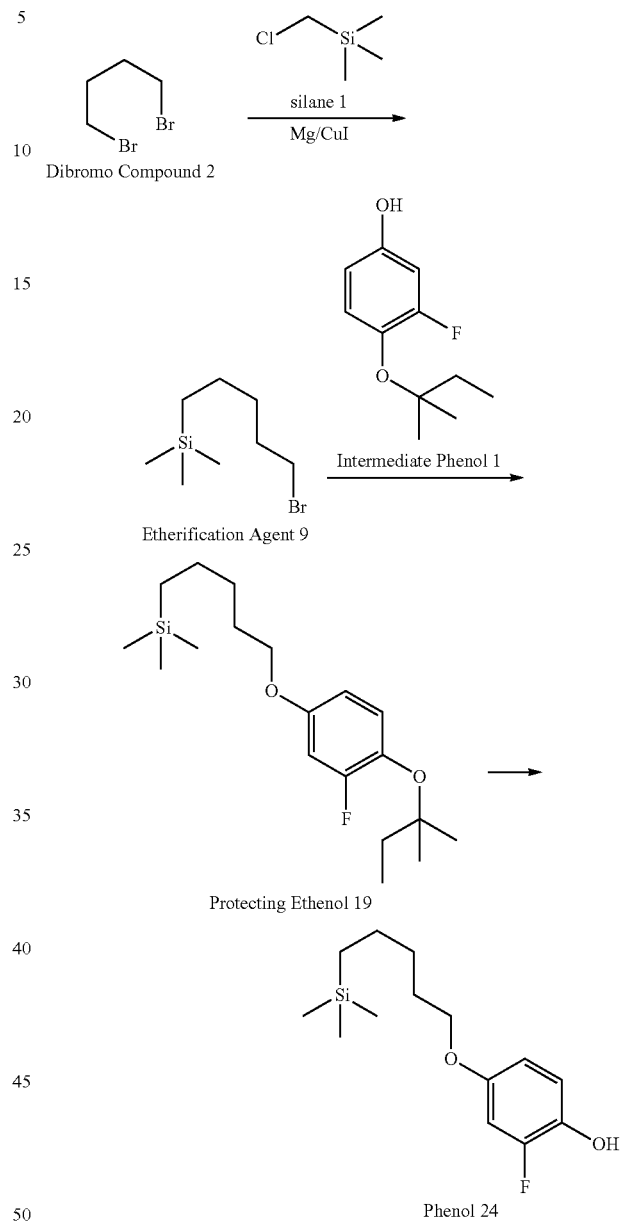

Example 1-24-1: Synthesis of Etherification Agent 9

Etherification agent 9 was obtained in the same manner as in Example 1-23-1, except that dibromo compound 2 was used instead of dibromo compound 1 (yield=66%).

Example 1-24-2: Synthesis of Protecting Phenol 19

Protecting phenol 19 was obtained in the same manner as in Example 1-1-3, except that etherification agent 9 was used instead of etherification agent 1 (yield=86%).

Example 1-24-3: Synthesis of Phenol 24

Phenol 24 was obtained in the same manner as in Example 1-1-4, except that protecting phenol 19 was used instead of protecting phenol 1 (yield=91%).

Example 1-25: Synthesis of Phenol 25

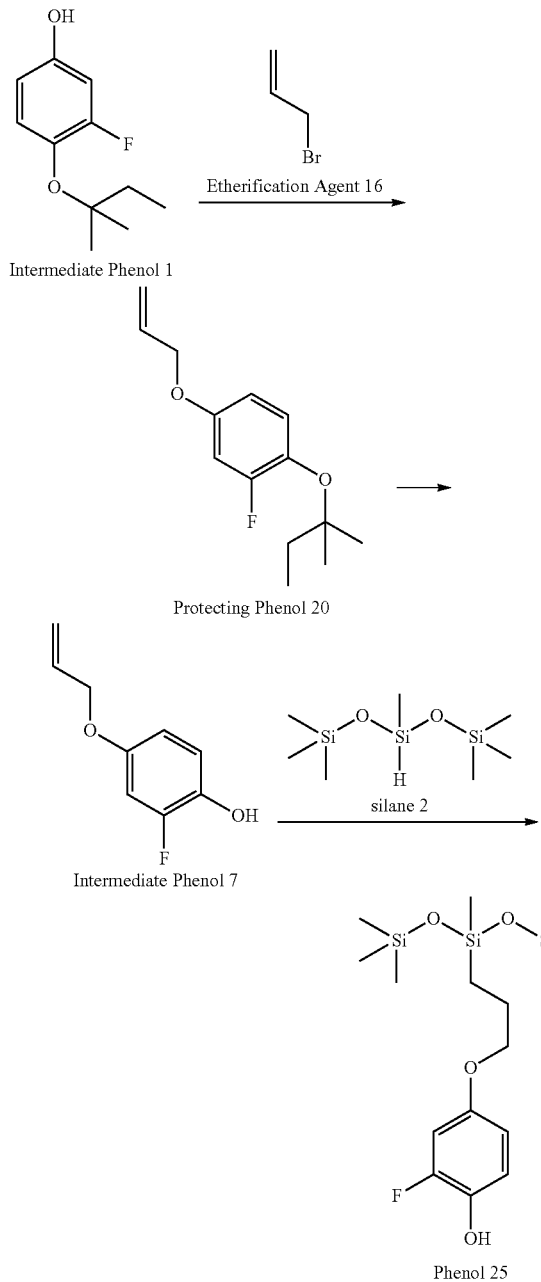

Example 1-25-1: Synthesis of Protecting Phenol 20

Protecting phenol 20 was obtained in the same manner as in Example 1-1-3, except that etherification agent 10 was used instead of etherification agent 1 (yield=84%).

Example 1-25-2: Synthesis of Intermediate Phenol 7

Intermediate phenol 7 was obtained in the same manner as in Example 1-1-4, except that protecting phenol 20 was used instead of protecting phenol 1 (yield=89%).

Example 1-25-3: Synthesis of Phenol 25

In an atmosphere of nitrogen, a solution of silane 2 (21.8 g) and toluene (20 g) was added dropwise to a solution of intermediate phenol 7 (16.5 g), CAT-PL-50N (0.2 mg) and toluene (60 g) at an internal temperature of 30° C. to 60° C. The stirring was continued at the same reaction temperature for 3 hours. Activated carbon (2 g) and silica gel (2 g) were added to the reaction solution, followed by stirring for 0.5 hour and subsequent filtration to separate the activated carbon and silica gel. After concentration of the filtrate, distillation was performed under reduced pressure to obtain phenol 25 (21.4 g, yield=56%).

Boiling point: 107° C./15 Pa

Example 1-26: Synthesis of Phenol 26

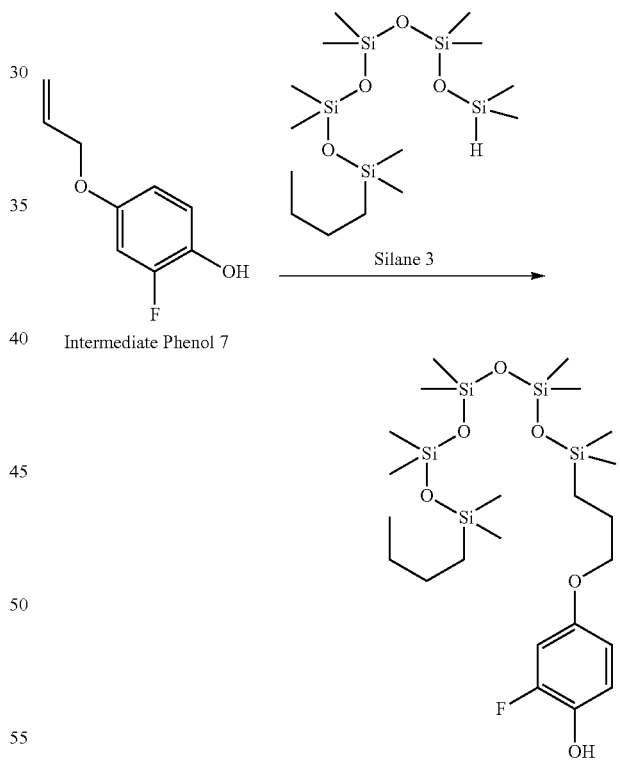

Example 1-26-1: Synthesis of Phenol 26

Phenol 26 was obtained in the same manner as in Example 1-25-3, except that silane 3 was used instead of silane 2 (yield=52%).

Phenols 1 to 26 synthesized in Examples 1-1 to 1-26 are shown below.

Phenol 1
Phenol 2
Phenol 3
Phenol 4
Phenol 5
Phenol 6
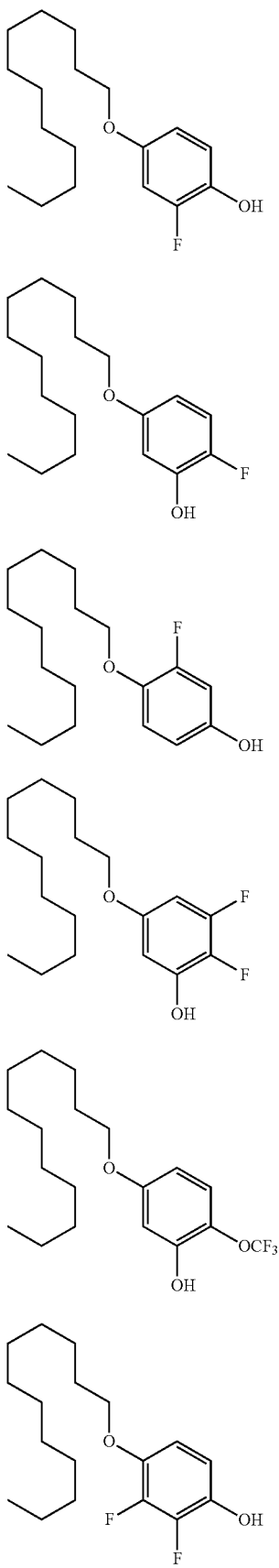
Phenol 7
Phenol 8
Phenol 9
Phenol 10
Phenol 11
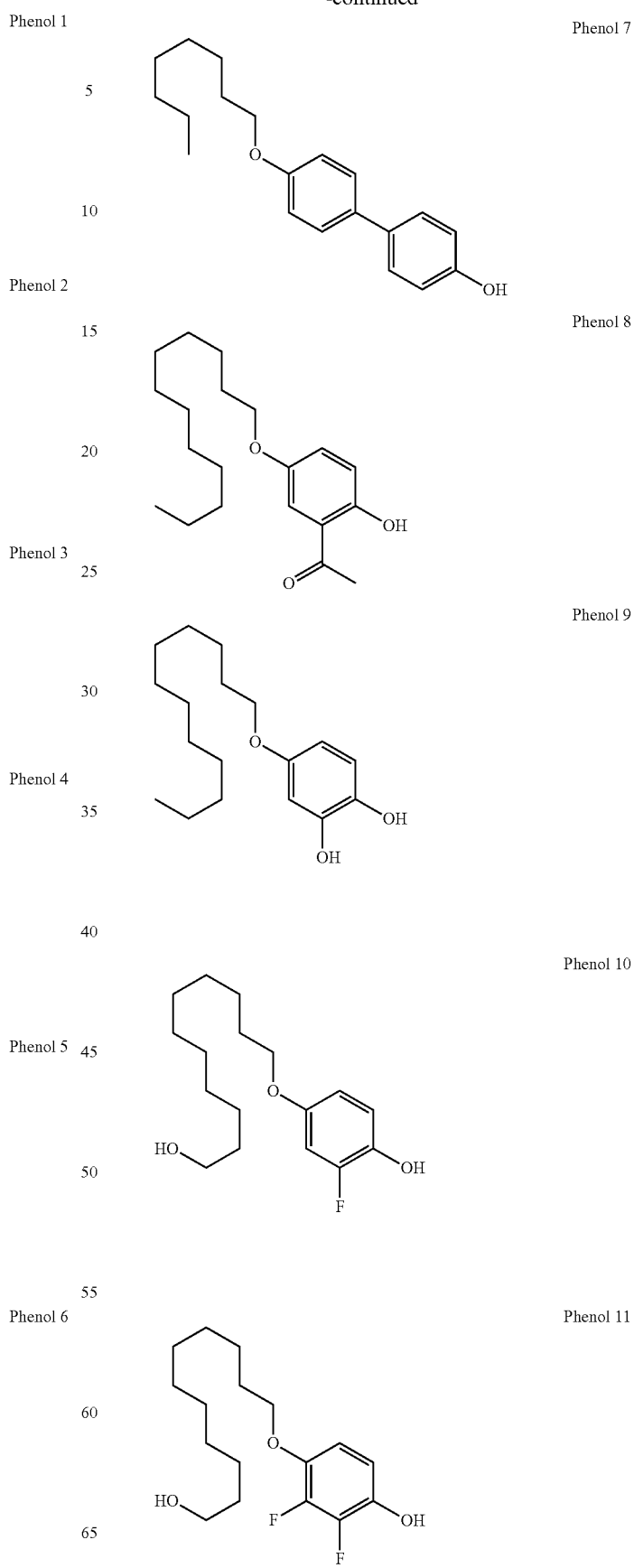

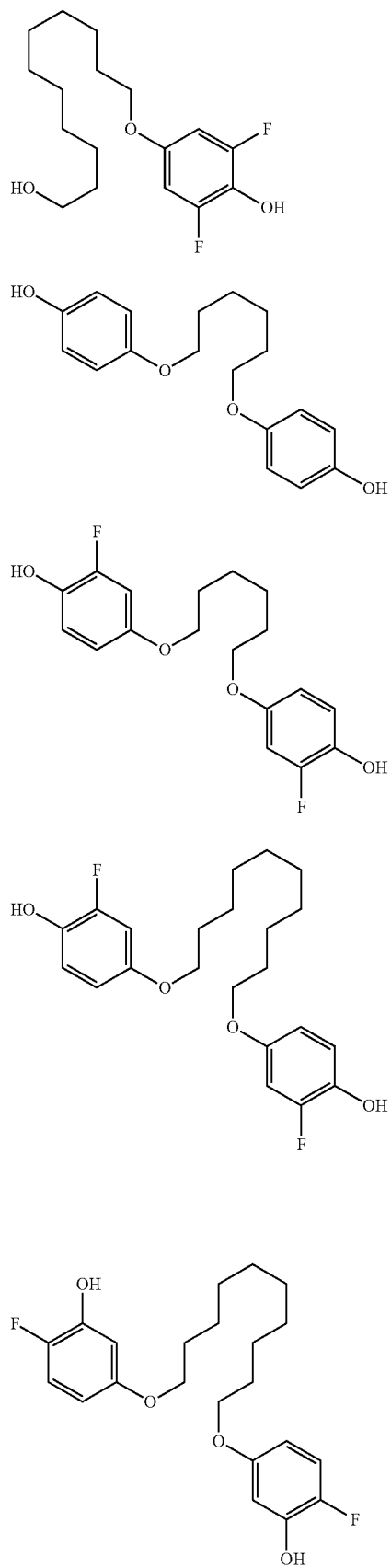

Phenol 22

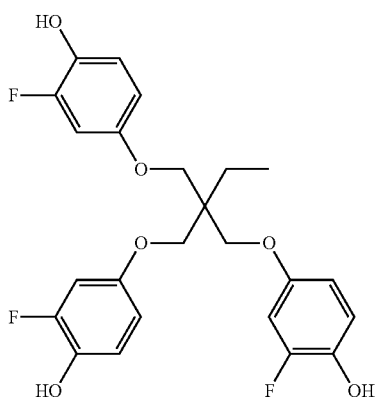

Phenol 23

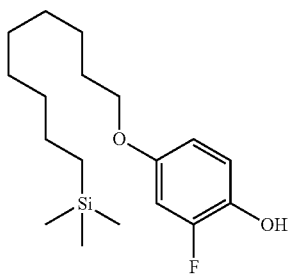

Phenol 24

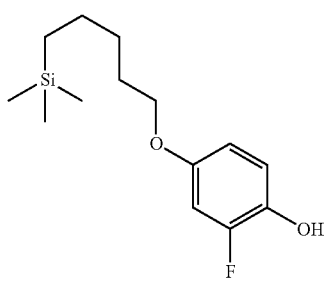

Phenol 25

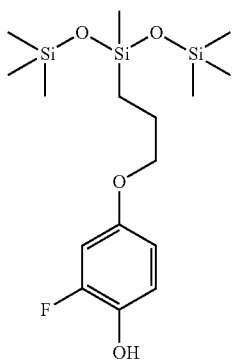

Phenol 26

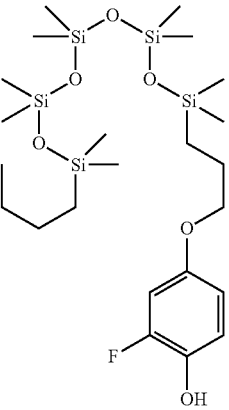

Synthesis Examples

The polyurethane to be used for the conductive paste composition of the present invention was synthesized by the following method.

Raw Materials

High-Molecular-Weight Polyols

NIPPOLAN 4010 (manufactured by Tosoh Corporation): polyester polyol, number average molecular weight: 2000

NIPPOLAN 4009 (manufactured by Tosoh Corporation): polyester polyol, number average molecular weight: 1000

KURARAY POLYOL P-2010 (manufactured by KURARAY CO., LTD.): polyester polyol, number average molecular weight: 2000

KURARAY POLYOL C-2090 (manufactured by KURARAY CO., LTD.): polycarbonate polyol, number average molecular weight: 2000

PLACCEL 210 (manufactured by DAICEL CORPORATION): polycaprolactone diol, number average molecular weight: 1000

Chain Extender (6)

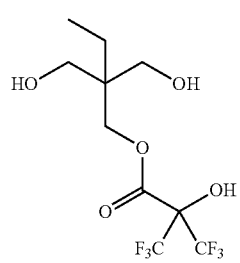

(7)

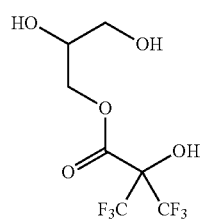

(8)

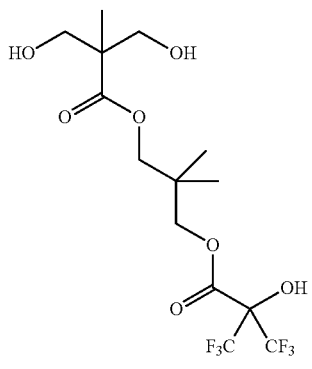

(9)

(10)

(11)

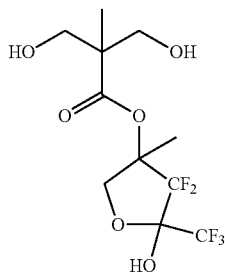

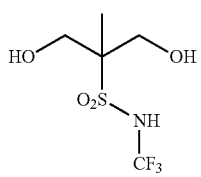

(12)

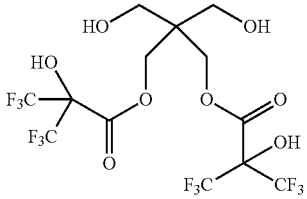

(13)

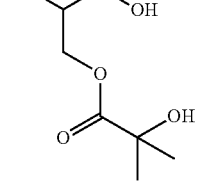

(14)

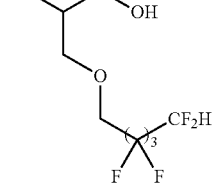

(15)

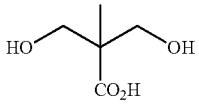

Polyisocyanate

TDI: 2,4-tolylene diisocyanate or 2,6-tolylene diisocyanate and isomer mixtures thereof IPDI: isophorone diisocyanate Catalyst XK-640 (manufactured by KING INDUSTRIES, Inc.)

Synthesis Example 1: Synthesis of PU1

Under a nitrogen stream, 47.7 g of TDI and 0.05 g of XK-640 (manufactured by KING INDUSTRIES, Inc.) were measured and placed in a reaction container of a planetary mixer and heated to 60° C. Then, 114.9 g of a 80 mass % solution of NIPPOLAN 4009 in diethylene glycol monobutyl ether acetate (hereinafter referred to as BCA) was added and the mixture was stirred for 30 minutes to prepare a prepolymer. The prepolymer solution was diluted with 50.7 g of BCA, and subsequently heated to 90° C., followed by dropwise addition of 120.7 g of a 50 mass % solution of chain extender (6) in BCA. While the reaction temperature was kept at 90° C., the mixture was aged for 9 hours to obtain a solution of PU1 in BCA.

PU1: Mw=119,220, Mw/Mn=4.22

PU2 to PU14 were synthesized (Synthesis Examples 2 to 14) by the same procedure as in Synthesis Example 1 above, except that the kinds and proportions of polyisocyanate, high-molecular-weight polyol, and chain extender, as well as the amount of catalyst used were changed to those shown in Table 1.

TABLE 1

| | High-Molecular-Weight Polyols [part by mass] | Polyisocyanate [part by mass] | Chain Extender [part by mass] | Catalyst [part by mass] | Mw | Mw/Mn |
|---|---|---|---|---|---|---|
| PU1 | NIPPOLAN 4009 [46] | TDI [24] | (6) [30] | XK-640 [0.05] | 119,220 | 4.22 |
| PU2 | NIPPOLAN 4009 [43] | IPDI [30] | (7) [27] | XK-640 [2.00] | 63,690 | 4.93 |
| PU3 | NIPPOLAN 4009 [43] | TDI [22] | (8) [35] | XK-640 [0.05] | 87,650 | 4.15 |
| PU4 | NIPPOLAN 4009 [45] | TDI [23] | (9) [32] | XK-640 [0.05] | 45,320 | 4.54 |
| PU5 | NIPPOLAN 4009 [45] | TDI [24] | (10) [31] | XK-640 [0.05] | 79,680 | 4.11 |
| PU6 | NIPPOLAN 4009 [50] | TDI [26] | (11) [24] | XK-640 [0.05] | 35,660 | 4.89 |
| PU7 | NIPPOLAN 4009 [39] | TDI [20] | (12) [41] | XK-640 [0.05] | 58,980 | 5.12 |
| PU8 | NIPPOLAN 4010 [48] | IPDI [25] | (7) [27] | XK-640 [12.00] | 25,000 | 3.22 |
| PU9 | P-2010 [46] | IPDI [27] | (7) [27] | XK-640 [2.00] | 71,840 | 5.47 |
| PU10 | C-2090 [47] | IPDI [25] | (7) [28] | XK-640 [2.00] | 21,660 | 2.63 |
| PU11 | PLACCEL 210 [45] | IPDI [29] | (7) [26] | XK-640 [1.00] | 20,000 | 2.11 |
| PU12 | NIPPOLAN 4009 [50] | IPDI [32] | (13) [18] | XK-640 [0.05] | 30,800 | 5.46 |
| PU13 | NIPPOLAN 4010 [46] | IPDI [27] | (14) [27] | XK-640 [0.05] | 18,410 | 2.05 |
| PU14 | NIPPOLAN 4009 [53] | IPDI [33] | (15) [14] | XK-640 [0.05] | 30,890 | 2.42 |

Examples 2-1 to 2-49 and Comparative Examples 1-1 to 1-13

Preparation of Conductive Paste Compositions

As polymers for preparing conductive paste compositions, PU1 to PU14 shown in Table 1 and the following resins were used.

Fluorine rubber (G801, manufactured by Daikin Industries, Ltd.)

Polyester (UE-9200, manufactured by Unitika Ltd.)

Acrylic rubber (Nipol (registered trademark) 1042, manufactured by Zeon Corporation)

Phenols 1 to 26 described in Example 1 above were used as the phenol compounds as the additives, and the following comparative additives 1 to 4 were used as additives for Comparative Examples.

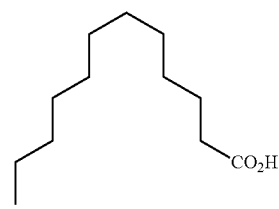

Comparative Additive 1

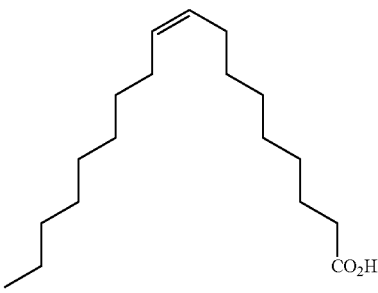

Comparative Additive 2

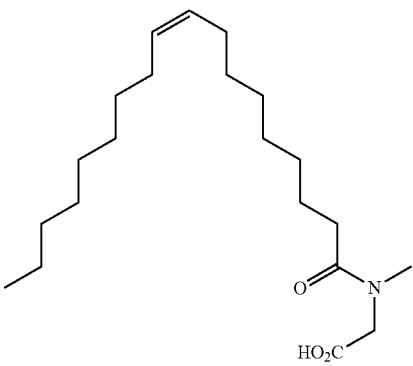

Comparative Additive 3

-continued

Comparative Additive 4

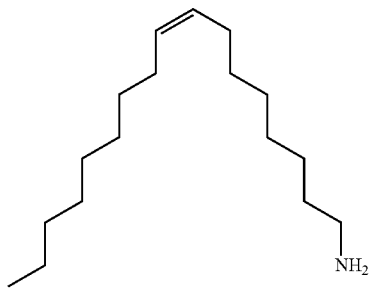

As conductive fillers, the following silver powders A to E and copper powders A and B were prepared.

Silver powder A: average particle diameter ($D_{L50}$): 2.1 μm
Silver powder B: average particle diameter ($D_{L50}$): 5.3 μm
Silver powder C: average particle diameter ($D_{L50}$): 1.2 μm
Silver powder D: average particle diameter ($D_{L50}$): 0.67 μm
Silver powder E: average particle diameter ($D_{L50}$): 1.72 μm
Copper powder A: average particle diameter ($D_{L50}$): 5.5 μm
Copper powder B: average particle diameter ($D_{L50}$): 1.3 μm In the average particle diameter measurement, a laser-diffraction particle size distribution measurement apparatus was used to measure the particle size distribution, and the cumulative value 50% of the particle diameters was determined as an average particle diameter.

According to the formulations shown in Tables 2, 3, a polymer, a conductive filler, a solvent (diethylene glycol monobutyl ether acetate) and an additive were mixed by stirring to prepare a conductive paste composition (CI-1 to CI-62).

TABLE 2

| | Conductive Paste Composition | Polymer [part by mass] | Conductive Filler [part by mass] | Solvent [part by mass] | Additive [part by mass] |
|---|---|---|---|---|---|
| Example 2-1 | CI-1 | PU1 [12] | Silver Powder E [68] | BCA [20] | Phenol 1 [4] |
| Example 2-2 | CI-2 | PU1 [12] | Silver Powder E [68] | BCA [20] | Phenol 2 [4] |
| Example 2-3 | CI-3 | PU1 [12] | Silver Powder E [68] | BCA [20] | Phenol 3 [4] |
| Example 2-4 | CI-4 | PU1 [12] | Silver Powder E [68] | BCA [20] | Phenol 4 [4] |
| Example 2-5 | CI-5 | PU1 [12] | Silver Powder E [68] | BCA [20] | Phenol 5 [4] |
| Example 2-6 | CI-6 | PU1 [12] | Silver Powder E [68] | BCA [20] | Phenol 6 [4] |
| Example 2-7 | CI-7 | PU1 [12] | Silver Powder E [68] | BCA [20] | Phenol 7 [4] |
| Example 2-8 | CI-8 | PU1 [12] | Silver Powder E [68] | BCA [20] | Phenol 8 [4] |
| Example 2-9 | CI-9 | PU1 [12] | Silver Powder E [68] | BCA [20] | Phenol 9 [4] |
| Example 2-10 | CI-10 | PU1 [12] | Silver Powder E [68] | BCA [20] | Phenol 10 [4] |
| Example 2-11 | CI-11 | PU1 [12] | Silver Powder E [68] | BCA [20] | Phenol 11 [4] |
| Example 2-12 | CI-12 | PU1 [12] | Silver Powder E [68] | BCA [20] | Phenol 12 [4] |
| Example 2-13 | CI-13 | PU1 [12] | Silver Powder E [68] | BCA [20] | Phenol 13 [4] |
| Example 2-14 | CI-14 | PU1 [12] | Silver Powder E [68] | BCA [20] | Phenol 14 [4] |
| Example 2-15 | CI-15 | PU1 [12] | Silver Powder E [68] | BCA [20] | Phenol 15 [4] |
| Example 2-16 | CI-16 | PU1 [12] | Silver Powder E [68] | BCA [20] | Phenol 16 [4] |
| Example 2-17 | CI-17 | PU1 [12] | Silver Powder E [68] | BCA [20] | Phenol 17 [4] |
| Example 2-18 | CI-18 | PU1 [12] | Silver Powder E [68] | BCA [20] | Phenol 18 [4] |
| Example 2-19 | CI-19 | PU1 [12] | Silver Powder E [68] | BCA [20] | Phenol 19 [4] |
| Example 2-20 | CI-20 | PU1 [12] | Silver Powder E [68] | BCA [20] | Phenol 20 [4] |
| Example 2-21 | CI-21 | PU1 [12] | Silver Powder E [68] | BCA [20] | Phenol 21 [4] |
| Example 2-22 | CI-22 | PU1 [12] | Silver Powder E [68] | BCA [20] | Phenol 22 [4] |
| Example 2-23 | CI-23 | PU1 [12] | Silver Powder E [68] | BCA [20] | Phenol 23 [4] |
| Example 2-24 | CI-24 | PU1 [12] | Silver Powder E [68] | BCA [20] | Phenol 24 [4] |
| Example 2-25 | CI-25 | PU1 [12] | Silver Powder E [68] | BCA [20] | Phenol 25 [4] |

TABLE 2-continued

| | Conductive Paste Composition | Polymer [part by mass] | Conductive Filler [part by mass] | Solvent [part by mass] | Additive [part by mass] |
|---|---|---|---|---|---|
| Example 2-26 | CI-26 | PU1 [12] | Silver Powder E [68] | BCA [20] | Phenol 26 [4] |
| Example 2-27 | CI-27 | PU1 [12] | Silver Powder C [68] | BCA [20] | Phenol 1 [4] |
| Example 2-28 | CI-28 | PU2 [12] | Silver Powder C [68] | BCA [20] | Phenol 1 [4] |
| Example 2-29 | CI-29 | PU3 [12] | Silver Powder C [68] | BCA [20] | Phenol 1 [4] |
| Example 2-30 | CI-30 | PU4 [12] | Silver Powder C [68] | BCA [20] | Phenol 1 [4] |
| Example 2-31 | CI-31 | PU5 [12] | Silver Powder C [68] | BCA [20] | Phenol 1 [4] |
| Example 2-32 | CI-32 | PU6 [12] | Silver Powder C [68] | BCA [20] | Phenol 1 [4] |
| Example 2-33 | CI-33 | PU7 [12] | Silver Powder C [68] | BCA [20] | Phenol 1 [4] |
| Example 2-34 | CI-34 | PU8 [12] | Silver Powder C [68] | BCA [20] | Phenol 1 [4] |
| Example 2-35 | CI-35 | PU9 [12] | Silver Powder C [68] | BCA [20] | Phenol 1 [4] |

BCA: diethylene glycol monobutyl ether acetate

TABLE 3

| | Conductive Paste Composition | Polymer [part by mass] | Conductive Filler [part by mass] | Solvent [part by mass] | Additive [part by mass] |
|---|---|---|---|---|---|
| Example 2-36 | CI-36 | PU10 [12] | Silver Powder C [68] | BCA [20] | Phenol 1 [4] |
| Example 2-37 | CI-37 | PU11 [12] | Silver Powder C [68] | BCA [20] | Phenol 1 [4] |
| Example 2-38 | CI-38 | PU12 [12] | Silver Powder C [68] | BCA [20] | Phenol 1 [4] |
| Example 2-39 | CI-39 | PU13 [12] | Silver Powder C [68] | BCA [20] | Phenol 1 [4] |
| Example 2-40 | CI-40 | PU14 [12] | Silver Powder C [68] | BCA [20] | Phenol 1 [4] |
| Example 2-41 | CI-41 | Fluorine rubber [12] | Silver Powder C [68] | BCA [20] | Phenol 1 [4] |
| Example 2-42 | CI-42 | Polyester [12] | Silver Powder C [68] | BCA [20] | Phenol 1 [4] |
| Example 2-43 | CI-43 | Acrylic rubber [12] | Silver Powder C [68] | BCA [20] | Phenol 1 [4] |
| Example 2-44 | CI-44 | PU1 [12] | Silver Powder A [68] | BCA [20] | Phenol 15 [4] |
| Example 2-45 | CI-45 | PU1 [12] | Silver Powder B [68] | BCA [20] | Phenol 15 [4] |
| Example 2-46 | CI-46 | PU1 [12] | Silver Powder C [68] | BCA [20] | Phenol 15 [4] |
| Example 2-47 | CI-47 | PU1 [12] | Silver Powder D [68] | BCA [20] | Phenol 15 [4] |
| Example 2-48 | CI-48 | PU1 [12] | Copper Powder A [68] | BCA [20] | Phenol 15 [4] |
| Example 2-49 | CI-49 | PU1 [12] | Copper Powder B [68] | BCA [20] | Phenol 15 [4] |
| Comparative Example 1-1 | CI-50 | PU1 [12] | Silver Powder C [68] | BCA [20] | — |
| Comparative Example 1-2- | CI-51 | PU2 [12] | Silver Powder C [68] | BCA [20] | — |
| Comparative Example 1-3 | CI-52 | PU3 [12] | Silver Powder C [68] | BCA [20] | — |
| Comparative Example 1-4 | CI-53 | PU12 [12] | Silver Powder C [68] | BCA [20] | — |
| Comparative Example 1-5 | CI-54 | PU13 [12] | Silver Powder C [68] | BCA [20] | — |
| Comparative Example 1-6 | CI-55 | Fluorine rubber [12] | Silver Powder C [68] | BCA [20] | — |
| Comparative Example 1-7 | CI-56 | Polyester [12] | Silver Powder E [68] | BCA [20] | — |

TABLE 3-continued

| Conductive Paste Composition | Polymer [part by mass] | Conductive Filler [part by mass] | Solvent [part by mass] | Additive [part by mass] |
|---|---|---|---|---|
| Comparative Example 1-8 | CI-57 | PU1 [12] | Silver Powder C [68] | BCA [20] | Comparative Additive 1 [4] |
| Comparative Example 1-9 | CI-58 | PU1 [12] | Silver Powder C [68] | BCA [20] | Comparative Additive 2 [4] |
| Comparative Example 1-10 | CI-59 | PU1 [12] | Silver Powder C [68] | BCA [20] | Comparative Additive 3 [4] |
| Comparative Example 1-11 | CI-60 | PU1 [12] | Silver Powder C [68] | BCA [20] | Comparative Additive 4 [4] |
| Comparative Example 1-12 | CI-61 | PU1 [12] | Copper Powder A [68] | BCA [20] | — |
| Comparative Example 1-13 | CI-62 | PU1 [12] | Copper Powder B [68] | BCA [20] | — |

BCA: diethylene glycol monobutyl ether acetate

Examples 3-1 to 3-50 and Comparative Examples 2-1 to 2-13

Evaluation of Stretchable Conductive Wire

Preparation of Evaluation Samples

A conductive paste composition was applied onto a polyurethane film by using a screen printer MT-320TVC manufactured by Micro-tec Co., Ltd., followed by heating with a hot-air dryer to form a conductive wire with a line width of 3 mm, a length of 100 mm, and a thickness of 15 μm.

Measurement of Initial Electric Resistance in Non-Elongated State

The electric resistance between two ends of the stretchable conductive wire formed on the polyurethane film was measured by 4-terminal resistance measurement method. The electric resistance was measured with PXIe-4136SMU resistance measurement unit manufactured by National Instruments Corp.

Electric resistance (Ω) R=V/I (V: voltage, I: current)
Tables 4 and 5 show the measurement results of the initial electric resistance.

Measurement of Maximum Electric Resistance upon 20% Elongation

The polyurethane film with the stretchable conductive wire formed thereon was elongated by 20% from the non-elongated state (0%) in which the polyurethane film was not loose. The polyurethane film in this state was immobilized to measure the electric resistance by 4-terminal resistance measurement method.

The polyurethane film with the stretchable conductive wire formed thereon was elongated at a speed of 100 mm/min in a longitudinal direction of the stretchable conductive wire (rectangle) by using a precision universal testing machine AG-Xplus HS manufactured by Shimadzu Corporation.

Change in electric resistance upon 20% elongation=
[electric resistance (Ω) upon 20% elongation]÷
[initial electric resistance (Ω)]×100

Tables 4 and 5 show the change in electric resistance upon 20% elongation.

Measurement of Maximum Electric Resistance upon 300% Elongation

The polyurethane film with the stretchable conductive wire formed thereon was elongated by 300% from the non-elongated state (0%), and was immobilized to measure the electric resistance.

The polyurethane film with the stretchable conductive wire formed thereon was elongated at a speed of 100 mm/min in a longitudinal direction of the stretchable conductive wire (rectangle) by using a precision universal testing machine AG-Xplus HS manufactured by Shimadzu Corporation.

Change in electric resistance upon 300% elongation=
[electric resistance (Ω) upon 300% elongation]÷
[initial electric resistance (Ω)]×100

Tables 4 and 5 show the change in electric resistance upon 300% elongation.

Measurement of Maximum Electric Resistance Value in Repetitive Elongations and Shrinkages at 0 to 20%

The polyurethane film with the stretchable conductive wire formed thereon was reciprocately elongated and shrunk 1000 times between the non-elongated state (0%) in which the polyurethane film was not loose and 20%-elongated state, and the change in electric resistance of the conductive wire over time was measured.

In this repetitive stretching test, the polyurethane film was elongated and shrunk at a tensile speed of 100 mm/min in the longitudinal direction of the stretchable conductive wire (rectangle) by using a precision universal testing machine AG-Xplus HS manufactured by Shimadzu Corporation.

Further, electrodes were set inside a sample immobilization jig of the tensile tester (the precision universal testing machine AG-Xplus HS described above), and the electric resistance was measured by the 4-terminal resistance measurement method using PXIe-4136SMU resistance measurement unit manufactured by National Instruments Corp.

Change in maximum electric resistance value by 1000-time repetitive elongations and shrinkages with an elongation ratio of 0 to 20%=[maximum electric resistance (Ω) in repetitive elongation and shrinkage test]÷[initial electric resistance (Ω)]×100

Tables 4 and 5 show the change in maximum electric resistance by 1000-time repetitive elongations and shrinkages with an elongation ratio of 20%.

TABLE 4

| | Conductive Paste Composition | Baking Temperature/Time | Initial Electric Resistance | Change in Electric Resistance (%) Upon 20% Elongation | Change in Electric Resistance (%) Upon 300% Elongation | Change in Maximum Electric Resistance (%) by 0-20% 1000-Time Repetitive Elongations and Shrinkages |
|---|---|---|---|---|---|---|
| Example 3-1 | CI-1 | 140° C./4 hr | 1.3 | 150 | 24500 | 1580 |
| Example 3-2 | CI-1 | 120° C./0.5 hr | 1.7 | 290 | 34820 | 2750 |
| Example 3-3 | CI-2 | 120° C./0.5 hr | 1.3 | 490 | 32360 | 2430 |
| Example 3-4 | CI-3 | 120° C./0.5 hr | 1.5 | 320 | 38380 | 1530 |
| Example 3-5 | CI-4 | 120° C./0.5 hr | 4.6 | 330 | — | 2820 |
| Example 3-6 | CI-5 | 120° C./0.5 hr | 1.5 | 330 | — | 2230 |
| Example 3-7 | CI-6 | 120° C./0.5 hr | 1.7 | 310 | — | 2200 |
| Example 3-8 | CI-7 | 120° C./0.5 hr | 3.4 | 280 | — | 2100 |
| Example 3-9 | CI-8 | 120° C./0.5 hr | 1.9 | 300 | — | 1760 |
| Example 3-10 | CI-9 | 120° C./0.5 hr | 1.4 | 320 | — | 1490 |
| Example 3-11 | CI-10 | 120° C./0.5 hr | 1.1 | 420 | — | 1730 |
| Example 3-12 | CI-11 | 120° C./0.5 hr | 1.1 | 340 | — | 2070 |
| Example 3-13 | CI-12 | 120° C./0.5 hr | 1.2 | 300 | — | 2000 |
| Example 3-14 | CI-13 | 120° C./0.5 hr | 4.0 | 275 | — | 1780 |
| Example 3-15 | CI-14 | 120° C./0.5 hr | 1.3 | 360 | — | 1070 |
| Example 3-16 | CI-15 | 120° C./0.5 hr | 1.6 | 290 | 28600 | 970 |
| Example 3-17 | CI-16 | 120° C./0.5 hr | 1.1 | 250 | 26500 | 1090 |
| Example 3-18 | CI-17 | 120° C./0.5 hr | 1.7 | 390 | — | 2300 |
| Example 3-19 | CI-18 | 120° C./0.5 hr | 1.2 | 380 | — | 3800 |
| Example 3-20 | CI-19 | 120° C./0.5 hr | 2.1 | 330 | — | 2850 |
| Example 3-21 | CI-20 | 120° C./0.5 hr | 1.4 | 346 | — | 1560 |
| Example 3-22 | CI-21 | 120° C./0.5 hr | 1.5 | 260 | — | 1100 |
| Example 3-23 | CI-22 | 120° C./0.5 hr | 1.7 | 178 | — | 1570 |
| Example 3-24 | CI-23 | 120° C./0.5 hr | 1.9 | 270 | — | 2700 |
| Example 3-25 | CI-24 | 120° C./0.5 hr | 1.8 | 280 | — | 2820 |
| Example 3-26 | CI-25 | 120° C./0.5 hr | 2.0 | 360 | — | 3500 |
| Example 3-27 | CI-26 | 120° C./0.5 hr | 2.1 | 390 | — | 3800 |
| Example 3-28 | CI-27 | 120° C./0.5 hr | 1.7 | 270 | — | 2000 |
| Example 3-29 | CI-28 | 120° C./0.5 hr | 1.2 | 150 | — | 2200 |
| Example 3-30 | CI-29 | 120° C./0.5 hr | 1.0 | 320 | — | 1700 |
| Example 3-31 | CI-30 | 120° C./0.5 hr | 2.6 | 260 | — | 1600 |
| Example 3-32 | CI-31 | 120° C./0.5 hr | 2.2 | 270 | — | 1800 |
| Example 3-33 | CI-32 | 120° C./0.5 hr | 2.4 | 290 | — | 2900 |
| Example 3-34 | CI-33 | 120° C./0.5 hr | 3.6 | 260 | — | 2200 |

—: Not measured

TABLE 5

| | Conductive Paste Composition | Baking Temperature/Time | Initial Electric Resistance | Change in Electric Resistance (%) Upon 20% Elongation | Change in Electric Resistance (%) Upon 300% Elongation | Change in Maximum Electric Resistance (%) by 0-20% 1000-Time Repetitive Elongations and Shrinkages |
|---|---|---|---|---|---|---|
| Example 3-35 | CI-34 | 120° C./0.5 hr | 2.2 | 260 | — | 1990 |
| Example 3-36 | CI-35 | 120° C./0.5 hr | 2.0 | 280 | — | 2850 |
| Example 3-37 | CI-36 | 120° C./0.5 hr | 2.2 | 260 | — | 1800 |
| Example 3-38 | CI-37 | 120° C./0.5 hr | 2.5 | 380 | — | 2400 |
| Example 3-39 | CI-38 | 120° C./0.5 hr | 3.1 | 360 | — | 2380 |
| Example 3-40 | CI-39 | 120° C./0.5 hr | 1.7 | 380 | — | 3333 |
| Example 3-41 | CI-40 | 120° C./0.5 hr | 2.3 | 330 | — | 2300 |
| Example 3-42 | CI-41 | 120° C./0.5 hr | 5.8 | 330 | — | 3800 |
| Example 3-43 | CI-42 | 120° C./0.5 hr | 5.8 | 330 | — | 3800 |
| Example 3-44 | CI-43 | 120° C./0.5 hr | 17.5 | 358 | — | 4770 |
| Example 3-45 | CI-44 | 120° C./0.5 hr | 0.9 | 370 | — | 3300 |
| Example 3-46 | CI-45 | 120° C./0.5 hr | 0.6 | 390 | — | 4000 |
| Example 3-47 | CI-46 | 120° C./0.5 hr | 1.8 | 230 | — | 2600 |
| Example 3-48 | CI-47 | 120° C./0.5 hr | 2.1 | 220 | — | 4300 |
| Example 3-49 | CI-48 | 140° C./4 hr | 4.5 | 460 | — | 4100 |
| Example 3-50 | CI-49 | 140° C./4 hr | 3.7 | 420 | — | 4300 |
| Comparative Example 2-1 | CI-50 | 120° C./0.5 hr | 1.3 | 460 | — | 5300 |
| Comparative Example 2-2 | CI-51 | 120° C./0.5 hr | 6.8 | 430 | — | 7600 |
| Comparative Example 2-3 | CI-52 | 120° C./0.5 hr | 4.5 | 600 | — | 6470 |
| Comparative Example 2-4 | CI-53 | 120° C./0.5 hr | 0.7 | 980 | Cutoff | Cutoff |
| Comparative Example 2-5 | CI-54 | 120° C./0.5 hr | 0.8 | 1010 | Cutoff | 42000 |

TABLE 5-continued

| | Conductive Paste Composition | Baking Temperature/Time | Initial Electric Resistance | Change in Electric Resistance (%) Upon 20% Elongation | Change in Electric Resistance (%) Upon 300% Elongation | Change in Maximum Electric Resistance (%) by 0-20% 1000-Time Repetitive Elongations and Shrinkages |
|---|---|---|---|---|---|---|
| Comparative Example 2-6 | CI-55 | 120° C./0.5 hr | 1.5 | 700 | Cutoff | 6800 |
| Comparative Example 2-7 | CI-56 | 120° C./0.5 hr | 2.9 | 1380 | Cutoff | 10000 |
| Comparative Example 2-8 | CI-57 | 120° C./0.5 hr | 3.9 | 670 | Cutoff | 9800 |
| Comparative Example 2-9 | CI-58 | 120° C./0.5 hr | 3.4 | 1700 | Cutoff | 13575 |
| Comparative Example 2-10 | CI-59 | 120° C./0.5 hr | 28 | Cutoff | Cutoff | Cutoff |
| Comparative Example 2-11 | CI-60 | 120° C./0.5 hr | 5.7 | Cutoff | Cutoff | Cutoff |
| Comparative Example 2-12 | CI-61 | 140° C./4 hr | 5.3 | 1300 | — | 12600 |
| Comparative Example 2-13 | CI-62 | 140° C./4 hr | 4.5 | 1210 | — | 11300 |

—: Not measured

It can be understood that, as shown in Tables 4 and 5, when a conductive paste composition to which the phenol compound of the present invention is added was used, increases in electric resistance due to wire elongation were small, and the resulting conductive wires were excellent in conduction stability against repetitive elongations and shrinkages (Examples 3-1 to 3-50). In contrast, in Comparative Examples 2-1 to 2-7, 2-12, and 2-13 free from phenol, and Comparative Examples 2-8 to 2-11 containing other additives, the electric resistances were greatly increased by wire elongation and the repetitive elongations and shrinkages, or the wires broke. In addition, in Comparative Examples 2-4 to 2-11, the wires broke upon 300% elongation.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A conductive paste composition, comprising (A) a conductive filler, (B) a phenol compound, (C) an elastomer resin, and (D) a solvent,
   wherein the phenol compound as the component (B) is represented by the following general formula (1B),

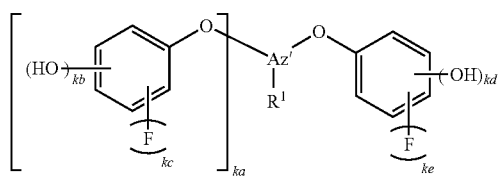

(1B)

wherein Az' represents a linear, branched, or cyclic (ka+2)-valent hydrocarbon group or fluorinated hydrocarbon group having 1 to 19 carbon atoms, and —$CH_2$— constituting the (ka+2)-valent hydrocarbon group is optionally substituted with —O—, —C(=O)— or —Si($R^2R^3$)—; "ka" represents 0 or 1, "kb", "kc", "kd", and "ke" each represent 1 or 2; $R^1$ represents a hydrogen atom, a halogen atom, a cyano group, or a hydroxyl group; and each of $R^2$ and $R^3$ is a linear, branched, or cyclic alkyl group having 1 to 6 carbon atoms, or a phenyl group.

2. The conductive paste composition according to claim 1, wherein the elastomer resin as the component (C) is polyurethane.

3. The conductive paste composition according to claim 2, wherein the elastomer resin as the component (C) is a polyurethane comprising a structure represented by the following general formulae (1a) to (1c),

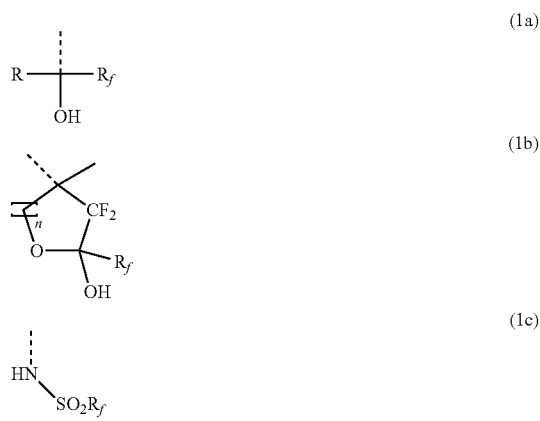

wherein R represents a hydrogen atom, a fluorine atom, or a linear, branched, or cyclic hydrocarbon group having 1 to 10 carbon atoms optionally substituted with a fluorine atom; $R_f$ represents a fluorine atom, or a linear, branched, or cyclic fluorinated hydrocarbon group having 1 to 10 carbon atoms; "n" is an integer of 1 or 2; and a dashed line represents a bonding arm.

4. The conductive paste composition according to claim 3, wherein the elastomer resin as the component (C) is a polyurethane comprising a structure represented by the following general formulae (2a) to (2c), (2a)
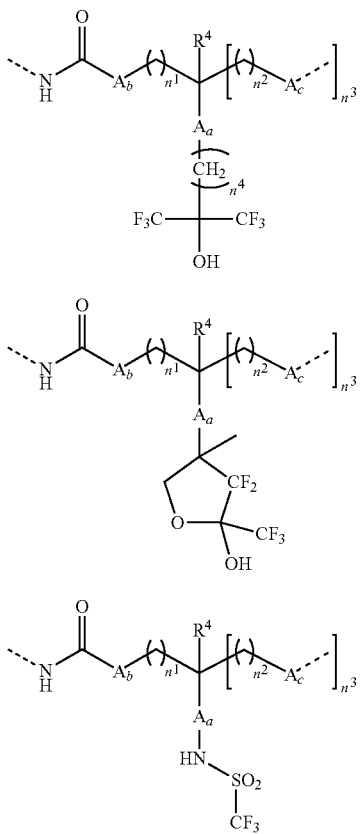
(2b)

(2c)

wherein $R^4$ is a hydrogen atom or a monovalent hydrocarbon group having 1 to 3 carbon atoms; $A_a$ represents a single bond, or a linear, branched, or cyclic divalent hydrocarbon group having 1 to 20 carbon atoms; and —$CH_2$— constituting $A_a$ is optionally substituted with —O—, —C(=O)—, —C(=O)O— or —$C_6H_4$—, or —$NR^8$—C(=O)—; $R^8$ is a hydrogen atom, or a linear or branched alkyl group having 1 to 4 carbon atoms; $A_b$ represents —O—, —$NR^8$—, or —C(=O)O—; $A_c$ represents —O—, —$NR^8$—, —C(=O)O—, or —$NR^8$—C(=O)—; each of $n^1$, $n^2$, and $n^4$ is an integer of 0 to 10; $n^3$ is an integer of 0 or 1; and a dashed line represents a bonding arm.

5. A method for producing the conductive paste composition according to claim 4, wherein the elastomer resin as the component (C) is produced using an alcohol represented by the following general formulae (3a) to (3c) as a chain extender, (3a)
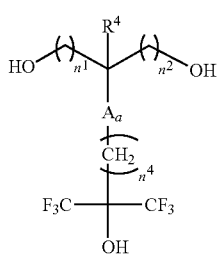

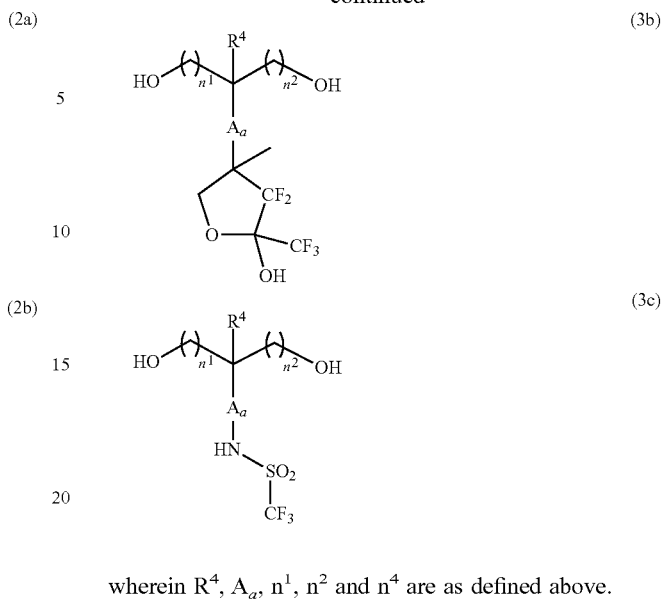

wherein $R^4$, $A_a$, $n^1$, $n^2$ and $n^4$ are as defined above.

6. The conductive paste composition according to claim 1, wherein the conductive filler as the component (A) is contained in a proportion exceeding 70 parts by mass relative to 100 parts by mass of a total of the components (A) and (C).

7. The conductive paste composition according to claim 1, wherein the conductive filler as the component (A) is selected from the group consisting of gold, silver, silver chloride, platinum, copper, tin, iron, titanium, nickel, palladium, aluminum, tungsten, molybdenum, ruthenium, chromium, indium, solder, carbon, and composites thereof.

8. The conductive paste composition according to claim 1, wherein the conductive filler as the component (A) is a silver powder having an average particle size of 5 nm to 10 μm.

9. A conductive wire formed on a substrate, the conductive wire comprising a baked product of the conductive paste composition according to claim 1.

10. The conductive wire according to claim 9, wherein the substrate is stretchable.

11. The conductive wire according to claim 9, wherein the substrate is a thermoplastic polyurethane.

12. The conductive wire according to claim 9, wherein a change in electric resistance upon 20% elongation is 500% or less.

13. The conductive wire according to claim 9, wherein a maximum electric resistance when the conductive wire is elongated and shrunk repeatedly 1000 times with an elongation ratio of 20% is 5000% or less of an electric resistance before the elongations and the shrinkages.

14. A method for producing a conductive wire by using the conductive paste composition according to claim 1 to form a conductive wire on a substrate, wherein the conductive wire is formed with a baking temperature of 60° C. to 160° C.

15. A method for producing a conductive wire, comprising printing the conductive paste composition according to claim 1, followed by heating to form a conductive wire on a substrate.

* * * * *